(12) United States Patent
Belli et al.

(10) Patent No.: US 7,968,695 B2
(45) Date of Patent: Jun. 28, 2011

(54) **NUCLEIC ACIDS ENCODING RECOMBINANT 56 AND 82 KDA ANTIGENS FROM GAMETOCYTES OF *EIMERIA MAXIMA* AND THEIR USES**

(75) Inventors: Sabina I. Belli, Lane Cove (AU); Nicholas C. Smith, Roseville (AU); Michael Wallach, St. Ives (AU)

(73) Assignee: Abic Biological Laboratories Ltd., Beit Shemesh (IL)

( * ) Notice: Subject to any disclaimer, the term of this patent is extended or adjusted under 35 U.S.C. 154(b) by 331 days.

(21) Appl. No.: 12/156,206

(22) Filed: May 30, 2008

(65) Prior Publication Data

US 2009/0196888 A1 Aug. 6, 2009

Related U.S. Application Data

(62) Division of application No. 10/483,159, filed as application No. PCT/US02/21233 on Jul. 3, 2002, now Pat. No. 7,423,137.

(60) Provisional application No. 60/303,699, filed on Jul. 6, 2001.

(51) Int. Cl.
| | |
|---|---|
| C07H 21/04 | (2006.01) |
| C07K 14/00 | (2006.01) |
| C12P 21/04 | (2006.01) |
| C12N 1/10 | (2006.01) |
| A61K 39/012 | (2006.01) |
| A61K 39/00 | (2006.01) |

(52) U.S. Cl. ............ 536/23.7; 435/69.3; 435/69.7; 435/258.4; 435/320.1; 530/300; 530/350; 424/265.1; 424/271.1

(58) Field of Classification Search .................. None
See application file for complete search history.

(56) References Cited

U.S. PATENT DOCUMENTS

| | | | |
|---|---|---|---|
| 5,496,550 | A | 3/1996 | Wallach et al. |
| 5,932,225 | A | 8/1999 | Wallach et al. |
| 7,423,137 | B2 * | 9/2008 | Belli et al. .......... 536/23.7 |
| 2005/0033042 | A1 | 2/2005 | Belli et al. |

FOREIGN PATENT DOCUMENTS

| | | |
|---|---|---|
| EP | 0135712 | 3/1985 |
| EP | 0164176 | 11/1985 |
| EP | 0167443 | 1/1986 |
| EP | 0256536 | 1/1996 |
| WO | 9000403 | 1/1990 |
| WO | 03004683 | 1/2003 |

OTHER PUBLICATIONS

Belli, S.I. et al. (2002) Functional Genomics of *gam56*: Characterisation of the role of 56 Kilodalton Sexual Stage Antigen in Oocyst Wall Formation in *Eimeria maxima, Int. J. of Parasitology* 32:1727-1737.

Belli, S.I., et al., Cloning and Characterization of the 82 kDa Tyrosine-Rich Sexual Stage Glycoprotein, GAM82, and Its Role in Oocyst Wall Formation in the Apicomplexan Parasite, *Eimeria maxima, Gene*, vol. 307:201-212, (2003).

Belli, S.I., et al., Roles of Tyrosine-Rich Precursor Gycoproteins and Dityrosine- and 3,4-Dihydroxyphenylalanine-Mediated Protein Cross-Linking in Development of the Oocyst Wall in the Coccidian Parasite *Eimeria maxima, Eukaryotic Cell*, vol. 2:456-464 (2003).

Bumstead et al., Clinical and Diagnostic Laboratory Immunology, 524-530 (Sep. 1995).

Danforth, H.D., et al., A Review of Progress in Coccidial Vaccine Development, *In Vith Intnl. Coccidiosis Conf.*, Guelph, Ontario, Canada, Barta, J.R. and Fernando, M.A. (ed.), pp. 49-60 (1993).

Eschenbacher, K. H., et al., Characterization of a 14kDa oocytst wall protein of *Eimeria tenella* and *E. Acervulina, Parasitology*, vol. 112 :169-176 (1995) (Abstract).

Fried, M., et al., Developmental gene expression of a 230-kilodalton macrogamete-specific protein of the avian coccidial parasite, *Eimeria maxima, Mol. & Biochem. Parasitol.*, vol. 51:251-262 (1992).

Gilbert, et al., An Enzyme-Linked Immunosorbent Assay for Coccidiosis in chickens: Correlation of Antibody Levels with Prior Exposure to Coccidia in the Laboratory and in the Field, *Avian Disease*, vol. 32:688-694 (1988).

Hein, H., *Eimeria brunetti*: Cross Infections in Chickens Immunized to *E. maxima, Experimental Parasitology*, vol. 29:367-374 (1971).

Jobling et al., Mol. Microbiol., vol. 5:1755-67 (1991).

Karkhanis, Y.D., et al., Purification and characterization of a protective antigen for *Eimeria tenella, Infect. & Immun.*, vol. 59:983-989 (1991).

Kowlaczyk et al., Quantitation of Maternal-Fetal Egg Transport in the Chicken, *Immunology*, vol. 54:755-762 (1985).

Larsen, N.C., et al., Production and Partial Characterization of Monoclonal Antibodies Specific for the Gamonts of *Eimeria tenella, The J. Parasitology*, vol. 77(6):1012-1015 (1991).

Laxer, M.A., et al., Production of Monoclonal Antibodies Specific for *Eimeria tenella* Microgametocytes, *The J. Parasitology*, vol. 73 (3):611-616 (1987).

(Continued)

*Primary Examiner* — Larry R Helms
*Assistant Examiner* — Padma V Baskar
(74) *Attorney, Agent, or Firm* — John P. White; Cooper & Dunham LLP

(57) ABSTRACT

The present invention provides the recombinant cloning and sequencing of two of the major *Eimeria maxima* gametocyte antigens having molecular weights of 56 and 82 kDa and the expression of these recombinant antigens in an *E. coli* expression system using the plasmid pTrcHis. The subject invention also provides a vaccine against coccidiosis comprising the recombinant 56 kDa or 82 kDa antigen. The subject invention also provides two 30 kDa proteins and three 14 kDa proteins from *Eimeria maxima* gametocytes having at the N-terminal end the amino acid sequence described herein. The subject invention also provides a vaccine against coccidiosis comprising the recombinant 56 kDa or 82 kDa antigen and any of the aforementioned proteins. Additionally, the subject invention also provides a method of immunizing a subject against infection by *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising the step of administering to the subject any of the aforementioned vaccines.

18 Claims, 36 Drawing Sheets

OTHER PUBLICATIONS

Long, P.L., et al., Effects of Fowl Sera on Some Stages in the Life Cycle of *Eimeria tenella*, *Experimental Parasitology*, vol. 14:210-217 (1963).

Long, P.L., et al., Immunity to coccidiosis: effect of serum antibodies on cell invasion by sporozoites of *Eimeria* in vitro, *Parasitology*, vol. 65:437-445 (1972).

Losch et al., The Chicken Egg, an Antibody Source, *J. Vet Med B*. vol. 33:609-619 (1986).

Mencher, D. et al., Antigenic proteins of *Eimeria maxima* gametocytes: cell-free translation and detection with recovered chicken serum, *Exp. Parasitol.*, vol. 68:40-48 (1989)(Abstract).

Pugatsch, T., et al., *Eimeria maxima*: Isolation of Gametocytes and Their Immunogenicity in Mice, Rabbits, and Chickens, *Experimental Parasitology*, vol. 68:127-134 (1989).

Rose, M.E., Immunity to *Eimeria brunetti* and *Eimeria maxima* infections in the fowl, *Parasitology*, vol. 57:363-370 (1967).

Rose et al., Immunity to coccidiosis: protective effects of transferred serum and cells investigated in chick embryos infected with *Eimeria tenella*, *Parasitology*, vol. 63:299-313 (1971).

Rose, M.E., Immunity to Coccidiosis: Maternal transfer in *Eimeria Maxima* Infections, *Parasitology*, vol. 65:273-282 (1972).

Rose, M.E., Protective antibodies in infections with *Eimeria maxima*: the reduction of pathogenic effects in vivo and a comparison between oral and subcutaneous administration of antiserum, *Parasitology*, vol. 68:285-292 (1974).

Rose, M.E., Immunity to *Eimeria maxima*: Reactions of Antisera in vitro and Protection in vivo, *The Journal of Parasitology*, vol. 60(3):528-530(1974).

Rose, M.E., Immunity to coccidiosis: stages of the life-cycle of *Eimeria maxima* which induce, and are affected by, the response of the host, *Parasitology*, vol. 73:25-37 (1976).

Rose, M.E., *Eimeria, Current Topics in Microbiology and Immunology*, (A. Clarke, et al. eds.), vol. 120:7-17 (1985).

Rudinger, et al., in "Peptide Hormones", edited by Parsons, J.A., University Park Press, Jun. 1976, p. 6.

Shirley, M.W., et al., *Eimeria* spp. from the Chicken: from Merozoites to Oocysts in Embryonated Eggs, *Parasitology*, vol. 83:259-267 (1981).

Smith, N.C., et al., Maternal transmission of immunity to *Eimeria Maxima*: western blot analysis of protective antibodies induced by infection, *Infection & Immunity*, 62(11): 4811-4817 (1994).

Song et al., Antibodies to the α-Subunit of Insulin Receptor from Eggs of Immunized Hens, *The Journal of Immunology*, vol. 135:3354-3359 (1986).

Stotish, R.L., et al., Preparation and Purification of Merozoites of *Eimeria tenella*, *The Journal of Parasitology*, vol. 61(4):700-703 (1975).

Tomley, F.M. et al. EtMIC4: a Microneme Protein from *Eimeria tenella* that Contains Tandem Arrays of Epidermal Growth Factor-like Repeats and Thrombospondin Type-I Repeats, *Int. J. of Parasitology* 31 : 1303-1310 (2001).

Wallach, M. et al. Maternal Immunization with Gametocyte Antigens as a Means of Providing Protective Immunity Against *Eimeria maxima* in Chickens, *Infection and Immunity* 60(5):2036-2039 (1992).

Wallach, M., et al., *Eimeria maxima*: Identification of Gametocyte Protein Antigens, *Experimental Parasitology*, vol. 68 (1):49-56 (1989).

Wallach, M., et al., Passive Immunization of chickens against *Eimeria maxima* Infection with a Monoclonal Antibody Developed against a Gametocyte Antigen, *Infection and Immunity*, vol. 58:557-562 (1990).

Wallach, M., et al., *Eimeria maxima* gametocyte antigens: potential use in a subunit maternal vaccine against coccidiosis in chickens, *Vaccine*, vol. 13:347-354 (1995).

Wallach, M., et al., Progress Towards a Subunit Vaccine Against Coccidiosis, *Misset's World Poultry, Supplement Coccidiosis*, No. 2:22-24 (1996).

Witcombe, D.M. et al. Molecular Characterisation of EmTFP250: A Novel Member of the TRAP Protein Family in *Eimeria maxima, Int. J. of Parasitology* 33:691-702 (2003).

Supplementary European Search Report issued Jun. 16, 2005 in connection with European Application No. 02 746 870.1.

Database EMBL mic4 Gene, (2001) XP002313642, Abstract.

* cited by examiner

FIGURE 2
 
Immunoblot  Silver stain
(anti-APGA)

FIGURE 4

Sequence Range: 1 to 1754

```
           10         20         30         40         50         60         70
AGCAGAACATAGGGAGTTCATCTGTTCCTTCTTTTCATCATTTATTCCTCGTTTCTCACCGTTTTATTTT
TCGTCTTGTATCCCTCAAGTAGACAAGGAAGAAAAGTAGTAAATAAGGAGCAAAGAGTGGCAAAATAAAA 80         90        100        110        120        130        140
TTTTGTGTAACCCTCTCCGCTGTTGAGTCCCAATGACCGGCCTCGGCCTCGCTGCTGTCGCGCTGGCTCT
AAAACACATTGGGAGAGGCGACAACTCAGGGTTACTGGCGGAGCCGGAGCGACGACAGCGCGACCGAGA
                                        M  T  R  L  G  L  A  A  V  A  L  A  L>
                                        predicted initiator methionine 150        160        170        180        190        200        210
CGCCGTGGGCCCCTTCCATGGCAGTGCCCAGCACCACTCCTGTGGAGAATCAGGTTCACCCTTACAGCGAG
GCGGCACCCGGGAAGGTACCGTCACGGGTCGTGGTGAGGACACCTCTTAGTCCAAGTGGGAATGTCGCTC
 A  V  G  P  S  M  A  V  P  S  T  T  P  V  E  N  Q  V  H  P  Y  S  E>
            predicted signal peptide cleavage site            amino terminus 220        230        240        250        260        270        280
ATGAGTACCTACCAGGAGGGGAGTGCCCCGGGGCTCCGGAGGACACCACCACCACCACTACGTCGTCCC
TACTCATGGATGGTCCTCCCCTCACGGGGCCCCGAGGCCTCCTGTGGTGGTGGTGGTGATGCAGCAGGG
 M  S  T  Y  Q  E  G  S  A  P  G  A  P  E  D  T  T  T  T  T  T  S  S>

290        300        310        320        330        340        350
CTGTTTCCGATGGAGCCGAGCAGTGGCTTGAGAGCTTTGTTCGTGCTGTGCAGCGCCAGCTGCAGCTTCA
GACAAAGGCTACCTCGGCTCGTCACCGAACTCTCGAAACAAGCACGACACGTCGCGGTCGACGTCGAAGT
 P  V  S  D  G  A  S  Q  W  L  E  S  F  V  R  A  V  Q  R  Q  L  Q  L  Q>
                                                    tryptic peptide sb56c 360        370        380        390        400        410        420
GGACCAAATGATGCGTCAGCTCATGAGGGACATTCAGGAGTACCTGAGCACTGCGTTCAACTGGGCAGAG
CCTGGTTTACTACGCAGTCGAGTACTCCCTGTAAGTCCTCATGGACTCGTGACGCAAGTTGACCCGTCTC
 D  Q  M  M  R  Q  L  M  R  D  I  Q  E  Y  L  S  T  A  F  N  W  A  E>
                                                    tryptic peptide sb56fc 430        440        450        460        470        480        490
AACCAGTCTACTGCCTACACCCGTGTTACCGACATGATGGACATGATCTCCAACAGAATGAATGCAGCAA
TTGGTCAGATGACGGATGTGGGCACAATGGCTGTACTACCTGTACTAGAGGTTGTCTTACTTACGTCGTT
 N  Q  S  T  A  Y  T  R  V  T  D  M  M  D  M  I  S  N  R  M  N  A  A>
                                                    tryptic peptide sb5
```

FIGURE 4 (CONTINUED)

```
         500        510        520        530        540        550        560
TGGACAGCTCAAACGAACTCATGACCACTAGCGACACCACAGACCCCGAGACCCTCCGCCGTGCAACTCG
ACCTGTCGAGTTTGCTTGAGTACTCGTCATCGCTGTGGTGTCTGGGGCTCTGGGAGGCGGCACGTTGAGC
  M  D  S  S  M  X  L  M  V  T  S  D  T  T  D  P  E  T  L  R  R  A  T  R>

570        580        590        600        610        620        630
CAAGTACATGAAGGAGGTTCGCGTTCAGGACGTCCTGGTAGATGCTCTCTGGGCCTCTCTCCGCGGTGTA
GTTCATGTACTTCCTCCAAGCGCAAGTCCTGCAGGACCATCTACGAGAGACCCGGAGAGGCGCCACAT
  K  Y  M  K  E  V  R  V  Q  D  V  L  V  D  A  L  W  A  S  L  R  G  V>
                                                    tryptic peptide sb56a 640        650        660        670        680        690        700
CAGACAGCTGCCTGGATGAATGGAGTGACGGCTATTGAGAAGGAGGAGACGACTCCCATGGCTAGCCGCG
GTCTGTCGACGGACCTACTTACCTCACTGGCGATAACTCTTCCTCCTCTGCTGAGGGTACCGATCGGCGC
  Q  V  A  A  W  M  N  G  V  T  A  I  E  K  E  E  T  T  P  M  A  S  R>
                    tryptic peptide sb56g 710        720        730        740        750        760        770
CTGCTGAGGAGTTCCTCCACCGCATGTACCATAACCTGAGGGCAGCACGTATGTCTGAAGAAGATGTTGC
GACGACTCCTCAAGGAGGTGGCGTACATGGTATTGGACTCCCGTCGTGCCATACAGACTTCTTCTACAACG
  A  A  E  E  F  L  H  R  M  Y  H  N  L  R  A  A  G  M  S  E  E  D  V  A>
tryptic peptide sb56d 780        790        800        810        820        830        840
CAAGTTCATCCCTAGAGCCGAGTACAACCCCTCCGAGCAGTCAAGAAATATGGGCAGAAAGCGCAGGAGC
GTTCAAGTAGGGATCTCGGCTCATGTTGGGGAGGCTCGTCAGTTCTTTATACCCGTCTTTCCCGTCCTCG
  K  F  I  P  R  A  E  Y  N  P  S  S  Q  S  R  N  M  G  R  K  G  R  S>

850        860        870        880        890        900        910
TTCTACTACGGCGGCTATCCCAGCTACTACAACTCCCCCTACTACAGCTACAGCAGCTACCCCAGCTACT
AAGATGATGCCGCCGATAGGGTCGATGATGTTGAGGGGGATGATGTCGATGTCGTCGATGGGGTCGATGA
  F  Y  Y  G  G  Y  P  S  Y  Y  N  S  P  Y  Y  S  Y  S  S  Y  P  S  Y>

920        930        940        950        960        970        980
ACAACTACAGCTACCCGTCATACAGCTACAGCAGCTACCCCAGCTACTACCGCTACAGCAGCTACCCCTA
TGTTGATGTCGATGGGCAGTATGTCGATGTCGTCGATGGGGTCGATGATGGCGATGTCGTCGATGGGGAT
  Y  N  Y  S  Y  P  S  Y  S  Y  S  S  Y  P  S  Y  Y  R  Y  S  S  Y  P  Y>

990       1000       1010       1020       1030       1040       1050
CTACAACTACAGCTATCCCAGCTACTACAACTACGGCAGCTACCCCTACTACAGTTATAGCAGCTACCCC
GATGTTGATGTCGATAGGGTCGATGATGTTGATGCCGTCGATGGGGATGATGTCAATATCGTCGATGGGG
  Y  N  Y  S  Y  P  S  Y  Y  N  Y  G  S  Y  P  Y  Y  S  Y  S  S  Y  P>

1060       1070       1080       1090       1100       1110       1120
AGCTGGTACTGGCGCCGTCTCCGCTCTTTGGCAACAGCAACTTGCCCAGACTGCCCTCCTCTCACCACTC
TCGACCATGACCGCGGCAGAGGCGAGAAACCGTTGTCGTTGAACGGGTCTGACGGGAGGAGAGTGGTGAG
  S  W  Y  W  R  R  L  R  S  L  A  T  A  T  C  P  D  C  P  P  L  T  T>
```

FIGURE 4 (CONTINUED)

```
        1130      1140      1150      1160      1170      1180      1190
CCAGCATGATCCCAACTCCCCCCCCAATGATGAACATGATGAACACCCCACCCCCCATGGCAAACATGAT
GGTCGTACTAGGGTTGAGGCGGGGGTTACTACTTGTACTACTTGTGGGTGGGGGTACCGTTTGTACTA
     P  S  M  I  P  T  P  P  M  M  M  M  N  T  P  P  P  M  A  N  M  M>

1200      1210      1220      1230      1240      1250      1260
GACCAGCATGATGATGAACACTCCCATGGTTCCTCCTCCCCGCACCCTCGAACTGAAGCCATGAGCCTC
CTGGTCGTACTACTACTTGTGAGGGTACCAAGGAGGAGGGGCGTGGGAGCCTTGACTTCGGTACTCGGAG
     T  S  M  M  N  T  P  N  V  P  P  R  T  L  G  T  E  A  M  S  L>

1270      1280      1290      1300      1310      1320      1330
GGCTTGGCCCCCATCGTATCACCGGCGCCCCCATGACAGGTTTCGGTGTTCCTCCTGAGTTCGGTCCCT
CCGAACCGGGGGTAGCCATAGTGGCCGCGGGGTACTGTCCAAAGCCACAAGGAGGACTCAAGCCAGGA
     G  L  A  P  I  G  I  T  G  A  P  M  T  G  F  G  V  P  P  E  F  G  P>

1340      1350      1360      1370      1380      1390      1400
TTGGAGCCGAAGGTATCGGCCTCCCCACCGATGCCCTCGGCAGCACCCCGAAATGACACCATTCGACCC
AACCTCGGCTTCCATAGCCGGAGGGGTGGCTACGGGAGCCGTCGTGGGGCTTTACTGTGGTAAGCTGGG
     F  G  A  E  G  I  G  L  P  T  D  A  L  S  T  F  N  M  T  S  D  P>
                                            Biotech Aus. tryptic peptide 1410      1420      1430      1440      1450      1460      1470
AACTACCCCCTACAGAACTCTCGCCCCCATGGACCTCCCCCCCATCCCCCCTCCTGTCTTCCCTGAAACC
TTGATGGGGATGTCTTCAGAGCGGGGGTACCTGGAGGGCGGGGTAGGGGGGAGGACAGAAGGGACTTTGG
     T  T  P  Y  R  T  L  A  P  M  D  L  P  P  I  P  P  F  V  F  P  E  T>

1480      1490      1500      1510      1520      1530      1540
CCTATGAAGCCACCTACTCCCTTCGGCTTCGGACCTGCACCTGTTCCTCCCATGCCCTTCTAAAACGACCT
GGATACTCCGGTGGATGAGGGAAGCCGAAGCCTGGACGTGGACAAGGAGGGTACGGAAGATTTGCTGGA
     P  M  K  P  P  T  P  F  G  F  G  P  A  P  V  P  P  M  P  F  *
                                                                  stop 1550      1560      1570      1580      1590      1600      1610
ACCATCCCTCAATCCATAGCTCACATTTCGTAGCCTCAAAACAGTTTTTTGTTCATTTCACTTCCAGGAC
TGGTAGGGAGTTAGGTATCGAGTGTAAAGCATCGGAGTTTTGTCAAAAAACAAGTAAAGTGAAGGTCCTG 1620      1630      1640      1650      1660      1670      1680
TCATGCTGCGACATTTGCATTCGTACCTCGAAAACGTCAACCTCAAACCCCAAACCATTCTGTGACCTCC
AGTACGACGCTGTAAACGTAAGCATGAGCTTTGCAGTTGGAGTTTGGGGTTTGGTAAGACACTGGAGG 1690      1700      1710      1720      1730      1740      1750
CCTCGCAAACGCGGAAGGCGGAACATTTTTTCTGAAGTATATTACTACGTTAAAAAAAAAAAAAAAAAAA
GGAGCGTTTGCGCCTTCCGCCTTGTAAAAAAGACTTCATATAATGATGCAATTTTTTTTTTTTTTTTTT

AAAA
TTTT
```

FIGURE 5

Sequence Range: 1 to 2145

```
         10        20        30        40        50        60        70
ATACAAATCCTTTTTATCTGGTTCCAACACGCTCACTCAACCACCACCTGGACACACCCTCCCCATACAT
TATGTTTAGGAAAAATAGACCAAGGTTGTGCGAGTGAGTTGGTGGTGGACCTGTGTGGGAGGGGTATGTA 80        90       100       110       120       130       140
ACAGGAGCAGCAGCAACACCAGCATCAAGATGACGCGTGCGGCAGCGCTTGCCGGGGTTTTGGCCCTGGC
TGTCCTCGTCGTCGTTGTGGTCGTAGTTCTACTGCGCACGCCGTCGCAACGGCCCCAAAACCGGGACCG
                               M  T  R  A  A  A  L  A  G  V  L  A  L  A>
                                      Predicted initiator methionine 150       160       170       180       190       200       210
TGCAGCAGGCAGCAGCCTTGCTCTACCTACTGTATTGGACACAACGACTGGCACCCAAGTGGAGTGGACT
ACGTCGTCCGTCGTCGGAACGAGATGGATGACATAACCTGTGTTGCTGACCGTGGGTTCACCTCACCTGA
 A  A  G  S  S  L  A  L  P  V  L  D  T  T  T  G  T  Q  V  E  W  T>
      Predicted signal peptide cleavage site               amino terminus 220       230       240       250       260       270       280
GAGACCCCCTTAGACACAACAGAGGTAACTATGGGGGAGATGGGCAGCAACCACCAGCGGCACGACTGCAA
CTCTGGGGGAATCTGTGTTGTCTCCATTGATACCCCCTCTACCCGTCGTGGTGGTCGCCGTGCTGAGGTT
 E  T  P  L  D  T  T  E  V  T  M  G  E  M  G  S  T  T  S  G  T  T  P>

290       300       310       320       330       340       350
CCAGCACTGGTGTGCCGAATGATGGAGGCTGAAACTACAACCCCATCAACCCCTGAGGCTCCCCAGCAGCA
GGTCGTGACCACACGCTTACTACCTCCGACTTTGATGTTGGGGTAGTTGGGGACTCCGAGGGGTCGTCGT
 T  S  T  G  V  R  M  M  E  A  E  T  T  T  P  S  T  P  E  A  P  Q  Q  Q>

360       370       380       390       400       410       420
GCAGCAGATGCCTCAGCCTCAACCTCAGCCACAGCAAACAACTCCCGTTCCTGAGGCGGTATTAGAGGCA
CGTCGTCTACGGAGTCGGAGTTGGAGTCGGTGTCGTTTGTTGAGGGCAAGGACTCCGCATAATCTCCGT
 Q  Q  M  P  Q  P  Q  P  Q  P  Q  Q  T  T  P  V  P  E  A  V  L  E  A>

430       440       450       460       470       480       490
ATTATGCAAGAAATGCAAAATATTTTCCGTTCTTCTCTTGTACCAGGTTGGATACTGTCGGTACAGCAG
TAATACGTTCTTTACGTTTTATAAAAGGCAAGAAGAGAACATGGTCCAACCCTATGACAGCCATGTCGTC
 I  M  Q  E  M  Q  N  I  F  R  S  S  L  V  P  G  W  D  T  V  Q  T  A>
```

```
        1130      1140      1150      1160      1170      1180      1190
GACATTATTACAGGAGACTTGCTCAGCAGGAACCAAGACCTGTTATGCCTCCTGCAGCAGCAACTGCCGC
CTGTAATAATGTCCTCTGAACGACTCGTCCTTGGTTCTGGACAATACGGAGGACGTCGTCGTTGACGGCG
 G  H  Y  Y  R  R  L  A  E  Q  E  P  R  P  V  M  P  P  A  A  A  T  A  A>
                                          tryptic peptide 82f 1200      1210      1220      1230      1240      1250      1260
AGCAAACCTAAGAGCAGCAGCAGCAGCAGCAGCAGAAGTACCACCACCACCACCACCAGCAGCAGTACCA
TCGTTTGGATTCTCGTCGTCGTCGTCGTCGTCGTCTTCATGGTGGTGGTGGTGGTCGTCGTCATGGT
 A  N  L  R  A  A  A  A  A  A  A  E  V  P  P  P  P  P  P  A  A  V  P>

1270      1280      1290      1300      1310      1320      1330
CCACCACCACCAGCAGCAGCAGCAGGTACCCCAGCTATGATGCCTCCTCCTATGATGCGTGTTCAAGAAC
GGTGGTGGTGGTCGTCGTCGTCGTCCATGGGGTCGATACTACCGAGGAGGATACTACCCACAACTTCTTG
 P  P  P  P  A  A  A  A  G  T  P  A  M  M  P  P  P  M  M  G  V  E  E>

1340      1350      1360      1370      1380      1390      1400
CTGTTCCTTTCCGCTCCCTCTATCCTAGCTATAGCTGGAGTTATCCAGCATATACTCGCGTGTCTCCCTC
GACAAGGAAAGGCGAGGGAGATAGGATCGATATCGACCTCAATAGGTCGTATATGAGCGCACAGAGGGAG
 P  V  P  F  R  S  L  Y  P  S  Y  S  W  S  Y  P  A  Y  T  R  V  S  P  S>

1410      1420      1430      1440      1450      1460      1470
TTATTCTTATTATACACCCTCTTATAGTTCTTCTTACTATTATCCCCGGTTATAATTATGCCTATAACTAT
AATAAGAATAATATGTGGGAGAATATCAAGAAGAATGATAATAGGGGCAATATTAATACGGATATTGATA
 Y  S  Y  Y  T  P  S  Y  S  S  S  Y  Y  Y  P  R  Y  N  Y  A  Y  N  Y>

1480      1490      1500      1510      1520      1530      1540
CCCTTATATTCAGACTATAGCTGGTATGATTATAGCTACCCCCTTGCCTACAGCAGCTATAGTAGCTACC
GGGAATATAAGTCTGATATCGACCATACTAATATCGATGGGGAACGGATGTCGTCGATATCATCGATGG
 P  L  Y  S  D  Y  S  W  Y  D  Y  S  Y  P  L  A  Y  S  S  Y  S  S  Y>

1550      1560      1570      1580      1590      1600      1610
CCCTTTCCTATAGTAGCTATAGCTACCCCCTTAGCTATACCTACCCTAGTGCCTTTTATAGAAGACTAGA
GGGAAAGGATATCATCGATATCGATGGGGGAATCGATATGGATGGATCACGGAAAATATCTTCTGATCT
 P  L  S  Y  S  S  Y  S  Y  P  L  S  Y  T  Y  P  S  A  F  Y  R  R  L  E>

1620      1630      1640      1650      1660      1670      1680
GGTCCCTGATCTAACAACAACTACTACTACTCATCATGAGCAGCAGCAGCAGCAGCAGCAAGAAAGTACA
CCAGGGACTAGATTGTTGTTGATGATGATGAGTAGTACTCGTCGTCGTCGTCGTCGTCGTTCTTTCATGT
 V  P  D  L  T  T  T  T  T  T  H  H  E  Q  Q  Q  Q  Q  Q  Q  E  S  T>

1690      1700      1710      1720      1730      1740      1750
ACTACTGCTGTACCTACAGAAACCATTACTACTCCCTCTACTCGTAATACACACAGCAGCAGCCTAAGAA
TGATGACGACATGGATGTCTTTGGTAATGATGAGGGAGATCAGCATTATGTGTGTCGTCGTCGGATTCTT
 T  T  A  V  P  T  E  T  I  T  T  P  S  T  R  N  T  H  S  S  S  L  R>
```

FIGURE 5 (CONTINUED)

```
          1760       1770       1780       1790       1800       1810       1820
GAGTAGCAGAAAGATATGAGCCTATTACCCCTACACAAAGAACTTTTTATAATAATACAGAAGGTACTAA
CTCATCCTCTTTCTATACTCGGATAATGGGGATGTGTTTCTTGAAAAATATTATTATGTCTTCCATGATT
  S  V  G  E  R  Y  E  P  I  T  P  T  Q  R  T  F  Y  N  N  T  E  G  T  N>
                                                         Biotech Aus. tryptic peptide 1830       1840       1850       1860       1870       1880       1890
CAACCCTGTCTATACACCCGAAAATCTTACAGAAGATGAACCACAAACTGTATGGGAAACATACAACTAA
GTTGGGACAGATATGTGGGCTTTTAGAATGTCTTCTACTTGGTGTTTGACATACCCTTTGTATGTTGATT
  N  P  V  Y  T  P  E  N  L  T  E  D  E  P  Q  T  V  W  E  T  Y  N  *>
                                                                          stop 1900       1910       1920       1930       1940       1950       1960
ACCCTAAACCCTAAACCCTAAACCCTCAACCCTAACATTTCTCATTTTTTTATAGAGAAATTTTAGGGAA
TGGGATTTGGGATTTGGGATTTGGGAGTTGGGATTGTAAAGAGTAAAAAAATATCTCTTTAAAATCCCTT 1970       1980       1990       2000       2010       2020       2030
CACTAACCTGCCTGCCTTGCCATCGTTTATATATATCCATTTGTTTATTAATAAACAATTTTTATTTACC
GTGATTGGACGGACGGAACGGTAGCAAATATATATAGGTAAACAAATAATTATTTGTTAAAAATAAATGG 2040       2050       2060       2070       2080       2090       2100
TCTAGTCGTCTTTTTATTAACAGCGCTTATTCGCGTTGTTTATACAAACTACTACTATTTTTACCCAATA
AGATCAGCAGAAAAATAATTGTCGCGAATAAGCGCAACAAATATGTTTGATGATGATAAAAATGGGTTAT 2110       2120       2130       2140
ATACTTGTACAGGCATTTTTTAAAAAAAAAAAAAAAAAAAAAAAAA
TATGAACATGTCCGTAAAAAATTTTTTTTTTTTTTTTTTTTTTTTT
```

FIGURE 9
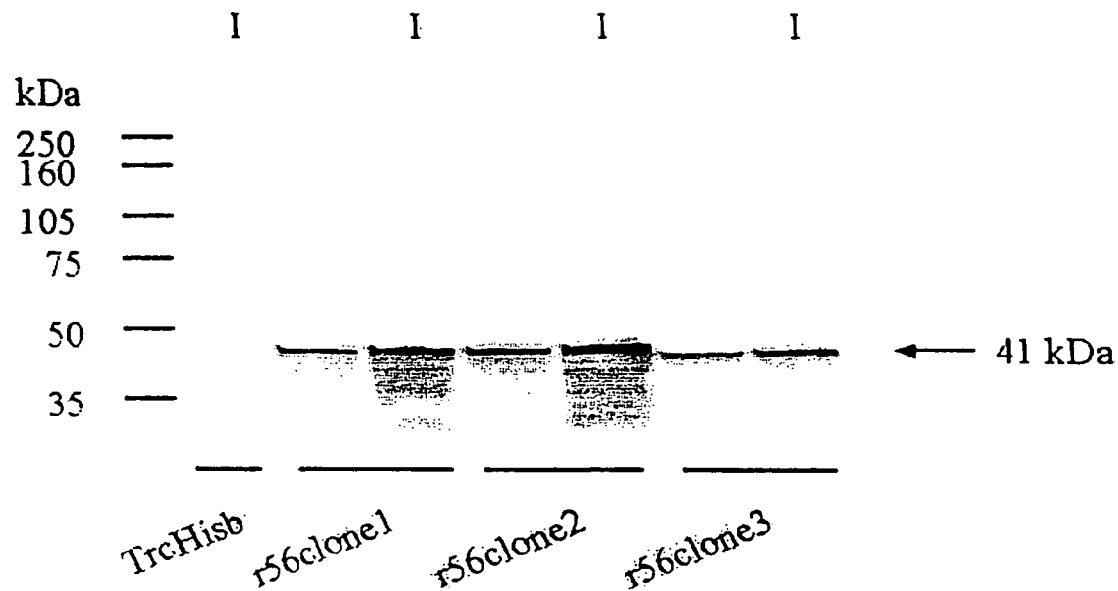
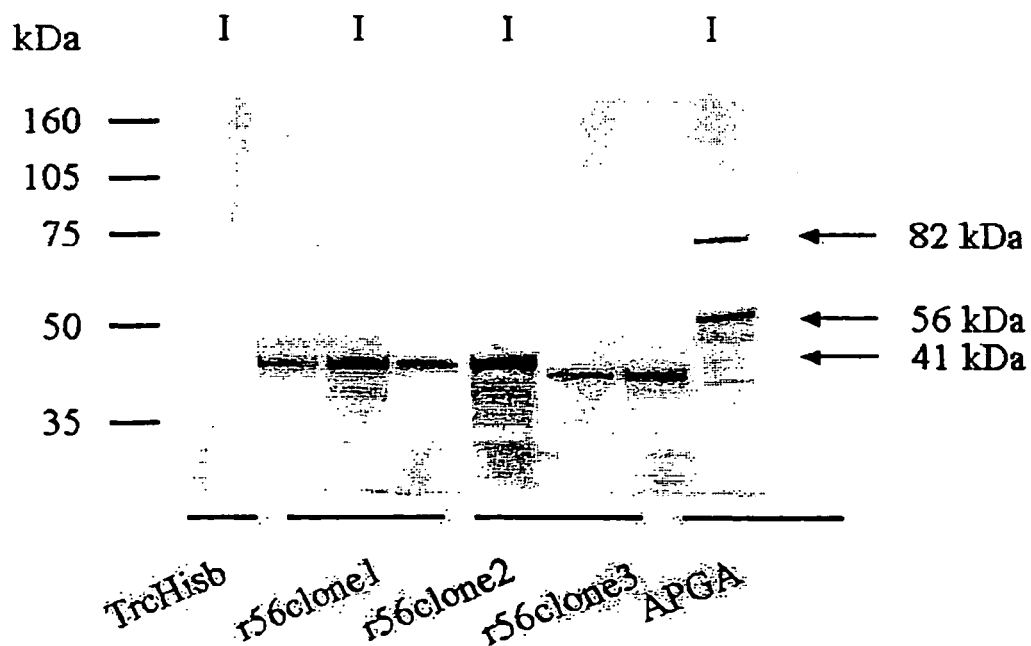

FIGURE 12

```
230      1 ATGCTGCATCGCAACCCGCGGTGGGCGCTTTGTGCAGCCCTCGCTGCACT  50
WO 9     1                                                      0

230     51 CTATGGCGGAACAGGAATCGCCAGCGCCGAAGTTAACAATGAATTGAGCA 100
WO 9     1                                                      0

230    101 AGTGCGAATCTGGGTGGACACCCTGGACTACCTGCAACCCGCAAACTGGT 150
WO 9     1                                                      0

230    151 CTGCGGGAGAGGCACAATGCACAGTGCGAGACATGGGTGGAGGTTGAGGA 200
WO 9     1                                                      0

230    201 ATGCCAGAAGCTGACAGGATGTGGCAACTGGACTCCTTGGTCTCCGGCG  250
WO 9     1                                                      0

230    251 ATATGTCGTGTGTGGTGGGACAGTTTCAAACCCGCAACAGGGAGGGCTGC 300
WO 9     1                                                      0

230    301 CCAGAGGTGCAGGAAGTGAGGGCATGCAGGCCTGTACTTCTAGAATCCAA 350
WO 9     1                                                      0

230    351 CGATCAATGGACCCCCTGGACAATGTGCGACACCAACCGCGTCCAGGAAA 400
WO 9     1                                                      0

230    401 GATACAACTCAAAGTGCGGACCCGTCGAAGTCCGCGAGTGCAACATGGAC 450
WO 9     1                                                 ATG   3
```

FIGURE 12 (CONT.)

```
230   451 GACGCAGAGATCGAGAAATGCGGCGAGTTCGTGGAATGGGATGCCCCTAT  500
WO 9    4 GGTTTTTTCGTCTTCACAGGCGGTGATTTCGGCGACTGGAGCCCCCCTCT   53
            *     **    *  *  ****  **  ****   **  ***     ****** *

230   501 GAATGGAGACTGCGTACGCGGGGGTACCCACACGCGTTACCGTCAAAACT  550
WO 9   54 CGCTGGTGACTGCGTGCCTGGCACTACTCACACACGCCAGAGGGCAAATT  103
            ***  ********   **    ***  *****  **    *  *   *** *

230   551 GCCCAGACCGCAAAGAGGTGCGGGTGTGCGGAGCCTTTGATTGCAGTAGC  600
WO 9  104 GCCCAAACCACAAGGAGGTGCGGGTTTGCGGCGCCTTCGATTGTAGCCAG  153
            *****  ***  ***  ************   *****  *****  *****  **

230   601 TGCTCTGTAAACGCCACTTGCGATCCCATTGGTGCATCCTGCGAATGCAA  650
WO 9  154 TGCTCAGTCAACGCTACCTGCGACCCCCTCGGAGCCACTTGTCAGTGCAA  203
            *****  **  *****  **  *****  ***   *  **  **    *  **   **  *****

230   651 GCCTGGTTTCCGCGGCAATGGGAAGACCTGCGAGGCCTTCAACCCCTGCG  700
WO 9  204 ACCGGGTTTCCGAGGCGATGGGACTCAGTGCGAGGCATTCAACCCTTGCG  253
            ** ********  ***   ******    **  ******  ********   ****

230   701 AAGATACCCCTGCACCTTGCGACAGCAACGCCATCTGCACCCCAGACGCA  750
WO 9  254 AAGGGAGACGGCTCCTTGTCATGCGAACGCGACCTGCACGGCTGATGGA  303
            ***          *  ** *****  **    *****  *  ******    *  **  *  *

230   751 A-TGACGCCAAATGCCAGTGCAAGGCAGGCTGGGACCCAGATTCCGGAGC  799
WO 9  304 AATGACGCCAAATGCCACTGCAACAAGGGCTGGAACGCAGACAGCAAGGC  353
            *  ***************  *****  *  ****    ****** *****    *    **

230   800 AGGCAGCAGCAAGAAGCCTTGCGTTGAGGTCGACGAGTGCGCATCCAACA  849
WO 9  354 AGGTGCCAGCGGTCACGCATGCGTGGAGGAGGACGAATGCGCCAACAACA  403
            ***  ****     *  *  *****  ****  *****  *****      *****

230   850 CCCACCAGTGCCCGGCACACTCCACATGCATCAACACCAAGGGCTCTTAT  899
WO 9  404 CGCACGAATGTCCGCAGCACTCAACTTGCGTCAACACTGAGGGCTCCTAT  453
            *  ***  *  **  ***     *****  **  ***  *******    ********  ***

230   900 AAGTGCGACTGCAACCAGGGATACCGTCAAGGGAGAGGACGGACAGTGTC  949
WO 9  454 GAATGCAACTGCTTACCGGGTTATCAG-AAGGATCAGGATGGAAATGCC  502
            *  ***  *****     *  ***  **  *     ****    ****  **  *  **  *

230   950 ATGACGTCGATGAATGCACCAACGGAGAGCACACCTGCCCGCTCACTCC  999
WO 9  503 AGGACATAGACGAGTGCGCT---GGGGAACATGGTTGTCCCGCACACTCG  549
            *  ***  *  **  **  ***  *      **  **  **      **  *****  *****

230  1000 ACTTGTTTGAATACAGCTGGCAGCTACGAGTGCCGCTGCGACACTGGGTA 1049
WO 9  550 ACTTGCGTGAACACGGCAGGCAGCTTCGAGTGCAAGTGCGACGCCGGTTT  599
            *****  ****  **  **  *******  *******     ******  *  **  *

230  1050 CAGCGGAAATGCAACTGCAGACAGCCCTTGCAAGAACATTGACGAATGCG 1099
WO 9  600 CAGTGGCAGTGCTACTTCTGAGAGTCCTTGCTCGAATATAGACGAGTGCC  649
            ***  **  *  ***  ***  *  **  **  ******  ***  **  *****  ***

230  1100 CCAACCCAACGCCTGCTCGGCCAACGCTATCTGCACAGACACCGACGGC 1149
WO 9  650 AAGACCCGGATGCCTGCTCAGCCAACGCAATCTGCGCAGACACTGAGGGC  699
            ****  *  *********  ********  ******  *******  **  ***

230  1150 TCCTTCACCTGCAGCTGCCCCGAAGGGTACAGCGGCCAGGGAACCCATGA 1199
```

FIGURE 12 (CONT.)

```
WO 9   700  TCTTTCACTTGCAGCTGCCCTGAGGGTTACAGCGGTGGGGATCACACGA  749
            **  *****  ************  **  **  ********    ****  *  **  **

230   1200  CTCTCCCTGCTCCAAGATCGACTTCTGCGCATACCCCTCACTCAATACAT  1249
WO 9   750  CTCTCCTTGCTCGAAGATAGATTACTGCGCCGACCCCACACTGAACACCT   799
            ******  *****  *****  **  *  ******  *****  ****  **  **  *

230   1250  GCGGAGCCCACTCCACTTGC---AACACCCTCACATCTTTCAAGTGCATC  1296
WO 9   800  GCGGGGCCCACTCGACTTGTGTGAACACACTAACGACGTTCAAGTGCGTT   849
            ****  ********  *****    *****  **  **  *  *********  *

230   1297  TGCGATGCGGGATATGAAGGCGCCGGCACTCGCGAGAGCCCGTGCCGTGGA  1346
WO 9   850  TGCGATGCCGGTTATGACGGCCCGGGAACGCACGAGAGCCCTTGTGTGGA   899
            ********  **  *****  *****  **  **  *  *********  **  *****

230   1347  CGTGAACGAGTGCTCGAACGAGAAGCCCACAAACAACTGCAACAGAAACG  1396
WO 9   900  TATCGACGAGTGCTCCAAGGAGAAACCATCCAATGACTGCAACCGAAACG   949
             *  **********  **  *****  **  *  **  ********  ******

230   1397  CAAACTGCACCAACACCGAGGGATCCTACACTTGCGAATGCAAGCCCGGT  1446
WO 9   950  CCGTTTGCACAAATACTGAGGGATCGTACACCTGCGCATGCAAGGAAGGC   999
             *    *****  **  **  ********  *****  ****  *******    **

230   1447  TTCTCTGGCGACGGCATGGGTCCCAACGGGTGTACCGACATCGACGAGTG  1496
WO 9  1000  TTCTCTGGCGAGGGTTTCGGAGCTGCAGGGTGTGCAGATGTCGATGAGTG  1049
            **********  **  *  **  *    *****  *  **  ****  *****

230   1497  CGCGGCCGAGCCAGTCCCCCTGCGACCCTCACGCCTCCTGCAGCAACACTG  1546
WO 9  1050  CGCGA------ATTCGCCCTGCGACGCCCACGCCTCTTGTGCCAACACCG  1093
            ****        *  **  ********  *  ********  **  ******  *

230   1547  AGGGCTCGTATGTATGCACCTGCAACACCGGCTACGAGCCAGCTTCAACC  1596
WO 9  1094  AGGGTTCCTACGTTTGCACTTGCAACCCTGGCTATGAACCAGCCTCAAGC  1143
            ****  **  **  **  *****  ******  *  *****  **  *****  ****  *

230   1597  GACGGGCATGCATGCAAAGATATCGACGAGTGCGCCACCGGTGCAGCTGG  1646
WO 9  1144  GACGGACATGCATGCAAGGACGTTGACGAGTGTGCAGCGGGCACGGCGGA  1193
            *****  ***********  **  *  ********  **  *  **    *  **  *

230   1647  GTGCCACGTGTCAGCACAGTGTCTGAACACGGACGGCAGCTACGAGTGCA  1696
WO 9  1194  ATGCCACGTCTCCGCACAGTGTGTGAACGTGGATGGCAGCTATGAATGCC  1243
             ********  **  *********  *****  ***  ********  **  ***

230   1697  AGTGTCTTGAGGGCTTCGTCGGCGACGGAAAGACCTGCAACGACGTCGAT  1746
WO 9  1244  ACTGCTTGGAAGGTTTCATTGGCGACGGAAAGGTGTGCAGTGACGTTGAC  1293
            *  **  *  **  **  **  ***  *  *************    ****    *****  **

230   1747  GAGTGCGCTGCGGCGACATCTCCTTGCGGTGACAACACTCACTGCCAGAA  1796
WO 9  1294  GAGTGTGCGGCTGAGGCTTCGCCCTGTGGCGCAAACACGCATTGCCTGAA  1343
            *****  **  **  *  *  *  **  **  **  **  *****  **  ****  ***

230   1797  CACAATGGCAGCTACGAGTGCGAGTGCAAGGCTGGCTATGGCAACATGC  1846
WO 9  1344  CACCATGGCAGCTACGAGTGCGAGTGCAAGGACGGATATGGCCACATGG  1393
            ***  **  ************************  **  ******  *****

230   1847  AAGACAACGCATGCAGCGACATTGACGAGTGCAAGCATGCGAACACCAAG  1896
WO 9  1394  AGGGCAACGCGTGCAGCGACATCGATGAGTGCCTCAGAGGCGTCTACAGAG  1443
```

FIGURE 12 (CONT.)

```
                  *  *  ******  ***********  **  ******    **  ***    **  **
230   1897  ATCCCTGACAACTGTCTTTGCGTGAACAATGATGGCAGCTACTCCCTTGA  1946
WO 9  1444  ATCCCAGAGAACTGCAACTGTGTCAACACCGAGGGGAGCTTCTCCCTTGA  1493
                  *****  **  *****    **  **  ****  **  **  ****  ************

230   1947  GGCGAAGGCTGGATACGAATTGGTGAACGGCGAGTGCATCAAGATCGACT  1996
WO 9  1494  GGCAAAGCCTGGGTACGAGCTCGTCGACGGCAAGTGCGTCAAGATCGACT  1543
                  ***  ***  ****  *****    *  **    *****  *****  ****************

230   1997  TCTGCGCCCGCGGCGCATGCAACTCGCTGGCCTCCTGCAAGGAGAATCAA  2046
WO 9  1544  TCTGCGCCCGTGGTGCATGCAACTCGCTGGCGCACTGCAAGGAGAATCCC  1593
                  **********  **  *****************    *************

230   2047  GAAGGCACAGCGGCGATCTGCACCTGCCTGCCAGGCTACAGCGGCGACGG  2096
WO 9  1594  GAGGGCACCGCGGCGATCTGCACTTGCATAGCTGGCTATTCAGGTGACGG  1643
                  **  *****  *************  ***  *  *  *****    **  *****

230   2097  CACTGCTGAAGGCCACTGCAACGACATTGACGAGTGTGCAGGTCAGAATG  2146
WO 9  1644  CACAGCTCAGGGCCACTGCGATGACATCGATGAGTGCTTGGCGGAGAATC  1693
                  ***  ***  *  *********  *  *****  **  *****    *  ******

230   2147  ACTGTGCTCCTGCCGAGCAGGGAGGCATCTGCGAGAACACTGTCGGCTCG  2196
WO 9  1694  ACTGCACCCCTGCCGATCAAGGAGGGATTTGCGAGAACACTGTCGGCTCT  1743
                  ****  *  *********  **  *****  **  ***********************

230   2197  TACACCTGCAAGTGCAAAGAGGGGTACAGGCAAGATGGAAACTCATGCAC  2246
WO 9  1744  TACACCTGCAAATGCGCAGCTGGGTACCAGCAAGACGGCAACTCATGCAC  1793
                  ***********  ***  **  *****  *****  **  ***********

230   2247  TGAGATCGACGAGTGCGCTGAGGGAACCCACAACTGCCACCCTTCCGCCA  2296
WO 9  1794  TGACATTGACGAGTGCGCCAACGGCACTCACAACTGCCATGCCTCCGCGA  1843
                  ***  **  ************  *  **  **  **  *********  *  *****  *

230   2297  CCTGCAGCAACACCCCCGGAAGCTTCACCTGCCAATGCAACAGTGGATTC  2346
WO 9  1844  CATGCACGAACACGCAAGGCTCCTTTGAGTGCGCCTGCAACGCAGGCTTC  1893
                  *  ****  *****  *  **  ***  ***  ******  **  ***

230   2347  ACTGGCAGCGGTGTGGAGTGCGAAGACATTGACGAGTGCTCAACTGAGGC  2396
WO 9  1894  AGCGGCAACGGGGGTTGAATGCAACGACGTCGACGAGTGCTCGACTGACGC  1943
                  *  ****  ***  **  **  ***  *  ***  *  ***************  *****  **

230   2397  AGATGATTGTGGTGCAAACACCATCTGCAGCAACACCATTGGTGCTTTCG  2446
WO 9  1944  TGACGATTGCGGAGAGAACACACTGTGCAACAACACAGTTGGCAGCTTCG  1993
                  **  *****  **  *  *****  *  ****  ******  ****    ****

230   2447  AGTGCAACTGCCGTGAAGGCTATGAACGCGCAGACGCAAAGACGTGCGTC  2496
WO 9  1994  AGTGCACATGCATGGCTGGCTTCGAGGCCGCGGACGCGAAGACCTGCAAA  2043
                  ******  ***    *  ****  **    ***  *****  ****  ***

230   2497  GACATCGACGAATGCGCGACAGGCACACACACTTGCTCGAACCACGCCAC  2546
WO 9  2044  GACATCGACGAATGTGCAAGCGGGACCCACACTTGCTCCACCCACGCGAC  2093
                  **************  **  *    **  **  *************  *  ******  **

230   2547  CTGCACCAATACCGATGGGTCATTCACATGCCAGTGCAACCCCGGCTTCG  2596
WO 9  2094  ATGCACCAACACTGCTGGGTCGTTCACATGTGAGTGCAACCCAGGCTTTG  2143
                  ********  **  *  ******  ********    *********  *****  *
```

FIGURE 12 (CONT.)

```
230   2597  AAGGTGACGGCCACAAGTGCGAGGACATCGACTTCTGCGGTGCTGGACAG  2646
WO 9  2144  ACGGTGACGGCCACAAGTGCGAGGACGTGGACTTCTGCGGCCAGGGGCTG  2193
            * *******  *********** ****  * ***********   ** * *

230   2647  CACGACTGCAATGTGCATGCCGAGTGCTCTGAGAGCGAGGACAACACCAC  2696
WO 9  2194  CACGACTGCAACGTGCATGCAGAGTGCTCGGAAAGCGACGACAACACCAC  2243
            *********** ******** ******** **  ***** **********

230   2697  TTTCAAGTGCACCTGTATAACAGGGTACGCTGGAGACGGCCATGGCGAGG  2746
WO 9  2244  CTTCAAGTGCACCTGCGGCATTGGGTACAGCGGGGAAGGCCACGGGGAGA  2293
             **************    *  ****** ** **  *****  ** ** *

230   2747  CAGGCTGCCAAGACATTGATGAGTGCGCAGAAGAAAACATCTGCGGAAGC  2796
WO 9  2294  ATGGTTGCCAAGACATTGATGAGTGCGCCAAGATGCCATCTGTGGGGAG   2343
            **  ************************   **  ******* **  * *

230   2797  AACGCTGTCTGCACAAACACCGCAGGAAGCTACCAATGCGCATGCCGTGA  2846
WO 9  2344  AACACAGTGTGTACCAACACACCAGGTAGCTTTGAATGTGCGTGTGTGGA  2393
            *** *  ** **    ***  ** **  ****    *****  ** **   **

230   2847  GGGCTTCGTTGCATCAGCTGAACAGCAGCAGCAGGGAACCCAGCACTGG   2896
WO 9  2394  AGGGTTCGTGG---CTGTGGGAGCGAAGCTCAAGGGAGCAACTTCATTGA  2440
             ** *****      *  *  *** * **     *****       ** **

230   2897  TTTGCGTGGACGTCGACGAGTGCAGCGACGCTTCGAAGAACACATGTGCC  2946
WO 9  2441  CCTGCATAGACATCGATGAATGCAACGACGCCTCGAAAAACACTTGCGCC  2490
             *** *  *** ****  ** ***  ****** *****  ***** ** ***

230   2947  AAGCCAGCCGACGGAGGCATTTGCACAAACACTGAAGGCAGCTACGAATG  2996
WO 9  2491  ACGTCAGCTGACGGAGGCTCTTGCAAGAACACCGCAGGCAGCTATGAGTG  2540
            *   ****  ********  ****     *****   ** *** ** **

230   2997  CGCTTGCAAGCCAGGCTACCAAGGTGACGGCCACAGCTGCGCAGACATCA  3046
WO 9  2541  CTCGTGTTTGCCTGGGTTCCAGGGCGACGGCCACAGCTGCACAGATATTG  2590
            *  *  **   **   ** **   ** ****************  *** *

230   3047  ACGAATGCACTGCACAGGGCACCTGCGGCGAACACACAACTTGCAAGAAC  3096
WO 9  2591  ATGAGTGCGCCACCCAAGGCGTATGCGGGAACATGCGACCTGCGAAAAC   2640
            * ** ***     *   *  **   ****    * *  ** ***   **

230   3097  ACACCCGGATCCTTCCAGTGCGACTGCGTTGAGGGATTCG---AGCGCGC  3143
WO 9  2641  ACTGCGGGTTCGTACAATTGCACCTGCGAGGCGGGTTACACTCAGCAAGA  2690
            ** *  ** **    **  ****  **** *    *   * **     * *  *

230   3144  TGATGAACGCACCTGCCGTGACATCAACGAGTGCGAGACAGGAGCAGTCG  3193
WO 9  2691  TGGGGCCGTCGGCTGCATTGATATTGATGAGTGTGCAGCCTCCACAGCAG  2740
            **   *    *    *** ***  **    ******       *** *

230   3194  TGCTGCCACCGAACTCCACCTGCCGTCAACACTGAAGGCAGCTACGACTTC  3243
WO 9  2741  TGTTACCCGCCAACGCCACTTGCCGTGAACACTGAAGGCAGCTATACATTC  2790
            ** *  ** *  ***  **** *****  *****************    ***

230   3244  GACTGCCGTTGCTGGGTACCGCCGCACTGATGGAGCTTGTGTGAAGATCGA  3293
WO 9  2791  GAATGCGTGCCCGGCTACCGCCATACCGGAGAATGGCTGTACCAAGATTGA  2840
            ** *****   *  *******   **  *   *****  ***** **
```

FIGURE 12 (CONT.)

```
230  3294 CTTCTGCAAGGAGAAGGGATGCAACGCAAACGCCACATGCCGCGAAAACG 3343
WO 9 2841 TTTCTGCAGCGAAAAGGGATGCAATGCGAATGCCAGCTGCAAGGAGAACG 2890
          ******  ** **********  ** **  ****  ***    **  ****

230  3344 ATGCCGGCACCGAGGCCATCTGCACTTGCAAGGAAGGCTATGAAGGCAGC 3393
WO 9 2891 ATGCCGGCACCGAAGCCATCTGCACCTGCCACAGCGGGTACGAGGGCAAT 2940
          ****  ********  ********  ****  ***  *  ** ** ** ****

230  3394 GGAGAAGGCGAAGATGGTTGCCAGAACATCAATGAGTGCGAGAGAGGCGA 3443
WO 9 2941 GGCGAAGGAGAAGAAGGGTGCAAAAACATTGACGAGTGCTCCGTGGGAGA 2990
          **  *****  *****  **  ***  *  *****    *  ******        **  **

230  3444 ACCCTGCAAGGACTTCGGCGAAGGCGGTGTTTGCGTCGACACACCAGGAT 3493
WO 9 2991 GCCATGCAAAGACTTCGGCGAGGGCGGCGTCTGTGTCGATTCTCCGGGAT 3040
          **  *****  *********  ******  **   **  *****  *  **  ****

230  3494 CATTCACTTGCGAGTGCGCTGCTGGATTCATTCAACGCCGCTCCGTTTGC 3543
WO 9 3041 CCTTCAGCTGCTCTTGCGCCACCGGTTTTATCAAGAGGCGATCTACTTGC 3090
          *  ****  ***   *****  *  **  **  **   *  *  **  **         ****

230  3544 CAAGATGTTGACGAATGTCTCGACGGAAAGCTGAACACCTGCGCTGCCAC 3593
WO 9 3091 CAGGACATAGATGAGTGCCTCGACGGAAAGATGAACACTTGCGCCCCCGT 3140
          **  **    *  **  **  **  ****************  ******  *****  **

230  3594 CGGAGGCGTCTGCTCCAACACCGTCGGTTCCTTCACCTGCTCGTGCGCCA 3643
WO 9 3141 CGGGGGTATCTGCACGAACACCGTCGGCTCCTTCACCTGCTCTTGCCGCTG 3190
          ***  **    *****  *  ********  ********************    *****

230  3644 GCGGCTTCGAAGGCGATGGCCACACCTGCAATGATGTCGACGAATGCGCA 3693
WO 9 3191 CTGGCTTCACGGGTGACGGCCTTACTTGCGAGGACATCGACGAATGTGCT 3240
          ******   **  **  ****   **  ***  *  **  **********  **

230  3694 ACAGCACAGCACACCTGTGACCCGAATGCCACTTGCGTCAACACCGAAGG 3743
WO 9 3241 ACGGCGGCACACACGTGCGACCCCAACGCCACCTGTGTCAACACTGTCGG 3290
          **  **    ***** **  *****  *****  ****  **  ******* *    **

230  3744 CAGCTTCGAGTGCCGCTGCAATGCCGGATTCGAGGGCGACGGACACACCT 3793
WO 9 3291 CAGCTTCGAATGCGGGATGCAAGGAGGGATTCTCTGGTGACGGCCACACAT 3340
          ********  ***  *  *****  *    *****       **  *****  *****  *

230  3794 GCGCAGACATCGACGAATGCGCAGACCCAGCCAAAAACACATGCGATACA 3843
WO 9 3341 GCACCGATATCGACGAATGCGCTGACCCTAACCTTAACAAATGCGACACA 3390
          **  *  **  *************************  *****    ****  ******  ***

230  3844 CACAAGGGTGTATGCCAAAACACCACAGGGTCCTACACCTGCGGCTGCAA 3893
WO 9 3391 CACAAGGGCATCTGCCAGAACGGCACTGGATCCTACACTTGCGGATGCAG 3440
          ********  *  *****  ***  ***  **  ********  ******  ****

230  3894 GACCGGATTCAGTCTTGCAGCTGACGGAAGCACATGCGAAAACGTCGACG 3943
WO 9 3441 GCCTGGATACAGTCTGGCGGCGCGACGGCTTCACTTGCGACAATGTCGATG 3490
          *  *  ****  *****  **  **  *****    ***  *****  **  *****  *

230  3944 AGTGCGCGGCGGGAACTGCAAACTGCAACGAGCGAAGCTTCTGTAAGGAC 3993
WO 9 3491 AGTGCGCTGCCGGGACGGCCACTTGCGGAGAGCGCAGCTTCTGCGTGGAC 3540
          *******  **  ****  *****  *    **     ****  *********    ****

230  3994 ACAGAGGGTTCCTACCAATGCGAGTGCAAGAACGGCTACAAGGCTGCAGG 4043
```

FIGURE 12 (CONT.)

```
WO 9  3541 ACGCAAGGGTCATACAAGTGCGAGTGCAAGAACGGCTACCGCCAGTCTGG 3590
           **  *  **  **  ***  *  *****************  *****   *  **

230   4044 AGAGGACTGTGTGGACGTTGACGAGTCCCAGCCTGGCGTGCATGGATGCA 4093
WO 9  3591 GGAGGACTGCGTGGACGTTGACGAGTGCGAGCCTCATGTGCACACATGCA 3640
           *******  *****************  ***  ****  *****  *****

230   4094 GCGAGCACGCAATCTGCACAAATACAGACCGGCAGCTACTCCTGCGAATGC 4143
WO 9  3641 GCGAGCACGCTACGTGCACGAACACTGAGGGCAGCCACACCTGCACCTGC 3690
           ********** *  *****  **  **  **  ***  **  *****   ***

230   4144 ATGGAGGGATACCAGGGAGACGGCAAGGCTTGCGAGAAGACAGTCGGCGT 4193
WO 9  3691 AATGAAGGGTACCAGGGAGACGGAAAGAAGTGCGAGAAGACAGTGGGCCC 3740
           *  **  **  *************  ***  ************* ***

230   4194 CTGCGACTCCGCTCCCTGCGGTGCCCACGCCACCTGCGAGCCTGCAGGGG 4243
WO 9  3741 TTGCGACAACTCGCCATGCGGCAACAACGCCATGTGTGAAGCTACTGCCG 3790
           ******  *  *  **  *****  *  ******  **  **  **  *  *  *

230   4244 ACAACTACACTTGCACATGCCACCCAGGCTACGAGATGCGCGAAGGAGCC 4293
WO 9  3791 ATAGCTACAACTGCACTTGCAAAGCTGGCTACGAGATGAAGGACGGGGCC 3840
           *  *  ****  *****  ***  *  *  ***********  **  **  ***

230   4294 TGCGTTGACATCGATGAGTGCACAGCAGGCAGCCTCAACTCCGACCCTCA 4343
WO 9  3841 TGTGTCGACATCGATGAGTGCCAGTCGGGCACCCACAACTGCGACCCGCA 3890
           **  **  *****************   *  ****  **  ************  **

230   4344 TGCCATTTGCACAAACACCGACGGCTCCTTCACTTGCGTCTGTGGCAGCG 4393
WO 9  3891 TGCTGACTGCAGCAACACCGATGGATCCTTCACGTGCACGTGCGGTTCTG 3940
           ***   ****  ********  **  *******  ***  **  **   *

230   4394 GCTATACCGGCCTTGGCACATCCTGCGAAGACATCGACGAGTGCGCGGGT 4443
WO 9  3941 GCTACACTGGTGTGTGGGTACCCTTTGCGAGGATGTGGACGAGTGCGCGGGC 3990
           ****  **  **  *  **  **      *****  **  *  *************

230   4444 AACGCAGCAGGCTGCGACATCCACGCCGTCTGCACGAACACTCCCGGGATC 4493
WO 9  3991 AACCATGCGGGCTGTGACATCAACGCTGTTTGCACTAACGTCCCTGGCTC 4040
           ***   **  *****  *******  ***  **  ****  *****  ***   **  **  **

230   4494 GTTCAAGTGCGAGTGCAAGAGCGGCTTCGAAGGCGATGCCACGCAATGCA 4543
WO 9  4041 GTTCACTTGCGAGTGCAAGAGTGGCTTCGAAGGCGATGGGCACGAGTGTA 4090
           *****  ************** ****************** *  **  *

230   4544 CGGAGAAGGTGTTGCTCCCCGGACAGATTCACTGCGAAGCCTGGACTGCA 4593
WO 9  4091 CGGAGAAAGTGCTGCTCCCTGGCCAGATTCACTGCGATTCGTGGACTGCA 4140
           *******  ***  ******  **  *************  *  ********

230   4594 TGGACAGAGTGTACCGACGGCGCCAAAACCAGCACACGCAGCTGCCTTGC 4643
WO 9  4141 TGGACCGAATGTACAGCTGAAACTAAGCAGAGCACCCGCAAGTGCGTGGC 4190
           *****  **  *****  *  *  *  **  *****  ****  ***  *  **

230   4644 ACTGCCGCTTAAGAAGGAGATGCGCGCCTGCCCTGCAGCTGACTTCTCCC 4693
WO 9  4191 TCTTCCTCTCAAGGTCGAGGTGAAGCTTTGCCCCGATGCTGACATTTCAG 4240
           **  **  **  ***  ***  **       *****  *  ******  *  **

230   4694 AGTGCGGAGAGTTCACTGAATGGACTGCCTGCCCTGGAACCAACAATAAC 4743
WO 9  4241 CCTGCGGTGAACTCGGCGAGTGGTCATCATGCCCAGGAGTTGACAACAAC 4290
```

FIGURE 12 (CONT.)

```
          ***** **   **      ** ***   *   *  *****  ***        ****  ***
230  4744 CTGTCTCATAGGCGCACTGAAAGATTCGGAGAACCCGGATGCGAAGATGC 4793
WO 9 4291 CTGTCGCACCGCAGAGCAGAGAAGTTCGGGGAGCCGGCTGTGAGCACGC  4340
          ****  **   *      *  **  *    *****  **  **  **  **  **    *  **

230  4794 AGAGGAAGTCCGCGAATGCCCAGATGAAGAGACCGAGCAGAAATGCGGCG 4843
WO 9 4341 TGAGGAGGTCAGGCAGTGCCCAGATGAAGAAGTTGAGGAGCGCTGTGGTG 4390
          *****  ***  *  **  ****************    ***  **    **  **  *

230  4844 CCTGGGGTGAGTGGACCGCCTGCGGCGACCCATCCCTGGCCTGAGAACT  4893
WO 9 4391 CCTTTGGCGAGTGGACTGCATGCGGCGATCCTTCTGAGGGCTTGAGGACC  4440
          ***   **  ********  **  *******  **  **        ***  ****  **

230  4894 CGCGCACGCGAGAACTGCCCCGATGTGGTAGAGTTCGAGCGTTGCACTAT 4943
WO 9 4441 AGGACGCGCCAGAACTGCCCAGAAGAGGCAGAATTCGAGCACTGCACAAT 4490
          *   *  ***  **********  **  *  **  ***  *******  *****  **

230  4944 GCCCAGTGAGCCTGAGGCTGGCGAAGTGACTGAGCCTCACACAGAAGGAG 4993
WO 9 4491 GCCCTCTGCACCATCCGTTCCCGAGGGCGGCAGCAGCTGCACACAGTTCG 4540
          ****  **  **      *  *  ***  *                    ******         *

230  4994 GAGCCGGAGTTGGTGGCGAAGTGACTGAGCCTGACACGGAAGAAGGAGCC 5043
WO 9 4541 GGGCCTGGAGTGAATGCG---TGGCTGACGCT--CATGGGATCAAGATGC 4585
          *  ***  *      **    ***    **  ****  **  **  **  *    *  **  *

230  5044 GGAGTTGGTGGTGAAGTGCAGCCCGGTACAGAAGAAGGAGCAGGAGTTGG 5093
WO 9 4586 AGCACAGAACGTGC-GTACACAATGAAGCTGTGCAGGAACACAGAATCTG 4634
          *       *   ***  **  **       *    *  *    ***         **  *   *

230  5094 TGGTGAAGTGCAGCCCGGTACAGAAGAAGGAGCCGGAGTTGGTGGTGAAG 5143
WO 9 4635 CACCGTGGAAGA-TCCACAACAGTGCGGGGAGTGGTCGCAGTGGTCAGAG 4683
          *    *    *    **   ****         ****   *    *    *       **

230  5144 TGCA-GCCCGGTACAGAAGAAGGAGCCGGAGTTGGTGGTGAAGTGCAGCC 5192
WO 9 4684 TGCAAGAATGGCAAGCAGTACAGAGGCGCCGCCGG-----ATCGCGTCT  4728
          ****  *     **  *    *    *    ***  **    *  **          *  *  **  *

230  5193 CGGTACGGAAGAAGGAGCCGGCATTGGTGGCGAAGTGACTGAGCCTGACA 5242
WO 9 4729 GTGTACG-AAGTCAGAGCCTGCAGCGGCG-------------CTAGCG  4762
          *****  ***    *****  ***    **  *                              **  *

230  5243 CCGAAGGAGGAGCCGGAGTTAGTG-GCGAACCGACCGAAGAAGAGGGCAC 5291
WO 9 4763 ATGCGAAAGAATGCTCTTTTGGTGCGTGGAGCGGCTGCGTGGTGGAGTTT 4812
          *      **  *    *          **  ***   *  *    **  *              *  *

230  5292 CGAAAGCACCGGTCCATGCAAAGAGTTCGGACCCTGGACGGCCTGCAAGG 5341
WO 9 4813 GGCGGTCAC-------ACTTACAAAGTGCGAAACTCAATCGAC-TGCGAGC 4855
          *    ***         *    *  ***  **  *  *       **  *  ***  **

230  5342 AGGACCAGAACGGAGTCGGCATCCAACGCCGTATGTCGCCGGCAGAGAA  5391
WO 9 4856 TCAGTGAGCT----GCAGGCTTGCAA-GCC----GAGCGCCGCCACCGAG 4896
          ***       *    ***  *  ***  ***        *  ******  **  **

230  5392 GACATCATCGAATCCAGAATTTGCACTGTCACGGATGACTGCGGAGAATG 5441
WO 9 4897 GGCGAGGGCAAGTGCGCTGCTTGGAGCCCCTCGACGATCTGCAGGGA--C 4944
          *  *    *****   ***  *      *  *        ****  *  **
```

FIGURE 12 (CONT.)

```
230   5442 GACCCCCTGGTCAACTTGCACTAACGGCAGCCAGGCCAGAAACAAACGCT 5491
WO 9  4945 GGCATGCAGACTCGCGACTGCAAAAGCCTGGGTGTTCAGGAGTCC-CGCC 4993
           *  *   * *    *   *  ** *  *   *   *** *      ***

230   5492 TCTGCACCAACGTTAGGGAAGTCCGTCTCTGCGGAGCTGACATTCCAGTT 5541
WO 9  4994 CATGCTCAGCTGAAGGAGAGACCGATTCTTGCGGAGCCTTTGGACCC-TT 5042
           *** *    *   *  ** *  *    *******         **  **

230   5542 ACAGACGGATGCACGTGGAGCGAGTGGACTTCTTGCAGTCTAGTCAATGA 5591
WO 9  5043 CGAGCCGGCAGCTTGCAAGGCTGGCGAGAATGGTCACGA---GGACGCGG 5089
           ** ***  **  *      **  *   *     *    *    *    *

230   5592 GGAGGGCGGCTACTTCCGCACGGCGCACATCCTCTGACTGCAACATGAATG 5641
WO 9  5090 AGTGCAACGGTGCT-CAGCAGAAGGAAACC---AGACTGTGCAATCC-TG 5134
            * *      *  **  *  ***  *  *     *****    **  **

230   5642 AAGTGCAGGCCTGCTCTCCCAGCAGCAGCACAACCGCAGACAGCGAAACA 5691
WO 9  5135 AGGGCAATGACAACTGCAACAACTGGGGTGCTTGGACAGAGTGCTCGCTA 5184
           * *    * * *     **   ** *  *  *     ****  **   *

230   5692 GAAGGCACCTGCTCTGCATGGAACCCCTGGACGGAGTGCTCGAACGGCCA 5741
WO 9  5185 ATTGTGGCGGCTCTGCCCTGCGGTCTCGCGAGGAGTCCACTTGCGGCTA 5234
            *  *   ******   *  * *  *  * ****  *    **** *

230   5742 CCAGACACGCAAGTGTGCCACAATGGAAGCAGAAGAATCGCGCACTTGCG 5791
WO 9  5235 TGTGGA--GTTAGAGGAGTGCAGTGGCAGCAGCAGCAGCGGCGACCAGAC 5282
             *  *    *  **  **  ****  ***  ***  **  *   *   *

230   5792 GAGAGACTCCAGAGAACTGCGGAGAATTCGGCCCCTTCGAACCCGCAAAC 5841
WO 9  5283 CGTCCACTGCGGC-AGCTGGTCGGAGT---GCTCCATGAGAAAAACGGAG 5328
             *  *** * *   ** *   **  *       **  *    *    *

230   5842 TGCACGGCCGGCCAAATGGTCACCAGGACGCGCACCTGCGGAGAAACCGA 5891
WO 9  5329 CGCACCTGTGATGTCCTCTCTGACGGATCCCACCACCAGCGTTACTGAAGT 5378
            ****   *  *   *  * *   **** *** ***   *        *

230   5892 GCAGAAGGAAACCAAACTGTGCCGACGTCAGCTCCACCGAAGAAGGAAAAC 5941
WO 9  5379 GCTCACCTGCGACGACGTGCTGCCTGACTCTTGCGGTGAATTTGGCGAGT 5428
           **  *        *  **   *    *   *  *   ***    **  *

230   5942 AATGCGGTCAGTGGGCCCATGGAGCGAATGCAACATCCACCTGGGCTCA 5991
WO 9  5429 GGTCCGAAT-GTAGCGCTGACGGCTTGCACTCGAGGTCCCTGTCAGGCTG 5477
             * **    **  * **  * **   * **   *  *   *** *  *

230   5992 GAGGACAATGTGCGTGTTCGTGAGG-ACACCGCTTGCGGCGTGACGGAGT 6040
WO 9  5478 CCCAGACGTAACTGAAGTGATGACTTGCGGCAGCGAAAACTGCCCGGCTT 5527
               *  *  *   *   ***  *  *        *    *  ***  *

230   6041 ACGAGGAGTGCAGCAAGC-CGGCGAACAACGCCTTTGTCTGCACACCTTG 6089
WO 9  5528 TCGGCGAGTGGAGCGAGTGCGGCAGCCCAGAGGACGGCCTACGGTCGCGT 5577
            **  ***** *** ** **  ****  *  *      *  **  *  *

230   6090 GAGTGAAATGCTCGGACAAGAAGGAGCGGAGAACGTGCACCATCCGCAAA 6139
WO 9  5578 CAGCGAACGAACTGCGAAGAGGGATCCGGCTGCATTTGC--TCCGAGACA 5625
           ** ***   *  *  **  ****  **  *    * *  *  **** * *
```

FIGURE 12 (CONT.)

```
230  6140 ACGGTCT-TGTTCAGACACGTCAAGAATTCAGAACATGCAGTGTAGACAT 6188
WO 9 5626 GAAGCCTGTGTTAACACTGAGCTCCACCCCATCCCATTGCCAGTTCCTGG 5675
          *  ** ****  *  **    *   *     **  ***       **

230  6189 CGCCACAACTTGCGGCGATTTCGGCGCA---TGGTCTGAATGCAACGCTGA 6236
WO 9 5676 CGGCCGCGAGGGCAGCGAGAACCCCGAGGGTGGCCAAACGGAGAGGAGG   5725
          ** *        **  ****   *****    *** *   *  *  *  *

230  6237 GGGCTTGCATCAGCGCAGTCT-CGAGAAATGCCCCGACGTCATCGAGGTC 6285
WO 9 5726 GAACGGAGGGAGGCGCAGGCGGTGCTGGAGGATCCGGTGGTGCTGAGGA- 5774
          *  *       ****** *    *    * *  ***   *    ****

230  6286 GCAACTTGCGGCAGTGAGGATTGCCCGCCATTCGGCGAGTGGACTGAATG 6335
WO 9 5775 GCTGCC--CGGAGAAGAGGGTGGCGCAGGTGCCGGCGGAGAAGGAGGCTC 5822
          ** *    ***    **** * ** *      *****        *  *

230  6336 CGGCGTTCCAGAGGAGGGCATGCGTTCTCGCCAACGCATTGACTGCGTTG 6385
WO 9 5823 TGGCGGTAATGCTGAGGAGCTGC---CCGGAGAAGGGGGTGCTGGCG--- 5866
          **** *    *   ****   **  *         *  *     **   ***

230  6386 AATCTGCAGCCTGCCAGTGCACAGAAGTGGAGAGCTGCTTCGACACCGAA 6435
WO 9 5867 AAGCTGGAGGCT-CTGGCG-GTAGTGCTGAGGAGCTGC------CCGGA  5907
          ** ***  **  **  *   * * *  **   ** ** *******    *** *

230  6436 TTGCACCCCATTCCAGCCCCCGGTACGGAAACAGGCGAAGGAGAGGGAGA 6485
WO 9 5908 GAAGAGGGCGGCGCAGGTGCCGGCGGAGGAGGAGGCTCTGGCGGTAGTGC 5957
          *      *     ***    ****   *  *  ****   **  *    * *

230  6486 GACCGAGACAGGCGAAGGCGAAACTGGTGAAGCACGTGGCGAGGAAGGCG 6535
WO 9 5958 TGAGGAGCTGCCTGGAGAAGAGGGCGGCGCAGGTGCCGGCGGAGAAGGAG 6007
          ***       *  **   **  **  *  *  ****  *****  *

230  6536 AGCAAACAGGAGAAGGCGAAGTGCAGCCCCCAGAAGAAGAGCTTCCTGGG 6585
WO 9 6008 GCTCTGGCGGCAATGCTGAGGAGCTGCCCGGAGAAGAGGGCGGCGCAGGT 6057
          **  *  *   **   *  **  ****   ******  *       *  **

230  6586 GAGAGTGTAACTGAGCCTGAG---GAGAAGCCTGAGGAGGAGCTACCTGA 6632
WO 9 6058 GCTGGAGGAGCCGAAGGCGAGACAGGGAAACCTGGCGGCGAAGAGGGTGG 6107
          *   *   *  *  **   ***   *  *** ****  *  **       **

230  6633 GGAGGAGGTTACTGAGCCTGAGGAGAAGCCTGAGGAGGGTGTGACTCAGC 6682
WO 9 6108 CGCAGGCGGCGCTGGTGAGGGTGCTGGCGGTGAAGGTGGTGAGGTCCAGC 6157
          *  *  *   ***     *  *     *** *  ****  *     ****

230  6683 CTGAGGAGACACCTGAGCAGCCTGTTGAGGGTACCGAAGAAGAGGGCAAG 6732
WO 9 6158 CTGGAGAGGGAGAAGGGCGAGTGAAGGAGGCGAGCAAGTGCCGGAAACC  6207
          ***  ***  *   * *  *   **   *     ***   **  *

230  6733 CAGGAG---TCTGAGGCTG---CCCCCGAAAACT------CCTGCCGTCCA 6770
WO 9 6208 CCTGAGACACCCGAACCGGAAACACCTGAAGCTGAGAGACCTGAAGAGCA 6257
          *  ***    * **  * *    * **  *** **     ****   * **

230  6771 GCCAAAACCAGAGGA---GGGTCACGAACGCCCAGAACCCGAAGAGGAGG 6817
WO 9 6258 ACCCTCGACGGAAACTCCAGCAGAGCAGCCCACCGAAGGCGGTGCAGAAG 6307
          **  *   * **     *  ** * *  * ***  *   * **  *

230  6818 AGGAGAAGAAGGAAGAAGGCGGCGGCTTCCCAACAGCTGCAGTGGCAGGA 6867
```

FIGURE 12 (CONT.)

```
WO 9  6308  AAGAGGAGAAGGAGGAGGGCAGCGGCTTCCCCACGGCAGCTGTTGCCGGA  6357
            *  ***  *******  **  ***  **********  **  **  **  **  **  ***

230    6868  GGTGTTGGTGGTGTGTTGCTCATAGCTGCTGTAGGTGGTGGTGTTGCAGC  6917
WO 9  6358  GGTGTAGGTGGTGTGTACTACTGCTGGCAGCAGTGGGTGGTGGCGTTGCCGC  6407
            *****  *******  *  **  *  **  **  **  *********  *****  **

230    6918  CTTCACTAGCGGCGGAGGTGGCGGCTGGCGCACAGGAGGCAGAACAGGTCG  6967
WO 9  6408  GTACTCCGGTGGTGGTGGAGGTGGCGGTGCCGAGGAGGCTGAGCAAGTTG  6457
            *  *  *  *  **  **  **  **  *  **  **  ******  **  **  **  *

230    6968  AGTTCGAAGGAGAAGATACCGGAGCAGCAACTGCCGAGACACCTGAAGCC  7017
WO 9  6458  AGTTTGAAGGTGAAGAGTCGGGTGGTGCGTCTGCCGAAACACCTGAGGCT  6507
            ****  *****  *****  *  **  *  **  *******  *******  **

230    7018  GATACAGTTATCGACATCACAGACGAAGACGACTACTGGGCCGACAGCGG  7067
WO 9  6508  GATACTGTGATTGACATCACTGACGAAGACGACTACTGGCACACAGTGC  6557
            *****  **  **  ********  *******************  *****  **

230    7068  CGACATTCAG  7077
WO 9  6558  TGACATCCAG  6567
            *****  ***
```

FIGURE 13A

```
                    10                            30                               50
5' GTG GTG ATT GAA TCT GCT CCA GCC AAG ATG GCT CAC CCT CCT GTG GTG ATT GAG TCT GCT
   Val Val Ile Glu Ser Ala Pro Ala Lys Met Ala His Pro Pro Val Val Ile Glu Ser Ala 70                            90                              110
CCG GTC GAG GTG GTC CAT CCT CCT ATG GTG ATT GAA TCT GCT CCA CCC AAG ATG GCT CAA
Pro Val Glu Val Val His Pro Pro Met Val Ile Glu Ser Ala Pro Pro Lys Met Ala Gln 130                           150                              170
CCT CCG ATG GTG ATT GAG TCT GCT CCA CCC AAG ATG GCT CAA CCA CCT ATG GTG ATT GAG
Pro Pro Met Val Ile Glu Ser Ala Pro Pro Lys Met Ala Gln Pro Pro Met Val Ile Glu 190                           210                              230
TCG GCT CCC GTC GAG GTG GTC CAT CCT CCT ATG GTG ATG GAA GCC GCT CCC ACC GTG AAG
Ser Ala Pro Val Glu Val Val His Pro Pro Met Val Met Glu Ala Ala Pro Thr Val Lys

GGA AGA TAC CTC GCT GCT GAG GAT GAG GTG GAA GAG CAG TTT GAA TCG AAC AG 3'
Gly Arg Tyr Leu Ala Ala Glu Asp Glu Val Glu Glu Gln Phe Glu Ser Asn
```

Nucleic acid sequence of the first 293 nucleotides of clone pEM 250/14.
Note the presence of a 14 amino acid repetitive sequence in the single translated open reading frame.

FIGURE 13B

```
                10                    30                         50
5' C CTG CAG GTT GTA CTA AGA GCG CTT TAT GAC TAT CGG GAG CTC AAA TGC GGC TCA GCA TGC
    Leu Gln Val Val Leu Arg Ala Leu Tyr Asp Tyr Arg Glu Leu Lys Cys Gly Ser Ala Cys 70                     90                        110
CGG AAC GTG GGC ATT TTG GTA CAC GGA GGT ATC ACC TCG AGC GAA TGG GCG GGG GTC TTT
Arg Asn Val Gly Ile Leu Val His Gly Gly Ile Thr Ser Ser Glu Trp Ala Gly Val Phe 130                    150                        170
CCG CAA ACA AGC GTT CCA CCA AAA CCT AAG GTG GAA AAC TGT TCA GTT GCA TTT AAT TAC
Pro Gln Thr Ser Val Pro Pro Lys Pro Lys Val Glu Asn Cys Ser Val Ala Phe Asn Tyr

190
GCT TTT GTA AAT ACC 3'
Ala Phe Val Asn Thr
```

Nucleic Acid sequence of the last 196 nucleotides of clone pEM 250/14. The single open reading frame is translated into the amino acid sequence shown below the nucleotide sequence. A potential N-linked glycosylation site (Asn-Cys-Ser) is underlined.

FIGURE 15

```
CGAATTGCACCCCATTCCAGCCCCCGGTACGGAAACAGGCGAAGGAGAGGGAGAGACCGAGACAGGCGAAGGCGAAACTGGTGAAG    6750
   E  L  H  P  I  P  A  P  G  T  E  T  G  E  G  E  G  E  T  E  T  G  E  G  E  T  G  E      2173

CAGGTGGCGAGGAAGGCGAGCAAACAGGAGAAGGCGAAGTGCAGCCCCAGAAGAAGAGCTTCCTGGGGAGAGTGTAACTGAGCCTGAGG   6840
 A  G  G  E  E  G  E  Q  T  G  E  G  E  V  Q  P  P  E  E  E  L  P  G  E  S  V  T  E  P  E   2203

AGAAGCCTGAGGAGGAGCTACCTGAGGAGGAGGTTACTGAGCCTGAGGAGAAGCCTGAGGAGGGTGTGACTCAGCCTGAGGAGACACCTG  6930
 E  K  P  E  E  E  L  P  E  E  E  V  T  E  P  E  E  K  P  E  E  G  V  T  Q  P  E  E  T  P   2233

AGCAGCCTGTTGAGGGTACCGAAGAAGAGGGCAAGCAGGAGTCTGAGGCTGCCCCCGAAACTCCTGCCGTCCAGCCAAAACCAGAGGAGG  7020
 E  Q  P  V  E  G  T  E  E  E  G  K  Q  E  S  E  A  A  P  E  T  P  A  V  Q  P  K  P  E  E   2263

GTCACGAACGCCCAGAACCCGAAGAGGAGGAGGAGAAGAAGGAAGAAGGCGGCGGCTTCCCAACAGCTGCAGTGGCAGGAGGTGTTGGTG  7110
 G  H  E  R  P  E  P  E  E  E  E  E  K  K  E  E  G  G  G  F  P  T  A  A  V  A  G  G  V  G   2293

GTGTGTTGCTCATAGCTGCTGTAGGTGGTGGTGTTGCAGCCTTCACTAGCGGCGGAGGTGGCGCTGGCGCACAGGAGGCAGAACAGGTCG   7200
 G  V  L  L  I  A  A  V  G  G  G  V  A  A  F  T  S  G  G  G  G  A  G  A  Q  E  A  E  Q  V    2323

AGTTCGAAGGAGAAGATACCGGAGCAGCAACTGCCGAGACACCTGAAGCCGATACAGTTATCGACATCACAGACGAAGACGACTACTGGG  7290
 E  F  E  G  E  D  T  G  A  A  T  A  E  T  P  E  A  D  T  V  I  D  I  T  D  E  D  D  Y  W    2353

CCGACAGCGGCGACATTCAG
 A  D  S  G  D  I  Q
```

Figure 19
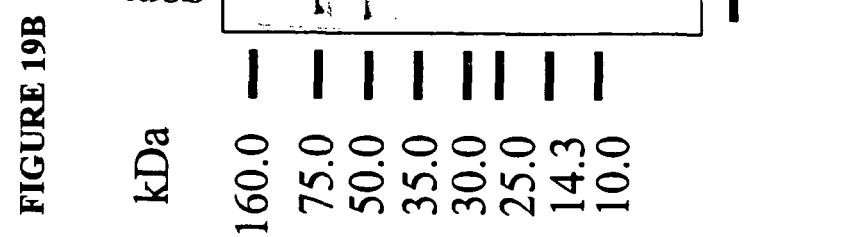
FIGURE 19A
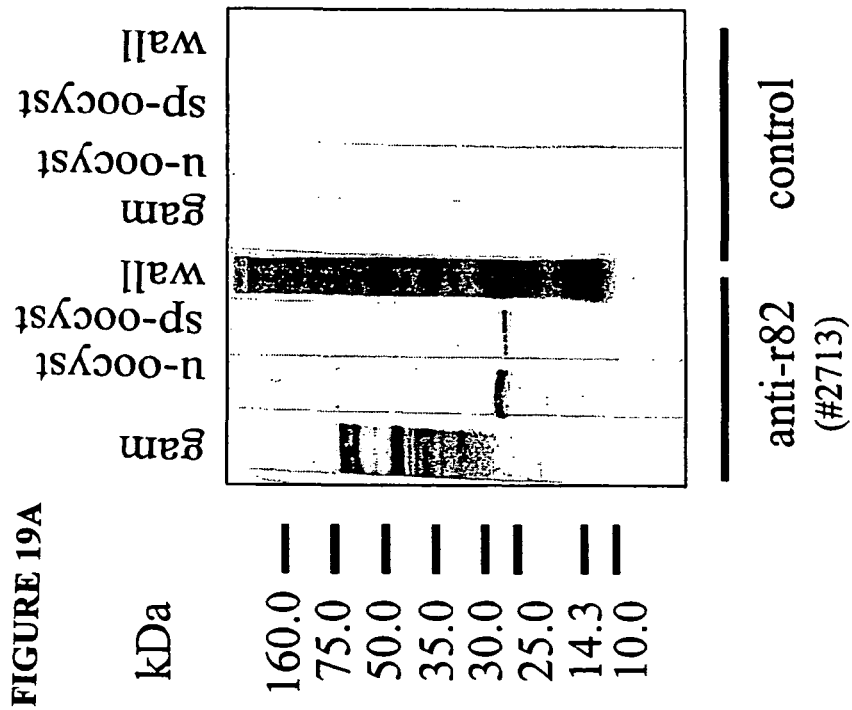
FIGURE 19B

FIGURE 20A

| | 21............35 |
|---|---|
| 56 kDa gametocyte protein (N-terminus) | VPSTTPVENQHVHPYS |
| ~30 kDa oocyst wall protein | VPSTTPVENQH-HPYS |

(this wall protein represents the low abundance protein recognized by anti-r56 kDa antibody)

| | 240...........254 |
|---|---|
| 56 kDa gametocyte protein (domain 1) | MGRKGRSFYYGGYPS |
| 14.1 oocyst wall protein | YGRKGRSFYYGGYPS<br>G |

FIGURE 20B

| | 418...........431 |
|---|---|
| 82 kDa gametocyte protein (domain 2) | YPSYSWSYPAYTRV |
| 14.2 oocyst wall protein | YPSYS-SYPAYTRV |

| | 282...........296 |
|---|---|
| 82 kDa gametocyte protein (domain 1) | GKRMYSTGYYGYGYP |
| 14.3 kDa oocyst wall protein | -KRMYSTGY-G---P |

FIGURE 20C

| 30 kDa oocyst wall protein | -SFSPVAPQELF--(L) |
|---|---|

(this protein represents the 30 kDa protein detected by coomassie blue staining of purified oocyst wall fragments)

SEQUENCE LISTING

<160> NUMBER OF SEQ ID NOS: 44

<210> SEQ ID NO 1
<211> LENGTH: 1754
<212> TYPE: DNA
<213> ORGANISM: Chicken

<400> SEQUENCE: 1

```
agcagaacat agggagttca tctgttcctt cttttcatca tttattcctc gtttctcacc      60
gttttatttt ttttgtgtaa ccctctccgc tgttgagtcc caatgacccg cctcggcctc     120
gctgctgtcg cgctggctct cgccgtgggc ccttccatgg cagtgcccag caccactcct     180
gtggagaatc aggttcaccc ttacagcgag atgagtacct accaggaggg gagtgccccg     240
ggggctccgg aggacaccac caccaccact acgtcgtccc ctgtttccga tggagccgag     300
cagtggcttg agagctttgt tcgtgctgtg cagcgccagc tgcagcttca ggaccaaatg     360
atgcgtcagc tcatgaggga cattcaggag tacctgagca ctgcgttcaa ctgggcagag     420
aaccagtcta ctgcctacac ccgtgttacc gagatgatgg acatgatctc aacagaatg     480
aatgcagcaa tggacagctc aaacgaactc atgaccacta gcgacaccac agaccccgag     540
accctccgcc gtgcaactcg caagtacatg aaggaggttc gcgttcagga cgtcctggta     600
gatgctctct gggcctctct ccgcggtgta cagacagctg cctggatgaa tggagtgacc     660
gctattgaga aggaggagac gactcccatg gctagccgcg ctgctgagga gttcctccac     720
cgcatgtacc ataacctgag ggcagcaggt atgtctgaag aagatgttgc caagttcatc     780
cctagagccg agtacaaccc ctccgagcag tcaagaaata tgggcagaaa gggcaggagc     840
ttctactacg gcggctatcc cagctactac aactccccct actacagcta cagcagctac     900
cccagctact acaactacag ctacccgtca tacagctaca gcagctaccc cagctactac     960
cgctacagca gctacccta ctacaactac agctatccca gctactacaa ctacggcagc    1020
taccccctact acagttatag cagctacccc agctggtact ggcgccgtct ccgctctttg    1080
gcaacagcaa cttgcccaga ctgccctcct ctcaccactc ccagcatgat cccaactccc    1140
cccccaatga tgaacatgat gaacaccca ccccatgg caaacatgat gaccagcatg    1200
atgatgaaca ctcccatggt tcctcctccc cgcaccctcg gaactgaagc catgagcctc    1260
ggcttggccc ccatcggtat caccggcgcc cccatgacag gttcggtgt tcctcctgag    1320
ttcggtccct ttggagccga aggtatcggc ctccccaccg atgccctcgg cagcaccccc    1380
gaaatgacac cattcgaccc aactacccc tacagaactc tcgcccccat ggacctcccc    1440
cccatccccc ctcctgtctt ccctgaaacc cctatgaggc cacctactcc cttcggcttc    1500
ggacctgcac ctgttcctcc catgcccttc taaacgacct accatccctc aatccatagc    1560
tcacatttcg tagcctcaaa acagtttttt gttcatttca cttccaggac tcatgctgcg    1620
acatttgcat tcgtacctcg aaaccgtcaa cctcaaaccc caaaccattc tgtgacctcc    1680
cctcgcaaac gcggaaggcg gaacatttt tctgaagtat attactacgt taaaaaaaaa    1740
aaaaaaaaaa aaaa                                                       1754
```

<210> SEQ ID NO 2
<211> LENGTH: 1754
<212> TYPE: DNA
<213> ORGANISM: Chicken

<400> SEQUENCE: 2

```
tcgtcttgta tccctcaagt agacaaggaa gaaaagtagt aaataaggag caaagagtgg    60
caaaataaaa aaaacacatt gggagaggcg acaactcagg gttactgggc ggagccggag   120
cgacgacagc gcgaccgaga gcggcacccg gaaggtacc gtcacgggtc gtggtgagga    180
cacctcttag tccaagtggg aatgtcgctc tactcatgga tggtcctccc ctcacggggc   240
ccccgaggcc tcctgtggtg gtggtggtga tgcagcaggg gacaaaggct acctcggctc   300
gtcaccgaac tctcgaaaca agcacgacac gtcgcggtcg acgtcgaagt cctggtttac   360
tacgcagtcg agtactccct gtaagtcctc atggactcgt gacgcaagtt gacccgtctc   420
ttggtcagat gacggatgtg gcacaatggc tctactacc tgtactagag gttgtcttac    480
ttacgtcgtt acctgtcgag tttgcttgag tactggtgat cgctgtggtg tctgggctc    540 tgggaggcgg cacgttgagc gttcatgtac ttcctccaag cgcaagtcct gcaggaccat   600
ctacgagaga cccggagaga ggcgccacat gtctgtcgac ggacctactt acctcactgg   660
cgataactct tcctcctctg ctgagggtac cgatcggcgc gacgactcct caaggaggtg   720
gcgtacatgg tattggactc ccgtcgtcca tacagacttc ttctacaacg gttcaagtag   780
ggatctcggc tcatgttggg gaggctcgtc agttctttat accgtctttt cccgtcctcg   840
aagatgatgc cgccgatagg gtcgatgatg ttgagggga tgatgtcgat gtcgtcgatg    900
gggtcgatga tgttgatgtc gatgggcagt atgtcgatgt cgtcgatggg gtcgatgatg   960
gcgatgtcgt cgatggggat gatgttgatg tcgatagggt cgatgatgtt gatgccgtcg  1020
atggggatga tgtcaatatc gtcgatgggg tcgaccatga ccgcggcaga ggcgagaaac  1080
cgttgtcgtt gaacgggtct gacgggagga gagtggtgag ggtcgtacta gggttgaggg  1140
gggggttact acttgtacta cttgtggggt gggggtacc gttttgtacta ctggtcgtac  1200 tactacttgt gagggtacca aggaggaggg gcgtgggagc cttgacttcg gtactcggag  1260
ccgaaccggg ggtagccata gtggccgcgg gggtactgtc caaagccaca aggaggactc  1320
aagccaggga aacctcggct tccatagccg gaggggtggc tacgggagcc gtcgtggggg  1380
ctttactgtg gtaagctggg ttgatggggg atgtcttgag agcgggggta cctggagggg  1440
gggtaggggg gaggacagaa gggactttgg ggatactccg gtggatgagg gaagccgaag  1500
cctggacgtg gacaaggagg gtacgggaag atttgctgga tggtagggag ttaggtatcg  1560
agtgtaaagc atcggagttt tgtcaaaaaa caagtaaagt gaaggtcctg agtacgacgc  1620
tgtaaacgta agcatggagc tttggcagtt ggagtttggg gttggtaag acactggagg    1680 ggagcgtttg cgccttccgc cttgtaaaaa agacttcata taatgatgca attttttttt  1740 ttttttttt tttt                                                      1754
```

<210> SEQ ID NO 3
<211> LENGTH: 476
<212> TYPE: PRT
<213> ORGANISM: Chicken

<400> SEQUENCE: 3

```
Met Thr Arg Leu Gly Leu Ala Ala Val Ala Leu Ala Leu Ala Val Gly
1               5                   10                  15

Pro Ser Met Ala Val Pro Ser Thr Thr Pro Val Glu Asn Gln Val His
            20                  25                  30

Pro Tyr Ser Glu Met Ser Thr Tyr Gln Glu Gly Ser Ala Pro Gly Ala
        35                  40                  45

Pro Glu Asp Thr Thr Thr Thr Thr Thr Ser Ser Pro Val Ser Asp Gly
    50                  55                  60
```

```
Ala Glu Gln Trp Leu Glu Ser Phe Val Arg Ala Val Gln Arg Gln Leu
 65                  70                  75                  80

Gln Leu Gln Asp Gln Met Met Arg Gln Leu Met Arg Asp Ile Gln Glu
                 85                  90                  95

Tyr Leu Ser Thr Ala Phe Asn Trp Ala Glu Asn Gln Ser Thr Ala Tyr
            100                 105                 110

Thr Arg Val Thr Glu Met Met Asp Met Ile Ser Asn Arg Met Asn Ala
        115                 120                 125

Ala Met Asp Ser Ser Asn Glu Leu Met Thr Thr Ser Asp Thr Thr Asp
130                 135                 140

Pro Glu Thr Leu Arg Arg Ala Thr Arg Lys Tyr Met Lys Glu Val Arg
145                 150                 155                 160

Val Gln Asp Val Leu Val Asp Ala Leu Trp Ala Ser Leu Arg Gly Val
                165                 170                 175

Gln Thr Ala Ala Trp Met Asn Gly Val Thr Ala Ile Glu Lys Glu Glu
            180                 185                 190

Thr Thr Pro Met Ala Ser Arg Ala Ala Glu Glu Phe Leu His Arg Met
        195                 200                 205

Tyr His Asn Leu Arg Ala Ala Gly Met Ser Glu Asp Val Ala Lys
210                 215                 220

Phe Ile Pro Arg Ala Glu Tyr Asn Pro Ser Glu Gln Ser Arg Asn Met
225                 230                 235                 240

Gly Arg Lys Gly Arg Ser Phe Tyr Gly Gly Tyr Pro Ser Tyr Tyr
                245                 250                 255

Asn Ser Pro Tyr Tyr Ser Tyr Ser Ser Tyr Pro Ser Tyr Tyr Asn Tyr
            260                 265                 270

Ser Tyr Pro Ser Tyr Ser Tyr Ser Ser Tyr Pro Ser Tyr Tyr Arg Tyr
        275                 280                 285

Ser Ser Tyr Pro Tyr Tyr Asn Tyr Ser Tyr Pro Ser Tyr Tyr Asn Tyr
290                 295                 300

Gly Ser Tyr Pro Tyr Tyr Ser Tyr Ser Ser Tyr Pro Ser Trp Tyr Trp
305                 310                 315                 320

Arg Arg Leu Arg Ser Leu Ala Thr Ala Thr Cys Pro Asp Cys Pro Pro
                325                 330                 335

Leu Thr Thr Pro Ser Met Ile Pro Thr Pro Pro Met Met Asn Met
            340                 345                 350

Met Asn Thr Pro Pro Met Ala Asn Met Met Thr Ser Met Met Met
                355                 360                 365

Asn Thr Pro Met Val Pro Pro Arg Thr Leu Gly Thr Glu Ala Met
            370                 375                 380

Ser Leu Gly Leu Ala Pro Ile Gly Ile Thr Gly Ala Pro Met Thr Gly
385                 390                 395                 400

Phe Gly Val Pro Pro Glu Phe Gly Pro Phe Gly Ala Glu Gly Ile Gly
                405                 410                 415

Leu Pro Thr Asp Ala Leu Gly Ser Thr Pro Glu Met Thr Pro Phe Asp
            420                 425                 430

Pro Thr Pro Tyr Arg Thr Leu Ala Pro Met Asp Leu Pro Pro Ile
        435                 440                 445

Pro Pro Pro Val Phe Pro Glu Thr Pro Met Arg Pro Pro Thr Pro Phe
450                 455                 460

Gly Phe Gly Pro Ala Pro Val Pro Pro Met Pro Phe
465                 470                 475
```

<210> SEQ ID NO 4

<211> LENGTH: 2145
<212> TYPE: DNA
<213> ORGANISM: Chicken

<400> SEQUENCE: 4

| | | | | | |
|---|---|---|---|---|---|
| atacaaatcc | tttttatctg | gttccaacac | gctcactcaa | ccaccacctg | gacacaccct | 60 |
| ccccatacat | acaggagcag | cagcaacacc | agcatcaaga | tgacgcgtgc | ggcagcgctt | 120 |
| gccgggtttt | tggccctggc | tgcagcaggc | agcagccttg | ctctacctac | tgtattggac | 180 |
| acaacgactg | gcacccaagt | ggagtggact | gagacccct | tagacacaac | agaggtaact | 240 |
| atgggggaga | tggcagcac | caccagcggc | acgactccaa | ccagcactgg | tgtgcgaatg | 300 |
| atggaggctg | aaactacaac | cccatcaacc | cctgaggctc | cccagcagca | gcagcagatg | 360 |
| cctcagcctc | aacctcagcc | acagcaaaca | actcccgttc | ctgaggccgt | attagaggca | 420 |
| attatgcaag | aaatgcaaaa | tattttccgt | tcttctcttg | taccaggttg | ggatactgtc | 480 |
| ggtacagcag | cagatgctgt | acgtcagatt | gtaacccgtg | taagagaacg | tcttacagga | 540 |
| ccattaatga | tgacagagat | ggatactggt | cttggtagaa | caggaccttt | atcaaccaca | 600 |
| ggtgcaacag | gagcaacaac | aggtcctgtt | gctgcattac | gcggtgtaac | aaatgatttc | 660 |
| cttagggaaa | taatgattca | agaagcagta | cttgagacat | tatgggcagt | tgtacgtgat | 720 |
| gcacaagaaa | gaccatggct | agttaatgaa | caggaagtat | tgcatgcagt | aacagcagat | 780 |
| gctgtacaag | gtttccttgg | tcgcatgcat | gatcgtcttc | gtgcaacagg | tttctctgag | 840 |
| gaagaagtca | tgagacttct | acctaggtca | cgtaatggtg | gttgtacccg | tacaggggggc | 900 |
| ctctttgatc | aatgtaacga | tgcccctccc | tctcgtcttc | ttggtaagag | gatgtatagt | 960 |
| actggatatt | atggttatgg | atatccttct | tattatagct | atggatatag | ttatccagct | 1020 |
| tattcacatt | atcctgtttc | ttatccttac | tatgggtata | gctggggccc | ctcatactac | 1080 |
| tatggcagcg | gatactatgg | taaacatgga | tataagtacg | gacattatta | caggagactt | 1140 |
| gctgagcagg | aaccaagacc | tgttatgcct | cctgcagcag | caactgccgc | agcaaaccta | 1200 |
| agagcagcag | cagcagcagc | agcagaagta | ccaccaccac | caccaccagc | agcagtacca | 1260 |
| ccaccaccac | cagcagcagc | agcaggtacc | ccagctatga | tgcctcctcc | tatgatgggt | 1320 |
| gttgaagaac | ctgttccttt | ccgctcccctc | tatcctagct | atagctggag | ttatccagca | 1380 |
| tatactcgcg | tgtctccctc | ttattcttat | tatacaccct | cttatagttc | ttcttactat | 1440 |
| tatccccgtt | ataattatgc | ctataactat | cccttatatt | cagactatag | ctggtatgat | 1500 |
| tatagctacc | cccttgccta | cagcagctat | agtagctacc | ccctttccta | tagtagctat | 1560 |
| agctaccccc | ttagctatac | ctaccctagt | gcctttttata | gaagactaga | ggtccctgat | 1620 |
| ctaacaacaa | ctactactac | tcatcatgag | cagcagcagc | agcagcagca | agaaagtaca | 1680 |
| actactgctg | tacctacaga | aaccattact | actccctcta | ctcgtaatac | acacagcagc | 1740 |
| agcctaagaa | gagtaggaga | aagatatgag | cctattaccc | ctacacaaag | aactttttat | 1800 |
| aataatacag | aaggtactaa | caaccctgtc | tatacacccg | aaaatcttac | agaagatgaa | 1860 |
| ccacaaactg | tatgggaaac | atacaactaa | acccctaaacc | ctaaacccta | aaccctcaac | 1920 |
| cctaacattt | ctcatttttt | tatagagaaa | ttttagggaa | cactaacctg | cctgccttgc | 1980 |
| catcgtttat | atatatccat | tgtttattaa | ataaacaatt | tttatttacc | tctagtcgtc | 2040 |
| tttttattaa | cagcgcttat | tcgcgttgtt | tatacaaact | actactattt | ttacccaata | 2100 |
| atacttgtac | aggcattttt | taaaaaaaaaa | aaaaaaaaaa | aaaaa | | 2145 |

<210> SEQ ID NO 5

<211> LENGTH: 2145
<212> TYPE: DNA
<213> ORGANISM: Chicken

<400> SEQUENCE: 5

```
tatgtttagg aaaaatagac caaggttgtg cgagtgagtt ggtggtggac ctgtgtggga        60
ggggtatgta tgtcctcgtc gtcgttgtgg tcgtagttct actgcgcacg ccgtcgcgaa       120
cggcccaaa accgggaccg acgtcgtccg tcgtcggaac gagatggatg acataacctg        180
tgttgctgac cgtgggttca cctcacctga ctctggggga atctgtgttg tctccattga       240
tacccctct acccgtcgtg gtggtcgccg tgctgaggtt ggtcgtgacc acacgcttac        300
tacctccgac tttgatgttg gggtagttgg ggactccgag gggtcgtcgt cgtcgtctac       360
ggagtcggag ttggagtcgg tgtcgtttgt tgagggcaag gactccggca taatctccgt       420
taatacgttc tttacgtttt ataaaaggca agaagagaac atggtccaac cctatgacag       480
ccatgtcgtc gtctacgaca tgcagtctaa cattgggcac attctcttgc agaatgtcct       540
ggtaattact actgtctcta cctatgacca gaaccatctt gtcctggaaa tagttggtgt       600
ccacgttgtc ctcgttgttg tccaggacaa cgacgtaatg cgccacattg tttactaaag       660
gaatcccttt attactaagt tcttcgtcat gaactctgta atacccgtca acatgcacta       720
cgtgttcttt ctggtaccga tcaattactt gtccttcata acgtacgtca ttgtcgtcta       780
cgacatgttc caaaggaacc agcgtacgta ctagcagaag cacgttgtcc aaagagactc       840
cttcttcagt actctgaaga tggatccagt gcattaccac caacatgggc atgtcccccg       900
gagaaactag ttacattgct acggggaggg agagcagaag aaccattctc ctacatatca       960
tgacctataa taccaatacc tataggaaga ataatatcga tacctatatc aataggtcga      1020
ataagtgtaa taggacaaag aataggaatg atacccatat cgaccccggg gagtatgatg      1080
ataccgtcgc ctatgatacc atttgtacct atattcatgc ctgtaataat gtcctctgaa      1140
cgactcgtcc ttggttctgg acaatacgga ggacgtcgtc gttgacggcg tcgtttggat      1200
tctcgtcgtc gtcgtcgtcg tcgtcttcat ggtggtggtg gtggtggtcg tcgtcatggt      1260
ggtggtggtg gtcgtcgtcg tcgtccatgg ggtcgatact acggaggagg atactaccca      1320
caacttcttg gacaaggaaa ggcgagggag ataggatcga tatcgacctc aataggtcgt      1380
atatgagcgc acagagggag aataagaata atatgtggga gaatatcaag aagaatgata      1440
ataggggcaa tattaatacg gatattgata gggaatataa gtctgatatc gaccatacta      1500
atatcgatgg gggaacggat gtcgtcgata tcatcgatgg gggaaaggat atcatcgata      1560
tcgatggggg aatcgatatg gatgggatca cggaaaatat cttctgatct ccagggacta      1620
gattgttgtt gatgatgatg agtagtactc gtcgtcgtcg tcgtcgtcgt tctttcatgt      1680
tgatgacgac atggatgtct ttggtaatga tgagggagat gagcattatg tgtgtcgtcg      1740
tcggattctt ctcatcctct ttctatactc ggataatggg gatgtgtttc ttgaaaaata      1800
ttattatgtc ttccatgatt gttgggacag atatgtgggc ttttagaatg tcttctactt      1860
ggtgtttgac atacccttg tatgttgatt tgggatttgg gatttgggat ttgggagttg      1920
ggattgtaaa gagtaaaaaa atatctcttt aaaatcccctt gtgattggac ggacggaacg      1980
gtagcaaata tatataggta aacaaataat tatttgttaa aaataaatgg agatcagcag      2040
aaaaataatt gtcgcgaata agcgcaacaa atatgtttga tgatgataaa aatgggttat      2100
tatgaacatg tccgtaaaaa attttttttt ttttttttt ttttt                       2145
```

<210> SEQ ID NO 6

```
<211> LENGTH: 596
<212> TYPE: PRT
<213> ORGANISM: Chicken

<400> SEQUENCE: 6

Met Thr Arg Ala Ala Leu Ala Gly Val Leu Ala Leu Ala Ala Ala
1               5                   10                  15

Gly Ser Ser Leu Ala Leu Pro Thr Val Leu Asp Thr Thr Gly Thr
                20                  25                  30

Gln Val Glu Trp Thr Glu Thr Pro Leu Asp Thr Thr Glu Val Thr Met
            35                  40                  45

Gly Glu Met Gly Ser Thr Thr Ser Gly Thr Thr Pro Thr Ser Thr Gly
    50                  55                  60

Val Arg Met Met Glu Ala Glu Thr Thr Thr Pro Ser Thr Pro Glu Ala
65                  70                  75                  80

Pro Gln Gln Gln Gln Met Pro Gln Pro Gln Pro Gln Pro Gln Gln
                85                  90                  95

Thr Thr Pro Val Pro Glu Ala Val Leu Glu Ala Ile Met Gln Glu Met
                100                 105                 110

Gln Asn Ile Phe Arg Ser Ser Leu Val Pro Gly Trp Asp Thr Val Gly
            115                 120                 125

Thr Ala Ala Asp Ala Val Arg Gln Ile Val Thr Arg Val Arg Glu Arg
    130                 135                 140

Leu Thr Gly Pro Leu Met Met Thr Glu Met Asp Thr Gly Leu Gly Arg
145                 150                 155                 160

Thr Gly Pro Leu Ser Thr Thr Gly Ala Thr Gly Ala Thr Thr Gly Pro
                165                 170                 175

Val Ala Ala Leu Arg Gly Val Thr Asn Asp Phe Leu Arg Glu Ile Met
                180                 185                 190

Ile Gln Glu Ala Val Leu Glu Thr Leu Trp Ala Val Val Arg Asp Ala
            195                 200                 205

Gln Glu Arg Pro Trp Leu Val Asn Glu Gln Glu Val Leu His Ala Val
    210                 215                 220

Thr Ala Asp Ala Val Gln Gly Phe Leu Gly Arg Met His Asp Arg Leu
225                 230                 235                 240

Arg Ala Thr Gly Phe Ser Glu Glu Glu Val Met Arg Leu Leu Pro Arg
                245                 250                 255

Ser Arg Asn Gly Gly Cys Thr Arg Thr Gly Gly Leu Phe Asp Gln Cys
                260                 265                 270

Asn Asp Ala Pro Pro Ser Arg Leu Leu Gly Lys Arg Met Tyr Ser Thr
            275                 280                 285

Gly Tyr Tyr Gly Tyr Gly Tyr Pro Ser Tyr Tyr Ser Tyr Gly Tyr Ser
    290                 295                 300

Tyr Pro Ala Tyr Ser His Tyr Pro Val Ser Tyr Pro Tyr Tyr Gly Tyr
305                 310                 315                 320

Ser Trp Gly Pro Ser Tyr Tyr Gly Ser Gly Tyr Tyr Gly Lys His
                325                 330                 335

Gly Tyr Lys Tyr Gly His Tyr Tyr Arg Arg Leu Ala Glu Gln Glu Pro
            340                 345                 350

Arg Pro Val Met Pro Pro Ala Ala Thr Ala Ala Ala Asn Leu Arg
                355                 360                 365

Ala Ala Ala Ala Ala Ala Glu Val Pro Pro Pro Pro Pro Ala
    370                 375                 380

Ala Val Pro Pro Pro Pro Ala Ala Ala Gly Thr Pro Ala Met
385                 390                 395                 400
```

```
Met Pro Pro Pro Met Met Gly Val Glu Glu Pro Val Pro Phe Arg Ser
            405                 410                 415
Leu Tyr Pro Ser Tyr Ser Trp Ser Tyr Pro Ala Tyr Thr Arg Val Ser
            420                 425                 430
Pro Ser Tyr Ser Tyr Tyr Thr Pro Ser Tyr Ser Ser Tyr Tyr
            435                 440                 445
Pro Arg Tyr Asn Tyr Ala Tyr Asn Tyr Pro Leu Tyr Ser Asp Tyr Ser
450                 455                 460
Trp Tyr Asp Tyr Ser Tyr Pro Leu Ala Tyr Ser Ser Tyr Ser Ser Tyr
465                 470                 475                 480
Pro Leu Ser Tyr Ser Ser Tyr Ser Tyr Pro Leu Ser Tyr Thr Tyr Pro
                485                 490                 495
Ser Ala Phe Tyr Arg Arg Leu Glu Val Pro Asp Leu Thr Thr Thr
                500                 505                 510
Thr Thr His His Glu Gln Gln Gln Gln Gln Gln Glu Ser Thr Thr
            515                 520                 525
Thr Ala Val Pro Thr Glu Thr Ile Thr Thr Pro Ser Thr Arg Asn Thr
            530                 535                 540
His Ser Ser Ser Leu Arg Arg Val Gly Glu Arg Tyr Glu Pro Ile Thr
545                 550                 555                 560
Pro Thr Gln Arg Thr Phe Tyr Asn Asn Thr Glu Gly Thr Asn Asn Pro
                565                 570                 575
Val Tyr Thr Pro Glu Asn Leu Thr Glu Asp Glu Pro Gln Thr Val Trp
                580                 585                 590
Glu Thr Tyr Asn
            595

<210> SEQ ID NO 7
<211> LENGTH: 16
<212> TYPE: PRT
<213> ORGANISM: Chicken

<400> SEQUENCE: 7

Val Pro Ser Thr Thr Pro Val Glu Asn Gln Val His Pro Tyr Glu Met
1               5                   10                  15

<210> SEQ ID NO 8
<211> LENGTH: 14
<212> TYPE: PRT
<213> ORGANISM: Chicken

<400> SEQUENCE: 8

Pro Thr Val Leu Asp Thr Thr Thr Gly Gln Val Glu Asp Thr
1               5                   10

<210> SEQ ID NO 9
<211> LENGTH: 14
<212> TYPE: PRT
<213> ORGANISM: Chicken
<220> FEATURE:
<221> NAME/KEY: MISC_FEATURE
<222> LOCATION: (5)..(5)
<223> OTHER INFORMATION: Where X= L/I
<220> FEATURE:
<221> NAME/KEY: MISC_FEATURE
<222> LOCATION: (9)..(9)
<223> OTHER INFORMATION: Where X= L/I
<220> FEATURE:
<221> NAME/KEY: MISC_FEATURE
<222> LOCATION: (13)..(13)
<223> OTHER INFORMATION: Where X= L/I
```

-continued

```
<400> SEQUENCE: 9

Val Gln Asp Val Xaa Val Asp Ala Xaa Trp Ala Ser Xaa Arg
1               5                   10

<210> SEQ ID NO 10
<211> LENGTH: 11
<212> TYPE: PRT
<213> ORGANISM: Chicken

<400> SEQUENCE: 10

Ala Thr Gly Phe Ser Glu Glu Glu Val Met Arg
1               5                   10

<210> SEQ ID NO 11
<211> LENGTH: 11
<212> TYPE: PRT
<213> ORGANISM: Chicken
<220> FEATURE:
<221> NAME/KEY: MISC_FEATURE
<222> LOCATION: (8)..(8)
<223> OTHER INFORMATION: Where X= L/I

<400> SEQUENCE: 11

Val Thr Glu Met Met Asp Met Xaa Ser Asn Arg
1               5                   10

<210> SEQ ID NO 12
<211> LENGTH: 16
<212> TYPE: PRT
<213> ORGANISM: Chicken

<400> SEQUENCE: 12

Thr Gly Gly Leu Phe Asp Gln Ala Cys Asn Asp Ala Pro Pro Ser Arg
1               5                   10                  15

<210> SEQ ID NO 13
<211> LENGTH: 10
<212> TYPE: PRT
<213> ORGANISM: Chicken
<220> FEATURE:
<221> NAME/KEY: MISC_FEATURE
<222> LOCATION: (2)..(2)
<223> OTHER INFORMATION: Where X= L/I
<220> FEATURE:
<221> NAME/KEY: MISC_FEATURE
<222> LOCATION: (4)..(4)
<223> OTHER INFORMATION: Where X= L/I

<400> SEQUENCE: 13

Gln Xaa Gln Xaa Gln Asp Gln Met Met Arg
1               5                   10

<210> SEQ ID NO 14
<211> LENGTH: 21
<212> TYPE: PRT
<213> ORGANISM: Chicken
<220> FEATURE:
<221> NAME/KEY: MISC_FEATURE
<222> LOCATION: (4)..(4)
<223> OTHER INFORMATION: Where X= L/I
<220> FEATURE:
<221> NAME/KEY: MISC_FEATURE
<222> LOCATION: (20)..(20)
<223> OTHER INFORMATION: Where X= L/I

<400> SEQUENCE: 14

Thr Gly Pro Xaa Ser Thr Thr Gly Ala Thr Gly Ala Thr Thr Gly Pro
1               5                   10                  15
```

Val Ala Ala Xaa Arg
            20

<210> SEQ ID NO 15
<211> LENGTH: 8
<212> TYPE: PRT
<213> ORGANISM: Chicken
<220> FEATURE:
<221> NAME/KEY: MISC_FEATURE
<222> LOCATION: (6)..(6)
<223> OTHER INFORMATION: Where X= L/I

<400> SEQUENCE: 15

Ala Ala Glu Glu Phe Xaa His Arg
1               5

<210> SEQ ID NO 16
<211> LENGTH: 6
<212> TYPE: PRT
<213> ORGANISM: Chicken
<220> FEATURE:
<221> NAME/KEY: MISC_FEATURE
<222> LOCATION: (2)..(2)
<223> OTHER INFORMATION: Where X= L/I

<400> SEQUENCE: 16

Pro Xaa Thr His Val Glu
1               5

<210> SEQ ID NO 17
<211> LENGTH: 12
<212> TYPE: PRT
<213> ORGANISM: Chicken
<220> FEATURE:
<221> NAME/KEY: MISC_FEATURE
<222> LOCATION: (2)..(2)
<223> OTHER INFORMATION: Where X= L/I

<400> SEQUENCE: 17

Arg Xaa Ala Ala Val Pro Gly Thr Thr Ala Gly Thr
1               5                   10

<210> SEQ ID NO 18
<211> LENGTH: 22
<212> TYPE: PRT
<213> ORGANISM: Chicken
<220> FEATURE:
<221> NAME/KEY: MISC_FEATURE
<222> LOCATION: (2)..(2)
<223> OTHER INFORMATION: Where X= L/I
<220> FEATURE:
<221> NAME/KEY: MISC_FEATURE
<222> LOCATION: (6)..(6)
<223> OTHER INFORMATION: Where X= L/I

<400> SEQUENCE: 18

Asp Xaa Gln Glu Tyr Xaa Ser Thr Ala Phe Asn Trp Ala Glu Asn Gln
1               5                   10                  15

Ser Thr Ala Tyr Thr Arg
            20

<210> SEQ ID NO 19
<211> LENGTH: 23
<212> TYPE: PRT
<213> ORGANISM: Chicken
<220> FEATURE:
<221> NAME/KEY: MISC_FEATURE
<222> LOCATION: (1)..(1)
<223> OTHER INFORMATION: Where X= L/I

<400> SEQUENCE: 19

Xaa Ala Glu Gly Ala Glu Pro Arg Pro Val Met Pro Pro Ala Ala Ala
1               5                   10                  15

Thr Ala Ala Ala Asn Leu Arg
            20

<210> SEQ ID NO 20
<211> LENGTH: 18
<212> TYPE: PRT
<213> ORGANISM: Chicken
<220> FEATURE:
<221> NAME/KEY: MISC_FEATURE
<222> LOCATION: (12)..(12)
<223> OTHER INFORMATION: Where X= L/I

<400> SEQUENCE: 20

Arg Gln Thr Ala Ala Trp Met Asp Arg Thr Ala Xaa Glu Gln Glu Glu
1               5                   10                  15

Thr Thr

<210> SEQ ID NO 21
<211> LENGTH: 14
<212> TYPE: PRT
<213> ORGANISM: Chicken
<220> FEATURE:
<221> NAME/KEY: MISC_FEATURE
<222> LOCATION: (11)..(11)
<223> OTHER INFORMATION: Where X= L/I

<400> SEQUENCE: 21

Met Asn Ala Ala Met Asp Ser Ser Asn Glu Xaa Met Thr Thr
1               5                   10

<210> SEQ ID NO 22
<211> LENGTH: 7
<212> TYPE: PRT
<213> ORGANISM: Chicken
<220> FEATURE:
<221> NAME/KEY: MISC_FEATURE
<222> LOCATION: (6)..(6)
<223> OTHER INFORMATION: Where X= L/I

<400> SEQUENCE: 22

Lys Phe Pro Glu Thr Xaa Phe
1               5

<210> SEQ ID NO 23
<211> LENGTH: 18
<212> TYPE: PRT
<213> ORGANISM: Chicken
<220> FEATURE:
<221> NAME/KEY: MISC_FEATURE
<222> LOCATION: (12)..(12)
<223> OTHER INFORMATION: Where X= L/I

<400> SEQUENCE: 23

Arg Gln Thr Ala Ala Trp Met Asp Arg Thr Ala Xaa Glu Gln Glu Glu
1               5                   10                  15

Thr Thr

<210> SEQ ID NO 24
<211> LENGTH: 21
<212> TYPE: PRT
<213> ORGANISM: Chicken

<400> SEQUENCE: 24

Arg Gly Val Gln Thr Ala Ala Trp Met Asp Gly Val Thr Ala Ile Glu
1               5                   10                  15

Lys Glu Glu Thr Thr
            20

<210> SEQ ID NO 25
<211> LENGTH: 21
<212> TYPE: PRT
<213> ORGANISM: Chicken

<400> SEQUENCE: 25

Arg Gly Val Gln Thr Ala Ala Trp Met Asn Gly Val Thr Ala Ile Glu
1               5                   10                  15

Lys Glu Glu Thr Thr
            20

<210> SEQ ID NO 26
<211> LENGTH: 7077
<212> TYPE: DNA
<213> ORGANISM: Chicken

<400> SEQUENCE: 26

| | | | | | |
|---|---|---|---|---|---|
| atgctgcatc | gcaacccgcg | gtgggcgctt | tgtgcagccc | tcgctgcact | ctatggcgga | 60 |
| acaggaatcg | ccagcgccga | agttaacaat | gaattgagca | agtgcgaatc | tgggtggaca | 120 |
| ccctggacta | cctgcaaccc | gcaaactggt | ctgcgggaga | ggcacaatgc | acagtgcgag | 180 |
| acatgggtgg | aggttgagga | atgccagaag | ctgacaggat | gtggcaactg | gactccttgg | 240 |
| tctcccggcg | atatgtcgtg | tgtggtggga | cagtttcaaa | cccgcaacag | ggagggctgc | 300 |
| ccagaggtgc | aggaagtgag | ggcatgcagg | cctgtacttc | tagaatgcaa | cgatcaatgg | 360 |
| acccccctgga | caatgtgcga | caccaaccgc | gtccaggaaa | gatacaactc | aaagtgcgga | 420 |
| cccgtcgaag | tccgcgagtg | caacatggac | gacgcagaga | tcgagaaatg | cggcgagttc | 480 |
| gtggaatggg | atccccctat | gaatggagac | tgcgtacgcg | ggggtaccca | cacgcgttac | 540 |
| cgtcaaaact | gcccagaccg | caaagaggtg | cgggtgtgcg | gagcctttga | ttgcagtagc | 600 |
| tgctctgtaa | acgccacttg | cgatcccatt | ggtgcatcct | gcgaatgcaa | gcctggtttc | 660 |
| cgcggcaatg | ggaagacctg | cgaggccttc | aacccctgcg | aagataccc | tgcaccttgc | 720 |
| gacagcaacg | ccatctgcac | cccagacgca | atgacgccaa | atgccagtgc | aaggcaggct | 780 |
| gggacgcaga | ttccggagca | ggcagcagca | agaagccttg | cgttgaggtc | gacgagtgcg | 840 |
| catccaacac | ccaccagtgc | ccggcacact | ccacatgcat | caacaccaag | ggctcttata | 900 |
| agtgcgactg | caaccaggga | taccgtcaag | ggagaggacg | gacagtgtca | tgacgtcgat | 960 |
| gaatgcacca | acgagagca | cacctgcccc | gctcactcca | cttgtttgaa | tacagctggc | 1020 |
| agctacgagt | gccgctgcga | cactgggtac | agcggaaatg | caactgcaga | cagcccttgc | 1080 |
| aagaacattg | acgaatgcgc | caaccccaac | gcctgctcgg | ccaacgctat | ctgcacagac | 1140 |
| accgacggct | ccttcacctg | cagctgcccc | gaagggtaca | gcggccaggg | aacccatgac | 1200 |
| tctccctgct | ccaagatcga | cttctgcgca | taccccctcac | tcaatacatg | cggagcccac | 1260 |
| tccacttgca | cacccctcac | atctttcaag | tgcatctgcg | atgcgggata | tgaaggcgcc | 1320 |
| ggcactcgcg | agagcccgtg | cgtggacgtg | aacgagtgct | cgaacgagaa | gcccacaaac | 1380 |
| aactgcaaca | gaaacgcaaa | ctgcaccaac | accgagggat | cctacacttg | cgaatgcaag | 1440 |
| cccggtttct | ctggcgacgg | catgggtccc | aacgggtgta | ccgacatcga | cgagtgcgcg | 1500 |
| gcggagcagt | cccctgcga | ccctcacgcc | tcctgcagca | acactgaggg | ctcgtatgta | 1560 |

-continued

```
tgcacctgca acaccggcta cgagccagct tcaaccgacg ggcatgcatg caaagatatc    1620
gacgagtgcg ccaccggtgc agctgggtgc cacgtgtcag cacagtgtct gaacacggac    1680
ggcagctacg agtgcaagtg tcttgagggc ttcgtcggcg acggaaagac ctgcaacgac    1740
gtcgatgagt gcgctgcggc gacatctcct tgcggtgaca acactcactg ccagaacaca    1800
attggcagct acgagtgcga gtgcaaggct ggctatggca acatgcaaga caacgcatgc    1860
agcgacattg acgagtgcaa ggatgcgaac accaagatcc ctgacaactg tctttgcgtg    1920
aacaatgatg gcagctactc ccttgaggcg aaggctggat acgaattggt gaacggcgag    1980
tgcatcaaga tcgacttctg cgcccgcggc gcatgcaact cgctggcctc ctgcaaggag    2040
aatgaagaag gcacagcggc gatctgcacc tgcctgccag gctacagcgg cgacggcact    2100
gctgaaggcc actgcaacga cattgacgag tgtgcaggtc agaatgactg tgctcctgcc    2160
gagcagggag gcatctgcga gaacactgtc ggctcgtaca cctgcaagtg caaagagggg    2220
tacaggcaag atggaaactc atgcactgag atcgacgagt gcgctgaggg aacccacaac    2280 tgccacccctt ccgccacctg cagcaacacc cccggaagct tcacctgcca atgcaacagt    2340
ggattcactg gcagcggtgt ggagtgcgaa gacattgacg agtgctcaac tgaggcagat    2400
gattgtggtg caaacaccat ctgcagcaac accattggtg ctttcgagtg caactgccgt    2460
gaaggctatg aacgcgcaga cgcaaagacg tgcgtcgaca tcgacgaatg cgcgacaggc    2520
acacacactt gctcgaacca cgccacctgc accaataccg atgggtcatt cacatgccag    2580
tgcaaccccg gcttcgaagg tgacggccac aagtgcgagg acatcgactt ctgcggtgct    2640
ggacagcacg actgcaatgt gcatgccgag tgctctgaga gcgaggacaa caccactttc    2700
aagtgcacct gtataacagg gtacgctgga gacggccatg gcgaggcagg ctgccaagac    2760
attgatgagt gcgcagaaga aaacatctgc ggaagcaacg ctgtctgcac aaacaccgca    2820
ggaagctacc aatgcgcatg ccgtgagggc ttcgttgcat cagctgaaca gcagcagcag    2880
ggaaccccag cactggtttg cgtggacgtc gacgagtgca gcgacgcttc gaagaacaca    2940
tgtgccaagc cagccgacgg aggcatttgc acaaacactg aaggcagcta cgaatgcgct    3000
tgcaagccag gctaccaagg tgacggccac agctgcgcag acatcaacga atgcactgca    3060
cagggcacct gcggcgaaca cacaacttgc aagaacacac ccggatcctt ccagtgcgac    3120
tgcgttgagg gattcgagcg cgctgatgaa cgcacctgcc gtgacatcaa cgagtgcgag    3180
acaggagcag tcgtgctgcc accgaactcc acctgcgtca acactgaagg cagctacgac    3240
ttcgactgcg ttgctgggta ccgccgcact gatggagctt gtgtgaagat cgacttctgc    3300
aaggagaagg gatgcaacgc aaacgccaca tgccgcgaaa acgatgccgg caccgaggcc    3360
atctgcactt gcaaggaagg ctatgaaggc agcggagaag gcgaagatgg ttgccagaac    3420
atcaatgagt gcgagagagg cgaaccctgc aaggacttcg gcgaaggcgg tgtttgcgtc    3480
gacacaccag gatcattcac ttgcgagtgc gctgctggat tcattcaacg ccgctccgtt    3540
tgccaagatg ttgacgaatg tctcgacgga aagctgaaca cctgcgctgc caccggaggc    3600
gtctgctcca acaccgtcgg ttccttcacc tgctcgtgcg ccagcggctt cgaaggcgat    3660
ggccacacct gcaatgatgt cgacgaatgc gcaacagcac agcacacctg tgacccgaat    3720
gccacttgcg tcaacaccga aggcagcttc gagtgccgct gcaatgccgg attcgagggc    3780
gacggacaca cctgcgcaga catcgacgaa tgcgcagacc cagccaaaaa cacatgcgat    3840
acacacaagg gtgtatgcca aaacaccaca gggtcctaca cctgcggctg caagaccgga    3900
ttcagtcttg cagctgacgg aagcacatgc gaaaacgtcg acgagtgcgc ggcgggaact    3960
```

```
gcaaactgca acgagcgaag cttctgtaag gacacagagg gttcctacca atgcgagtgc    4020
aagaacggct acaaggctgc aggagaggac tgtgtggacg ttgacgagtg cgaggctggc    4080
gtgcatggat gcagcgagca cgcaatctgc acaaatacag acggcagcta ctcctgcgaa    4140
tgcatggagg gataccaggg agacggcaag gcttgcgaga agacagtcgg cgtctgcgac    4200
tccgctccct gcggtgccca cgccacctgc gagcctgcag gggacaacta cacttgcaca    4260
tgccacccag gctacgagat gcgcgaagga gcctgcgttg acatcgatga gtgcacagca    4320
ggcagcctca actgcgaccc tcatgccatt tgcacaaaca ccgacggctc cttcacttgc    4380
gtctgtggca gcggctatac cggccttggc acatcctgcg aagacatcga cgagtgcgcg    4440
ggtaacgcag caggctgcga catccacgcc gtctgcacga acactcccgg atcgttcaag    4500
tgcgagtgca agagcggctt cgaaggcgat ggcacgcaat gcacggagaa ggtgttgctc    4560
cccggacaga ttcactgcga agcctggact gcatggacag agtgtaccga cggcgccaaa    4620
accagcacac gcagctgcct tgcactgccg cttaagaagg agatgcgcgc ctgccctgca    4680
gctgacttct cccagtgcgg agagttcact gaatggactg cctgccctgg aaccaacaat    4740
aacctgtctc ataggcgcac tgaaagattc ggagaacccg gatgcgaaga tgcagaggaa    4800
gtccgcgaat gcccagatga agagaccgag cagaaatgcg gcgcctgggg tgagtggacc    4860
gcctgcggcg acccatcccc tggcctgaga actcgcgcac gcgagaactg ccccgatgtg    4920
gtagagttcg agcgttgcac tatgcccagt gagcctgagg ctggcgaagt gactgagcct    4980
cacacagaag gaggagccgg agttggtggc gaagtgactg agcctgacac ggaagaagga    5040
gccggagttg gtggtgaagt gcagcccggt acagaagaag gagcaggagt tggtggtgaa    5100
gtgcagcccg gtacagaaga aggagccgga gttggtggtg aagtgcagcc cggtacagaa    5160
gaaggagccg gagttggtgg tgaagtgcag cccggtacgg aagaaggagc cggcattggt    5220
ggcgaagtga ctgagcctga caccgaagga ggagccggag ttagtggcga accgaccgaa    5280
gaagagggca ccgaaagcac cggtccatgc aaagagttcg gaccctggac ggcctgcaag    5340
gaggacgaga acgagtcgg catccaacgc cgtatgtgcg ccggcagaga agacatcatc    5400
gaatccagaa tttgcactgt cacggatgac tgcggagaat ggacccctg gtcaacttgc    5460 actaacggca gccaggccag aaacaaacgc ttctgcacca acgttaggga agtccgtctc    5520
tgcggagctg acattccagt tacagacgga tgcacgtgga gcgagtggac ttcttgcagt    5580
ctagtcaatg aggagggcgg ctacttccgc acgcgcacat cctctgactg caacatgaat    5640
gaagtgcagg cctgctctcc cagcagcagc acaaccgcag acagcgaaac agaaggcacc    5700
tgctctgcat ggaaccctg acggagtgc tcgaacggcc accagacacg caagtgtgcc    5760
acaatggaag cagaagaatc gcgcacttgc ggagagactc cagagaactg cggagaattc    5820
ggccccttcg aacccgcaaa ctgcacggcc ggccaaatgg tcaccaggac gcgcacctgc    5880
ggagaaaccg agcagaagga aaccaaactg tgcgacgtca gctccaccga agaaggaaaa    5940
caatgcggtc agtggggccc atggagcgaa tgcaacatcc acctgggctc agaggacaat    6000
gtgcgtgttc gtgaggacac cgcttgcggc gtgacggagt cgaggagtg cagcaagccg    6060 gcgaacaacg cctttgtctg cacaccttgg agtgaatgct cggacaagaa ggagcggaga    6120 acgtgccacca tccgcaaaaa cggtcttgtt cagacacgtc aagaattcag aacatgcagt    6180
gtagacatcg ccacaacttg cggcgatttc ggcgcatggt ctgaatgcaa cgctgagggc    6240
ttgcatcagc gcagtctcga gaaatgcccc gacgtcatcg aggtcgcaac ttgcggcagt    6300
gaggattgcc cgccattcgg cgagtggact gaatgcggcg ttccagagga gggcatgcgt    6360
```

-continued

| | |
|---|---|
| tctcgccaac gcattgactg cgttgaatct gcagcctgcc agtgcacaga agtggagagc | 6420 |
| tgcttcgaca ccgaattgca ccccattcca gcccccggta cggaaacagg cgaaggagag | 6480 |
| ggagagaccg agacaggcga aggcgaaact ggtgaagcag gtggcgagga aggcgagcaa | 6540 |
| acaggagaag gcgaagtgca gccccagaa gaagagcttc ctggggagag tgtaactgag | 6600 |
| cctgaggaga agcctgagga ggagctacct gaggaggagg ttactgagcc tgaggagaag | 6660 |
| cctgaggagg gtgtgactca gcctgaggag acacctgagc agcctgttga gggtaccgaa | 6720 |
| gaagagggca agcaggagtc tgaggctgcc cccgaaactc ctgccgtcca gccaaaacca | 6780 |
| gaggagggtc acgaacgccc agaacccgaa gaggaggagg agaagaagga agaaggcggc | 6840 |
| ggcttcccaa cagctgcagt ggcaggaggt gttggtggtg tgttgctcat agctgctgta | 6900 |
| ggtggtggtg ttgcagcctt cactagcggc ggaggtggcg ctggcgcaca ggaggcagaa | 6960 |
| caggtcgagt tcgaaggaga agataccgga gcagcaactg ccgagacacc tgaagccgat | 7020 |
| acagttatcg acatcacaga cgaagacgac tactgggccg acagcggcga cattcag | 7077 |

<210> SEQ ID NO 27
<211> LENGTH: 6567
<212> TYPE: DNA
<213> ORGANISM: Chicken

<400> SEQUENCE: 27

| | |
|---|---|
| atgggttttt tcgtcttcac aggcggtgat tcggcgact ggagcccccc tctcgctggt | 60 |
| gactgcgtgc ctggcactac tcacacacgc cagagggcaa attgcccaaa ccacaaggag | 120 |
| gtgcggggttt gcggcgcctt cgattgtagc cagtgctcag tcaacgctac ctgcgacccc | 180 |
| ctcggagcca cttgtcagtg caaaccgggt ttccgaggcg atgggactca gtgcgaggca | 240 |
| ttcaacccctt gcgaagggga gacggctcct tgtgatgcga acgcgacctg cacggctgat | 300 |
| ggaaatgacg ccaaatgcca ctgcaacaag ggctggaacg cagacagcaa ggcaggtgcc | 360 |
| agcggtcacg catgcgtgga ggaggacgaa tgcgccaaca cacgcacga atgtccgcag | 420 |
| cactcaactt gcgtcaacac tgagggctcc tatgaatgca actgcttacc gggttatcag | 480 |
| aaggatcagg atgggaaatg ccaggacata gacgagtgcg ctggggaaca tggttgtccc | 540 |
| gcacactcga cttgcgtgaa cacggcaggc agcttcgagt gcaagtgcga cgccggtttc | 600 |
| agtggcagtg ctacttctga gagtccttgc tcgaatatag acgagtgcca agacccggat | 660 |
| gcctgctcag ccaacgcaat ctgcgcagac actgagggct ctttcacttg cagctgccct | 720 |
| gagggttaca cgcgtggggg atcacacgac tctccttgct cgaagataga ttactgcgcc | 780 |
| gacccccacac tgaacaccctg cggggcccac tcgacttgtg tgaacacact aacgacgttc | 840 |
| aagtgcgttt gcgatgccgg ttatgacggc gcgggaacgc acgagagccc ttgtgtggat | 900 |
| atcgacgagt gctccaagga gaaaccatcc aatgactgca accgaaacgc cgttttgcaca | 960 |
| aatactgagg gatcgtacac ctgcgcatgc aaggaaggct ctctggcga gggtttcgga | 1020 |
| gctgcagggt gtgcagatgt cgatgagtgc gcgaattcgc cctgcgacgc ccacgcctct | 1080 |
| tgtgccaaca ccgagggttc ctacgtttgc acttgcaacc ctggctatga accagcctca | 1140 |
| agcgacggac atgcatgcaa ggacgttgac gagtgtgcag cgggcacggc ggaatgccac | 1200 |
| gtctccgcac agtgtgtgaa cgtggatggc agctatgaat gccactgctt ggaaggtttc | 1260 |
| attggcgacg gaaaggtgtg cagtgacgtt gacgagtgtg cggctgaggc ttcgccctgt | 1320 |
| ggcgcaaaca cgcattgcct gaacaccatc ggcagctacg agtgcgagtg caaggacgga | 1380 |
| tatgccacca tggagggcaa cgcgtgcagc gacatcgatg agtgctcaga ggcgtctaca | 1440 |

```
gagatcccag agaactgcaa ctgtgtcaac accgagggga gcttctccct tgaggcaaag    1500
cctgggtacg agctcgtcga cggcaagtgc gtcaagatcg acttctgcgc ccgtggtgca    1560
tgcaactcgc tggcgcactg caaggagaat cccgagggca ccgcggcgat ctgcacttgc    1620
atagctggct attcaggtga cggcacagct cagggccact gcgatgacat cgatgagtgc    1680
ttggcggaga atgactgcac ccctgccgat caaggaggga tttgcgagaa cactgtcggc    1740
tcttacacct gcaaatgcgc agctgggtac cagcaagacg gcaactcatg cactgacatt    1800
gacgagtgcg ccaacggcac tcacaactgc catgcctccg cgacatgcac gaacacgcaa    1860
ggctcctttg agtgcgcctg caacgcaggc ttcagcggca acggggttga atgcaacgac    1920
gtcgacgagt gctcgactga cgctgacgat tgcggagaga acacactgtg caacaacaca    1980
gttggcagct tcgagtgcac atgcatggct ggcttcgagg ccgcggacgc gaagacctgc    2040
aaagacatcg acgaatgtgc aagcgggacc cacacttgct ccacccacgc gacatgcacc    2100
aacactgctg ggtcgttcac atgtgagtgc aacccaggct tgacggtga cggccacaag    2160 tgcgaggacg tggacttctg cggccagggg ctgcacgact gcaacgtgca tgcagagtgc    2220
tcggaaagcg acgacaacac caccttcaag tgcacctgcg gcattgggta cagcggggaa    2280
ggccacgggg agaatggttg ccaagacatt gatgagtgcg cccaagatgc catctgtggg    2340
gagaacacag tgtgtaccaa cacccaggt agctttgaat gtcgtgtgt ggaagggttc    2400 gtggctgtgg gagcgaagct caagggagca acttcattga cctgcataga catcgatgaa    2460
tgcaacgacg cctcgaaaaa cacttgcgcc acgtcagctg acggaggctc ttgcaagaac    2520
accgcaggca gctatgagtg ctcgtgtttg cctgggttcc agggcgacgg ccacagctgc    2580
acagatattg atgagtgcgc cacccaaggc gtatgcgggg aacatgcgac ctgcgaaaac    2640
actgcgggtt cgtacaattg cacctgcgag gcgggttaca ctcagcaaga tggggccgtc    2700
ggctgcattg atattgatga gtgtgcagcc tccacagcag tgttacccgc caacgccact    2760
tgcgtgaaca ctgaaggcag ctatacattc gaatgcgtgc ccggctaccg ccatacggag    2820
aatggctgta ccaagattga tttctgcagc gaaaagggat gcaatgcgaa tgccagctgc    2880
aaggagaacg atgcgggcac cgaagccatc tgcacctgcc acagcgggta cgagggcaat    2940
ggcgaaggag aagaagggtg caaaaacatt gacgagtgct ccgtgggaga gccatgcaaa    3000
gacttcggcg agggcggcgt ctgtgtcgat tctccgggat ccttcagctg ctcttgcgcc    3060
accggtttta tcaagaggcg atctacttgc caggacatag atgagtgcct cgacggaaag    3120
atgaacactt gcgcccccgt cggggtatc tgcacgaaca ccgtcggctc cttcacctgc    3180
tcttgcgctg ctggcttcac gggtgacggc cttacttgcg aggacatcga cgaatgtgct    3240
acggcggcac acacgtgcga ccccaacgcc acctgtgtca acactgtcgg cagcttcgaa    3300
tgcggatgca aggagggatt ctctggtgac ggccacacat gcaccgatat cgacgaatgc    3360
gctgacccta accttaacaa atgcgacaca cacaagggca tctgccagaa cggcactgga    3420
tcctacactt gcggatgcag gcctggatac agtctggcgg cggacggctt cacttgcgac    3480
aatgtcgatg agtgcgctgc ggggacggcc acttgcggag agcgcagctt ctgcgtggac    3540
acgcaagggt catacaagtg cgagtgcaag aacggctacc gccagtctgg ggaggactgc    3600
gtggacgttg acgagtgcga ggctgatgtg cacacatgca gcgagcacgc tacgtgcacg    3660
aacactgagg ggagccacac ctgcacctgc aatgaagggt accagggaga cggaaagaag    3720
tgcgagaaga cagtgggccc ttgcgacaac tcgccatgcg gcaacaacgc catgtgtgaa    3780
gctactgccg atagctacaa ctgcacttgc aaagctggct acgagatgaa ggacggggcc    3840
```

```
tgtgtcgaca tcgatgagtg ccagtcgggc acccacaact gcgacccgca tgctgactgc    3900
agcaacaccg atggatcctt cacgtgcacg tgcggttctg gctacactgg tgtgggtacc    3960
ctttgcgagg atgtggacga gtgcgcgggc aaccatgcgg gctgtgacat caacgctgtt    4020
tgcactaacg tccctggctc gttcacttgc gagtgcaaga gtggcttcga aggcgatggg    4080
cacgagtgta cggagaaagt gctgctccct ggccagattc actgcgattc gtggactgca    4140
tggaccgaat gtacagctga aactaagcag agcacccgca agtgcgtggc tcttcctctc    4200
aaggtcgagg tgaagctttg ccccgatgct gacatttcag cctgcggtga actcggcgag    4260
tggtcatcat gcccaggagt tgacaacaac ctgtcgcacc gcagagcaga aagttcggg    4320
gagccgggct gtgagcacgc tgaggaggtc agggagtgcc agatgaaga agttgaggag    4380
cgctgtggtg cctttggcga gtggactgca tgcggcgatc cttctgaggg cttgaggacc    4440
aggacgcgcc agaactgccc agaagaggca gaattcgagc actgcacaat gccctctgca    4500
ccatccgttc ccgagggcgg cagcagctgc acagagttcg gggcctggag tgaatgcgtg    4560
gctgacgctc atgggatcaa gatgcagcac agaacgtgcg tacacaatga agctgtgcag    4620
gaacacagaa tctgcaccgt ggaagatcca acagtgcgg gggagtggtc gcagtggtca    4680
gagtgcaaga atggcaagca gtacagaggc gccgccggat gcgcgtctgt gtacgaagtc    4740
agagcctgca gcggcgctag cgatgcgaaa gaatgctctt ttggtgcgtg gagcggctgc    4800
gtggtggagt ttggcggtca cacttacaaa gtgcgaaact caatcgactg cgagctcagt    4860
gagctgcagg cttgcaagcc gagcgccgcc accgagggcg agggcaagtg cgctgcttgg    4920
agcccctgga cgatctgcag ggacggcatg cagactcgcg actgcaaaag cctgggtgtt    4980
caggagtccc gcccatgctc agctgaagga gagaccgatt cttgcggagc ctttggaccc    5040
ttcgagccgg cagcttgcaa ggctggcgag atggtcacga ggacgcggga gtgcaacggt    5100
gctcagcaga aggaaaccag actgtgcaat cctgagggca atgacaactg caacaactgg    5160
ggtgcttgga cagagtgctc gctaattgtg ggcggctctg ccctgcggtc tcgcgaggag    5220
tccacttgcg gctatgtgga gttagaggag tgcagtggca gcagcagcag cggcgaccag    5280
accgtccact gcggcagctg gtcggagtgc tccatgagaa aaacggagcg cacctgtgat    5340
gtcctctctg acggatccca caccagcgtt actgaagtgc tcacctgcga cgacgtgctg    5400
cctgactctt gcggtgaatt tggcgagtgg tccaatgta gcgctgacgg cttgcactcg    5460
aggtccctgt caggctgccc agacgtaact gaagtgatga cttgcggcag cgaaaactgc    5520
ccggctttcg gcgagtggag cgagtgcggc agcccagagg acggcctacg gtcgcgtcag    5580
cgaacgaact gcgaagaggg atccggctgc atttgctccg agacagaagc ctgtgttaac    5640
actgagctcc accccatccc attgccagtt cctggcggcg gcgagggcag cgagaacggc    5700
gagggtggcc aaaccggaga ggagggaacg gagggaggcg caggcggtgc tggaggatcc    5760
ggtggtgctg aggagctgcc cggagaagag ggtggcgcag gtgccggcgg agaaggaggc    5820
tctggcggta atgctgagga gctgcccgga aagggggtg ctggcgaagc tggaggctct    5880
ggcggtagtg ctgaggagct gcccggagaa gagggcggcg caggtgccgg cggaggagga    5940
ggctctggcg gtagtgctga ggagctgcct ggagaagagg gcggcgcagg tgccggcgga    6000
gaaggaggct ctggcggcaa tgctgaggag ctgcccggag aagagggcgg cgcaggtgct    6060
ggaggagccg aaggcgagac agggaaacct ggcggcgaag agggtggcgc aggcggcgct    6120
ggtgagggtg ctggcggtga aggtggtgag gtccagcctg agagggaga aggggcgagt    6180
gaaggaggcg agcaagtgcc ggaaacccct gagacacccg aaccggaaac acctgaagct    6240
```

```
gagagacctg aagagcaacc ctcgacggaa actccagcag aggagcccac cgaaggcggt      6300
gcagaagaag aggagaagga ggagggcagc ggcttcccca cggcagctgt tgccggaggt      6360
gtaggtggtg tactactgct ggcagcagtg ggtggtggcg ttgccgcgta ctccggtggt      6420
ggtggaggtg gcggtgccga ggaggctgag caagttgagt ttgaaggtga agagtcgggt      6480
ggtgcgtctg ccgaaacacc tgaggctgat actgtgattg acatcactga cgaagacgac      6540
tactgggcag acagtggtga catccag                                          6567

<210> SEQ ID NO 28
<211> LENGTH: 293
<212> TYPE: DNA
<213> ORGANISM: Chicken

<400> SEQUENCE: 28
gtggtgattg aatctgctcc agccaagatg gctcaccctc ctgtggtgat tgagtctgct       60
ccggtcgagg tggtccatcc tcctatggtg attgaatctg ctccacccaa gatggctcaa      120
cctccgatgg tgattgagtc tgctccaccc aagatggctc aaccacctat ggtgattgag      180
tcggctcccg tcgaggtggt ccatcctcct atggtgatgg aagccgctcc caccgtgaag      240
ggaagatacc tcgctgctga ggatgaggtg gaagagcagt ttgaatcgaa cag             293

<210> SEQ ID NO 29
<211> LENGTH: 97
<212> TYPE: PRT
<213> ORGANISM: Chicken

<400> SEQUENCE: 29

Val Val Ile Glu Ser Ala Pro Ala Lys Met Ala His Pro Pro Val Val
1               5                   10                  15

Ile Glu Ser Ala Pro Val Glu Val Val His Pro Pro Met Val Ile Glu
            20                  25                  30

Ser Ala Pro Pro Lys Met Ala Gln Pro Pro Met Val Ile Glu Ser Ala
        35                  40                  45

Pro Pro Lys Met Ala Gln Pro Pro Met Val Ile Glu Ser Ala Pro Val
    50                  55                  60

Glu Val Val His Pro Pro Met Val Met Glu Ala Ala Pro Thr Val Lys
65                  70                  75                  80

Gly Arg Tyr Leu Ala Ala Glu Asp Glu Val Glu Glu Gln Phe Glu Ser
                85                  90                  95

Asn

<210> SEQ ID NO 30
<211> LENGTH: 196
<212> TYPE: DNA
<213> ORGANISM: Chicken

<400> SEQUENCE: 30
cctgcaggtt gtactaagag cgctttatga ctatcgggag ctcaaatgcg gctcagcatg       60
ccggaacgtg gcatttttgg tacacggagg tatcacctcg agcgaatggg cgggggtctt      120
tccgcaaaca agcgttccac caaaacctaa ggtggaaaac tgttcagttg catttaatta      180
cgcttttgta aatacc                                                     196

<210> SEQ ID NO 31
<211> LENGTH: 65
<212> TYPE: PRT
<213> ORGANISM: Chicken
```

```
<400> SEQUENCE: 31

Leu Gln Val Val Leu Arg Ala Leu Tyr Asp Tyr Arg Glu Leu Lys Cys
1               5                   10                  15

Gly Ser Ala Cys Arg Asn Val Gly Ile Leu Val His Gly Gly Ile Thr
            20                  25                  30

Ser Ser Glu Trp Ala Gly Val Phe Pro Gln Thr Ser Val Pro Pro Lys
        35                  40                  45

Pro Lys Val Glu Asn Cys Ser Val Ala Phe Asn Tyr Ala Phe Val Asn
    50                  55                  60

Thr
65

<210> SEQ ID NO 32
<211> LENGTH: 646
<212> TYPE: DNA
<213> ORGANISM: Chicken

<400> SEQUENCE: 32
cgaattgcac cccattccag cccccggtac ggaaacaggc gaaggagagg gagagaccga      60
gacaggcgaa ggcgaaactg gtgaagcagg tggcgaggag ggcgagcaaa caggagaagg     120
cgaagtgcag cccccagaag aagagcttcc tggggagagt gtaactgagc ctgaggagaa     180
gcctgaggag gagctacctg aggaggaggt tactgagcct gaggagaagc ctgaggaggg     240
tgtgactcag cctgaggaga cacctgagca gcctgttgag ggtaccgaag agagggcaa     300
gcaggagtct gaggctgccc ccgaaactcc tgccgtccag ccaaaaccag gagagggtca     360
cgaacgccca gaacccgaag aggaggagga gaagaaggaa gaaggcggcg gcttcccaac     420
agctgcagtg gcaggaggtg ttggtggtgt gttgctcata gctgctgtag gtggtggtgt     480
tgcagccttc actagcggcg gaggtggcgc tggcgcacag gaggcagaac aggtcgagtt     540
cgaaggagaa gataccggag cagcaactgc cgagacacct gaagccgata cagttatcga     600
catcacagac gaagacgact actgggccga cagcggcgac attcag                   646

<210> SEQ ID NO 33
<211> LENGTH: 215
<212> TYPE: PRT
<213> ORGANISM: Chicken

<400> SEQUENCE: 33

Glu Leu His Pro Ile Pro Ala Pro Gly Thr Glu Thr Gly Glu Gly Glu
1               5                   10                  15

Gly Glu Thr Glu Thr Gly Glu Gly Glu Thr Gly Glu Ala Gly Gly Glu
            20                  25                  30

Glu Gly Glu Gln Thr Gly Glu Gly Glu Val Gln Pro Pro Glu Glu Glu
        35                  40                  45

Leu Pro Gly Glu Ser Val Thr Glu Pro Glu Glu Lys Pro Glu Glu Glu
    50                  55                  60

Leu Pro Glu Glu Glu Val Thr Glu Pro Glu Glu Lys Pro Glu Glu Gly
65                  70                  75                  80

Val Thr Gln Pro Glu Glu Thr Pro Glu Gln Pro Val Glu Gly Thr Glu
                85                  90                  95

Glu Glu Gly Lys Gln Glu Ser Glu Ala Ala Pro Glu Thr Pro Ala Val
            100                 105                 110

Gln Pro Lys Pro Glu Glu Gly His Glu Arg Pro Glu Pro Glu Glu Glu
        115                 120                 125

Glu Glu Lys Lys Glu Glu Gly Gly Gly Phe Pro Thr Ala Ala Val Ala
```

```
            130                 135                 140
Gly Gly Val Gly Gly Val Leu Leu Ile Ala Ala Val Gly Gly Val
145                 150                 155                 160

Ala Ala Phe Thr Ser Gly Gly Gly Ala Gly Ala Gln Glu Ala Glu
                165                 170                 175

Gln Val Glu Phe Glu Gly Glu Asp Thr Gly Ala Ala Thr Ala Glu Thr
            180                 185                 190

Pro Glu Ala Asp Thr Val Ile Asp Ile Thr Asp Glu Asp Tyr Trp
            195                 200                 205

Ala Asp Ser Gly Asp Ile Gln
            210         215

<210> SEQ ID NO 34
<211> LENGTH: 16
<212> TYPE: PRT
<213> ORGANISM: Chicken

<400> SEQUENCE: 34

Val Pro Ser Thr Thr Pro Val Glu Asn Gln His Val His Pro Tyr Ser
1               5                   10                  15

<210> SEQ ID NO 35
<211> LENGTH: 15
<212> TYPE: PRT
<213> ORGANISM: Chicken

<400> SEQUENCE: 35

Val Pro Ser Thr Thr Pro Val Glu Asn Gln His His Pro Tyr Ser
1               5                   10                  15

<210> SEQ ID NO 36
<211> LENGTH: 15
<212> TYPE: PRT
<213> ORGANISM: Chicken

<400> SEQUENCE: 36

Met Gly Arg Lys Gly Arg Ser Phe Tyr Tyr Gly Gly Tyr Pro Ser
1               5                   10                  15

<210> SEQ ID NO 37
<211> LENGTH: 16
<212> TYPE: PRT
<213> ORGANISM: Chicken

<400> SEQUENCE: 37

Tyr Gly Arg Lys Gly Arg Ser Phe Tyr Tyr Gly Gly Tyr Pro Ser Gly
1               5                   10                  15

<210> SEQ ID NO 38
<211> LENGTH: 14
<212> TYPE: PRT
<213> ORGANISM: Chicken

<400> SEQUENCE: 38

Tyr Pro Ser Tyr Ser Trp Ser Tyr Pro Ala Tyr Thr Arg Val
1               5                   10

<210> SEQ ID NO 39
<211> LENGTH: 13
<212> TYPE: PRT
<213> ORGANISM: Chicken

<400> SEQUENCE: 39
```

```
Tyr Pro Ser Tyr Ser Ser Tyr Pro Ala Tyr Thr Arg Val
1               5                   10

<210> SEQ ID NO 40
<211> LENGTH: 15
<212> TYPE: PRT
<213> ORGANISM: Chicken

<400> SEQUENCE: 40

Gly Lys Arg Met Tyr Ser Thr Gly Tyr Tyr Gly Tyr Gly Tyr Pro
1               5                   10                  15

<210> SEQ ID NO 41
<211> LENGTH: 10
<212> TYPE: PRT
<213> ORGANISM: Chicken

<400> SEQUENCE: 41

Lys Arg Met Tyr Ser Thr Gly Tyr Gly Pro
1               5                   10

<210> SEQ ID NO 42
<211> LENGTH: 12
<212> TYPE: PRT
<213> ORGANISM: Chicken

<400> SEQUENCE: 42

Ser Phe Ser Pro Val Ala Pro Gln Glu Leu Phe Leu
1               5                   10

<210> SEQ ID NO 43
<211> LENGTH: 26
<212> TYPE: DNA
<213> ORGANISM: Artificial Sequence
<220> FEATURE:
<223> OTHER INFORMATION: EP006

<400> SEQUENCE: 43
ttggatcccg aattgcaccc cattcc                                           26

<210> SEQ ID NO 44
<211> LENGTH: 26
<212> TYPE: DNA
<213> ORGANISM: Artificial Sequence
<220> FEATURE:
<223> OTHER INFORMATION: EP007

<400> SEQUENCE: 44
ttgaattctg aatgtcgccg ctgtcg                                           26
```

NUCLEIC ACIDS ENCODING RECOMBINANT 56 AND 82 KDA ANTIGENS FROM GAMETOCYTES OF *EIMERIA MAXIMA* AND THEIR USES

The present application is a divisional of U.S. Ser. No. 10/483,159, filed Sep. 13, 2004, now U.S. Pat. No. 7,423,137, issued Sep. 9, 2008, a §371 national stage of PCT International Application No. PCT/US02/21233, filed Jul. 3, 2002, which claims the benefit of U.S. Provisional Application No. 60/303,699, filed Jul. 6, 2001, the content of which are hereby incorporated by reference into this application.

Throughout this application various publications are referenced in parenthesis. Full citations for these publications may be found listed in alphabetical order at the end of the specification immediately preceding the claims. The disclosures of these publications in their entireties are hereby incorporated by reference into this application in order to more fully describe the state of the art to which this invention pertains.

BACKGROUND OF THE INVENTION

The organisms which cause the disease known as "coccidiosis" in chickens belong to the phylum Apicomplexa, class Sporozoa, subclass Coccidia, order Eucoccidia, suborder Eimeriorina, family Eimeriidae, genus *Eimeria*. Within the *Eimerian* genus there are many species, several of which are pathogenic in chickens. The species of major concern to the chicken industry are *Eimeria tenella, Eimeria maxima, Eimeria acervulina, Eimeria necatrix* and *Eimeria brunetti*.

Coccidiosis has become a major economic problem in the chicken industry over the past several decades, mainly due to the overcrowding of chicken houses and the development of drug resistance by the parasite. The rearing of chickens under crowded conditions on a litter floor provides optimal conditions for the growth and spread of *Eimeria* parasites. Under such circumstances, sanitary control is impossible and the farmer must rely on the effectiveness of coccidiostat drugs. However, drugs must be kept in the feed at all times, shuttle programs must be used to avoid the appearance of drug resistance strains of *Eimeria*, and certain drugs have costly side effects. Furthermore, these coccidiostats also have antibacterial effects and therefore are considered to be in-feed antibiotics. Recently the European Union has decided to ban the use of all in-feed antibiotics in the chicken industry including anticoccidial drugs. Thus, the only viable approach to the control of coccidiosis in the future is by vaccine development.

The *Eimeria* parasite undergoes a complex life cycle in the mucosa of the intestinal tract. This life cycle is very similar to that of the other hemosporidian parasites (i.e. *plasmodium, babesia*, etc.) except for the lack of an arthropod vector. Oocysts sporulate on the litter floor producing four sporocysts, each containing two sporozoites (thus belonging to the class sporozoa). The oocysts are ingested by the chicken, and the sporocysts are released by the mechanical grinding of the gizzard. The sporozoites are then released from the sporocysts due to the digestion of the sporocyst wall by proteolytic enzymes in the intestine. Mobile sporozoites then invade lymphocytes and go on to invade epithelial cells where the asexual cycle begins. The parasite goes through 2-4 cycles of replication and division (each species having a defined number of divisions) leading to the production of large numbers of daughter merozoites. After the final cycle of merozoite production the sexual cycle begins with the production of the macrogametocyte (female) and microgametocyte (male). The macrogametocyte is characterized by the production of wall forming bodies, while microgametocytes contain the components involved in the formation of microgametes, which bud off from the surface of the intracellular parasite. Microgametes are flagellated and are responsible for the fertilization of the macrogamete. A zygote is formed which matures into the oocyst by fusion of the wall forming bodies and condensation of the nucleus. Oocysts are secreted in the feces, thus completing the cycle.

Over the past several years, native antigens from the sexual (gametocyte) stages of *Eimeria maxima* have been used to immunize laying hens. Offspring chicks were consequently vaccinated via maternal immunity (protective maternal antibody). Three major protective antigens have previously been identified in *E. maxima* gametocytes having molecular weights of 250, 82 and 56 kDa (EP Patent No. 0 256 536, U.S. Pat. No. 5,496,550, and U.S. Pat. No. 5,932,225). EP Patent No. 0 256 536, U.S. Pat. No. 5,496,550, and U.S. Pat. No. 5,932,225 are hereby incorporated by reference into this application in order to more fully describe the state of the art to which this invention pertains. It was shown that these antigens are well conserved amongst *Eimeria* species (Wallach 1995) and can cross protect against the 3 major species that cause coccidiosis in broiler chickens, *E. maxima, E. tenella* and *E. acervulina*. More recently, it was shown that in floor pen trials, chicks from hens vaccinated with these native gametocyte antigens were protected against *Eimeria* under field conditions (Wallach 1996). This protection acts to lower the peak in oocyst shedding to a level which does not cause any damaging effect on the performance of the broiler chicken. Based on the above results it was concluded that these antigens are effective against coccidiosis in chickens and also have the potential for use against coccidiosis in other domestic animals including turkeys, geese, sheep, cattle, pigs and fish.

These three antigens were also characterized at the molecular level. Cell free translation experiments were carried out to identify the RNA molecules that encode them (Mencher er al.). cDNA molecules that encode these antigens were cloned by immunoscreening of a cDNA library made in the expression vector lambda zap (4, U.S. Pat. No. 5,932, 225). By this approach, the gene encoding the 250 kDa antigen was cloned and sequenced. The clone pEM 250/14 was partially sequenced in U.S. Pat. Nos. 5,932,225 and 5,496, 550. FIG. 13a of the subject application reproduces FIG. 11 of U.S. Pat. Nos. 5,932,225 and 5,496,550, which portrays the DNA sequence of the first 293 nucleotides of clone pEM 250/14. FIG. 13b of the subject application reproduces FIG. 12 of U.S. Pat. Nos. 5,932,225 and 5,496,550, which shows the DNA sequence of the last 196 nucleotides of clone pEM 250/14. Also, in in U.S. Pat. Nos. 5,932,225 and 5,496,550, the putative genes encoding the 56 and 82 kDa antigens were cloned and sequenced.

Subsequently, Fried et al. sequenced the entire pEM 250/14 clone and found that the antigen had a molecular weight of 230 kDa rather than 250 kDa as had been previously thought. Fried et al. found that the 230 kDa gene contains highly repetitive motifs and that these repeats are contained throughout the entire gene (Fried et al.). This clone was expressed in bacteria using the pATH plasmid vector and it was shown that it is recognized by convalescent chicken sera taken 14 days post infection with *E. maxima*. Finally, it was shown that this gene is expressed only in the macrogametocyte stage and by immunofluorescence was found to be located in the wall forming bodies of the macrogamete (Fried et al.).

cDNA clones encoding the 56 and 82 kDa antigens were also obtained by screening the library with polyclonal antibodies as well as a monoclonal antibody against the 56 kDa antigen. This monoclonal antibody was previously shown to provide passive immunity to naive chicks (Wallach 1990). A few clones were obtained and analyzed. One of the clones was found to encode a small 10 kDa antigen and therefore was not the desired clone. Another clone was found to contain only a small part of the open reading frame (ORF) and by northern blotting was shown to hybridize with two mRNAs of about the expected size for the 56 and 82 kDa antigens. It was therefore concluded that this was the desired clone. Genomic libraries were then screened to obtain the full length clone. However, due to the highly repetitive GCA motifs in this clone, it was not possible to specifically isolate the full length clone. Attempts to clone the full length cDNA molecule were also not successful due to these repeats. Finally, attempts to express the partial cDNA clones in bacteria failed as well probably due to their unusual sequences and a reasonable level of gene expression was not obtained. It has previously been shown that the 56 and 82 kDa antigens are glycosylated (U.S. Pat. No. 5,932,225). This is based on their strong reactivity with Soybean lectin. Therefore, glycosylation may be required in order to obtain good expression of these genes and for proper conformation of the gene products.

In addition to the 56, 82 and 230 kDa antigens, a 14 kDa antigen obtained from highly purified fractions of oocyst walls has been proposed as a possible candidate for vaccines against coccidiosis (Eschenbacher et al.). However, this hypothesis has not been explored.

Several laboratories have been working on a subunit vaccine against coccidiosis. Most of these researchers have focused their efforts on the extracellular asexual stages of the life cycle, in particular the sporozoite and merozoite stages which are considered to be the most vulnerable to immune attack. In a previous study it was found that sporozoite extracts from *E. tenella* could induce in broilers protection against challenge infections against this parasite for up to 7 weeks of age (Karkhanis et al.). Work carried out using monoclonal antibodies against antigens from sporozoites of *E. tenella* led to the identification of a 25,000 molecular weight antigen which was cloned and sequenced (Eur. Patent publication No. 0 164 176, Dec. 11, 1985). Several other sporozoite genes were identified and their recombinant antigens or the transformed bacteria themselves were tested for protective immunity (Danforth et al.). The results indicated that these recombinants were only able to provide a relatively low level of protection against challenge infection with *Eimeria* and did not always prevent the appearance of significant lesions.

A vaccine using antigens from the merozoite stage has also been tested (European patent publication No. 0 135 073). Using these antigens to immunize young broiler chicks, it was once again found that the protection afforded was relatively low (Danforth et al.).

In 1993, it was found that there was a correlation between protective maternal immunity with the appearance of maternal antibodies against a 230 kDa merozoite (as opposed to gametocyte) antigen of *Eimeria maxima* (Smith et al.). This protection was often over 90% and was found to occur even when the maternal antibody level was relatively low (although reactivity with the 230 kDa protein remained strong). It was also found that a very small quantity of the native 230 kDa merozoite antigen cut out of an SDS-PAGE gel could induce a significant (60%) level of protective maternal immunity against infection with *E. maxima* in offspring chicks. Furthermore, Western blotting showed that this protein was expressed in both merozoites and sporozoites of *E. maxima* and is also well conserved between *Eimeria* species.

SUMMARY OF THE INVENTION

The present invention provides the nucleic acid encoding two of the major *Eimeria maxima* gametocyte antigens having molecular weights of 56 and 82 kDa.

The subject invention also provides a 30 kDa protein from *Eimeria maxima* gametocytes having at the N-terminal end the amino acid sequence shown by SEQ. ID NO. 35.

The subject invention also provides a 30 kDa protein from *Eimeria maxima* gametocytes having at the N-terminal end the amino acid sequence shown by SEQ. ID NO. 42.

The subject invention also provides a 14 kDa protein from *Eimeria maxima* gametocytes having at the N-terminal end the amino acid sequence shown by SEQ. ID NO. 37.

The subject invention also provides a 14 kDa protein from *Eimeria maxima* gametocytes having at the N-terminal end the amino acid sequence shown by SEQ. ID NO. 39.

The subject invention also provides a 14 kDa protein from *Eimeria maxima* gametocytes having at the N-terminal end the amino acid sequence shown by SEQ. ID NO. 41.

The subject invention also provides a vaccine against coccidiosis comprising the recombinant 56 kDa antigen alone or in combination with any of the aforementioned proteins.

The subject invention also provides a vaccine against coccidiosis comprising the recombinant 82 kDa antigen alone or in combination with any of the aforementioned proteins.

The subject invention also provides a method of immunizing an subject against infection by *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising the step of administering to the subject any of the aforementioned vaccines.

BRIEF DESCRIPTION OF THE FIGURES

FIG. 2 depicts a two-dimensional (2D) SDS-PAGE gel of affinity purified native gametocyte antigens after immunoblotting and silver staining. Molecular weight marker proteins are indicated.

FIG. 4 depicts the complete DNA sequence of the 56 kDa gametocyte antigen. The amino terminus as well as internal tryptic peptide fragments are designated. In addition, the predicted initiator methionine and signal peptide cleavage site are shown. The coding sequence, its complement and amino acid sequences are shown (SEQ. ID. NOs. 1-3).

FIG. 5 depicts the complete DNA sequence of the 82 kDa gametocyte antigen. The amino terminus as well as internal tryptic peptide fragments are designated. In addition, the predicted initiator methionine and signal peptide cleavage site are shown. The coding sequence, its complement and amino acid sequences are shown (SEQ. ID. NOs. 4-6).

FIG. 9 depicts an immunoblot showing reactivity of the anti polyhistidine antibody and chicken anti-APGA with proteins expressed by IPTG induced and non-induced (control) bacteria containing the 56 kDa cDNA clone in pTrcHisB. As a further negative control, bacteria that were transformed with the pTrcHisB plasmid containing no insert were tested. Finally, native APGA was used as a positive control for the blot with the anti APGA antiserum. The sizes of the protein marker bands are indicated. Arrows show the positions of the 41 kDa recombinant and 56 and 82 kDa native proteins.

FIG. 12 depicts DNA sequence alignment of the 230 kDa cDNA *E. maxima* clone with a homologous DNA sequence from patent WO 90/00403 showing 60% homology (SEQ. ID. NOs. 26-27).

FIG. 13A depicts the DNA sequence of the first 293 nucelotides of clone pEM 250/14. The coding sequence and its amino acid sequences are shown (SEQ. ID. NOs. 28-29). FIG. 13B depicts the DNA sequence of the last 196 nucelotides of clone pEM 250/14. The coding sequence and its amino acid sequences are shown (SEQ. ID. NOs. 30-31).

FIG. 15 DNA and encoded amino acid sequence of the expressed protein fragment from the 250 kDa asexual stage protein (SEQ. ID NOS. 32-33).

FIG. 19 Anti-r82 recognition of gametocyte and wall antigens in *Eimeria maxima*.

FIG. 20A & FIG. 20B Alignment of the N-terminus sequence of the oocyst wall proteins to the 56 kDa and 82 kDa gametocyte antigens (SEQ. ID NOS. 34-42). FIG. 20C 30 kDa oocyst wall protein.

DETAILED DESCRIPTION OF THE INVENTION

Figure 1:
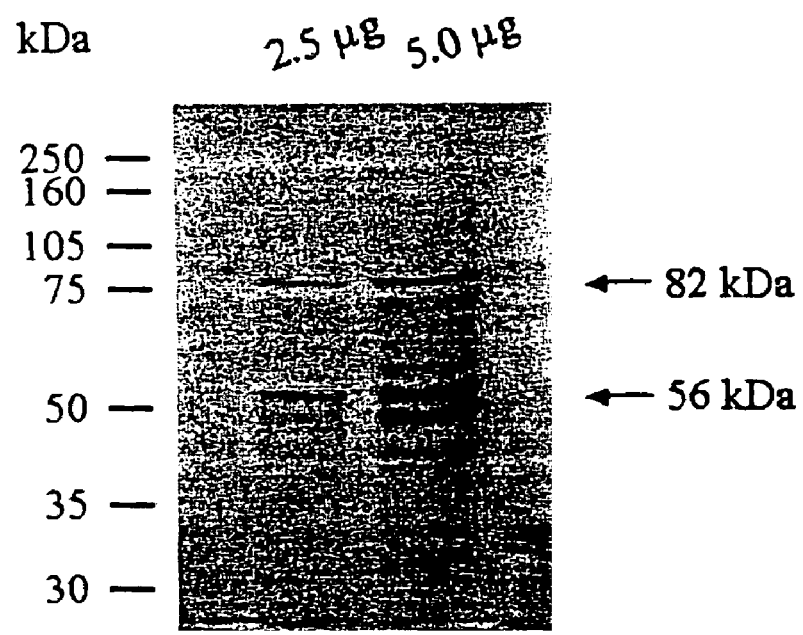
FIG. 1 depicts a Coomassie stained SDS PAGE gel of affinity purified native gametocyte antigens. Arrows point to the 56 and 82 kDa antigens. Molecular weight marker proteins are indicated.

The subject invention provides an isolated nucleic acid comprising a nucleotide sequence encoding a 56 kDa polypeptide from Gametocytes of *Eimeria maxima*, or encoding a homolog of the polypeptide, or a complement of the nucleic acid.

In one embodiment, the polypeptide has the amino acid sequence shown in FIG. 4 (SEQ. ID. NO. 3).

In another embodiment, the homolog of the polypeptide has at least 50% identity to the polypeptide having the sequence shown as SEQ. ID. NO. 3.

In an additional embodiment, the homolog of the polypeptide has at least 60% identity to the polypeptide having the sequence shown as SEQ. ID. NO. 3.

In a further embodiment, the homolog of the polypeptide has at least 70% identity to the polypeptide having the sequence shown as SEQ. ID. NO. 3.

In an added embodiment, the homolog of the polypeptide has at least 75% identity to the polypeptide having the sequence shown as SEQ. ID. NO. 3.

In yet another embodiment, the homolog of the polypeptide has at least 80% identity to the polypeptide having the sequence shown as SEQ. ID. NO. 3.

In a further embodiment, the homolog of the polypeptide has at least 85% identity to the polypeptide having the sequence shown as SEQ. ID. NO. 3.

In one embodiment, the homolog of the polypeptide has at least 90% identity to the polypeptide having the sequence shown as SEQ. ID. NO. 3.

In another embodiment, the homolog of the polypeptide has at least 93% identity to the polypeptide having the sequence shown as SEQ. ID. NO. 3.

In an additional embodiment, the homolog of the polypeptide has at least 95% identity to the polypeptide having the sequence shown as SEQ. ID. NO. 3.

In a further embodiment, the homolog of the polypeptide has at least 97% identity to the polypeptide having the sequence shown as SEQ. ID. NO. 3.

In yet another embodiment, the homolog of the polypeptide has at least 99% identity to the polypeptide having the sequence shown as SEQ. ID. NO. 3.

In an additional embodiment, the nucleotide sequence has at least 50% identity to the nucleotide sequence starting at nucleotide No. 103 and ending at nucleotide No. 1529 shown in FIG. 4 (SEQ. ID. NO. 1.)

In another embodiment, the nucleotide sequence has at least 60% identity to the nucleotide sequence starting at nucleotide No. 103 and ending at nucleotide No. 1529 shown as SEQ. ID. NO. 1.

In a further embodiment, the nucleotide sequence has at least 70% identity to the nucleotide sequence starting at nucleotide No. 103 and ending at nucleotide No. 1529 shown as SEQ. ID. NO. 1.

In one embodiment, the nucleotide sequence has at least 75% identity to the nucleotide sequence starting at nucleotide No. 103 and ending at nucleotide No. 1529 shown as SEQ. ID. NO. 1.

In another embodiment, the nucleotide sequence has at least 80% identity to the nucleotide sequence starting at nucleotide No. 103 and ending at nucleotide No. 1529 shown as SEQ. ID. NO. 1.

In an added embodiment, the nucleotide sequence has at least 85% identity to the nucleotide sequence starting at nucleotide No. 103 and ending at nucleotide No. 1529 shown as SEQ. ID. NO. 1.

In one embodiment, the nucleotide sequence has at least 90% identity to the nucleotide sequence starting at nucleotide No. 103 and ending at nucleotide No. 1529 shown as SEQ. ID. NO. 1.

In a further embodiment, the nucleotide sequence has at least 93% identity to the nucleotide sequence starting at nucleotide No. 103 and ending at nucleotide No. 1529 shown as SEQ. ID. NO. 1.

In another embodiment, the nucleotide sequence has at least 95% identity to the nucleotide sequence starting at nucleotide No. 103 and ending at nucleotide No. 1529 shown as SEQ. ID. NO. 1.

In an added embodiment, the nucleotide sequence has at least 97% identity to the nucleotide sequence starting at nucleotide No. 103 and ending at nucleotide No. 1529 shown as SEQ. ID. NO. 1.

In one embodiment, the nucleotide sequence has at least 99% identity to the nucleotide sequence starting at nucleotide No. 103 and ending at nucleotide No. 1529 shown as SEQ. ID. NO. 1.

In a further embodiment, the nucleic acid is a DNA molecule.

In yet another embodiment, the DNA molecule is a cDNA molecule.

In an added embodiment, the nucleic acid has the nucleotide sequence starting at nucleotide No. 103 and ending at nucleotide No. 1529 shown in FIG. 4 (SEQ. ID. NO. 1).

In another embodiment, the nucleic acid is an RNA molecule.

In one embodiment, the isolated nucleic acid is operatively linked to a promoter of RNA transcription.

The subject invention also includes a vector comprising an isolated nucleic acid comprising a nucleotide sequence encoding a 56 kDa polypeptide from Gametocytes of *Eimeria maxima*, or encoding a homolog of the polypeptide, or a complement of the nucleic acid.

In one embodiment, the vector comprises the nucleic acid having the nucleotide sequence starting at nucleotide No. 103 and ending at nucleotide No. 1529 shown in FIG. 4 (SEQ. ID. NO. 1).

In another embodiment, the vector is a plasmid.

In a further embodiment, the plasmid comprises the nucleic acid having the nucleotide sequence starting at nucleotide No. 103 and ending at nucleotide No. 1529 shown in FIG. 4 (SEQ. ID. NO. 1).

In an additional embodiment, the plasmid comprises an isolated nucleic acid comprising a nucleotide sequence encoding a 56 kDa polypeptide from Gametocytes of *Eimeria maxima*, or encoding a homolog of the polypeptide, or a complement of the nucleic acid.

In yet another embodiment, the plasmid is the plasmid designated 56TRCHisb1 plasmid (Australian Government Analytical Laboratories Accession No. NM01/22400).

The subject invention also encompasses a host cell comprising a vector which comprises an isolated nucleic acid comprising a nucleotide sequence encoding a 56 kDa polypeptide from Gametocytes of *Eimeria maxima*, or encoding a homolog of the polypeptide, or a complement of the nucleic acid.

In one embodiment, the host cell comprises a vector comprising a nucleic acid having the nucleotide sequence starting at nucleotide No. 103 and ending at nucleotide No. 1529 shown in FIG. 4 (SEQ. ID. NO. 1).

In another embodiment, the host cell is selected from the group consisting of a bacterial cell; a plant cell; an insect cell; and a mammalian cell.

The subject invention additionally presents a transformed cell comprising an isolated nucleic acid comprising a nucleotide sequence encoding a 56 kDa polypeptide from Gametocytes of *Eimeria maxima*, or encoding a homolog of the polypeptide, or a complement of the nucleic acid.

In one embodiment, the transformed cell is the transformed cell designated clone 56TRCHisb1 in bacteria (Australian Government Analytical Laboratories Accession No. NM01/22401).

A plasmid encoding the 56 kDa antigen was deposited with the Australian Government Analytical Laboratories, Pymble, Australia, on Jun. 26, 2001, under Accession No. NM01/22400. The bacterial cell transformed with the 56 kDa antigen was deposited with the Australian Government Analytical Laboratories, Pymble, Australia, on Jun. 26, 2001, under Accession No. NM01/22401. Both deposits were made according to the Budapest Treaty on the International Recognition of the Deposit of Microorganisms for the Purposes of Patent Procedure.

In an added embodiment, the transformed cell further comprises a 56 kDa polypeptide from Gametocytes of *Eimeria maxima*, or a homolog of the polypeptide.

The subject invention further contains a method of producing a recombinant 56 kDa polypeptide from Gametocytes of *Eimeria maxima* comprising culturing a transformed cell comprising an isolated nucleic acid comprising a nucleotide sequence encoding a 56 kDa polypeptide from Gametocytes of *Eimeria maxima*, or encoding a homolog of the polypeptide, or a complement of the nucleic acid and isolating the recombinant 56 kDa polypeptide from Gametocytes of *Eimeria maxima*. The recombinant polypeptide produced by this method is also encompassed by the subject invention.

The subject invention also provides a vaccine against *Eimeria tenella, Eimeria maxima, Eimeria acervulina, Eimeria necatrix* or *Eimeria brunetti, Eimeria praecox, Eimeria mitis* or a microorganism expressing an immunologically cross-reactive antigen, comprising the isolated nucleic acid comprising a nucleotide sequence encoding a 56 kDa polypeptide from Gametocytes of *Eimeria maxima*, or encoding a homolog of the polypeptide, or a complement of the nucleic acid.

In one embodiment of the vaccine, the isolated nucleic acid is a plasmid.

In addition, the subject invention presents a vaccine against *Eimeria tenella, Eimeria maxima, Eimeria acervulina, Eimeria necatrix* or *Eimeria brunetti, Eimeria praecox, Eimeria mitis* or a microorganism expressing an immunologically cross-reactive antigen, comprising a recombinant 56 kDa polypeptide from Gametocytes of *Eimeria maxima* produced by culturing a transformed cell comprising an isolated nucleic acid comprising a nucleotide sequence encoding a 56 kDa polypeptide from Gametocytes of *Eimeria maxima*, or encoding a homolog of the polypeptide, or a complement of the nucleic acid and isolating the recombinant 56 kDa polypeptide from Gametocytes of *Eimeria maxima*.

In another embodiment, the vaccine is comprised of a mixture of the isolated nucleic acid of the subject invention and the recombinant polypeptide of the subject invention.

In another embodiment, the vaccine is comprised of a mixture of the isolated nucleic acid of the subject invention, the recombinant polypeptide of the subject invention and a plasmid comprising the isolated nucleic acid comprising a nucleotide sequence encoding a 56 kDa polypeptide from Gametocytes of *Eimeria maxima*.

In an added embodiment, the vaccine further comprises a second antigen.

In one embodiment, the second antigen is selected from the group consisting of a nucleic acid coding for an antigen from *Eimeria maxima*, a plasmid comprising such a nucleic acid, and a polypeptide coded by such a nucleic acid.

In another embodiment, the second antigen is selected from the group consisting of a 30 kDa protein from *Eimeria maxima* gametocytes having at the N-terminal end the amino acid sequence shown as SEQ. ID NO. 35, or SEQ. ID NO. 42 or a 14 kDa protein from *Eimeria maxima* gametocytes having at the N-terminal end the amino acid sequence shown as SEQ. ID NO. 37, SEQ. ID NO. 39 or SEQ. ID NO. 41.

In yet another embodiment, the second antigen is a nucleic acid having the nucleotide sequence shown in Seq. ID. No. 4, a plasmid comprising the nucleic acid or a polypeptide coded by the nucleic acid.

In a further embodiment, the vaccine further comprises a third antigen.

The subject invention also provides a vaccine wherein the third antigen is a 230 kDa sporozoite/merozoite antigen from *E. maxima*.

The 230 kDa antigen was isolated from purified *E. maxima* sporozoites which are present in sporulated oocysts (see life cycle above). The isolation procedure involved extraction of proteins from the sporulated oocysts and separation of the extracted proteins on a DEAE-sephacel anion-exchange column. This was followed by SDS-PAGE of the peak fractions and Western blotting to identify the 230 kDa antigen. Furthermore, protective maternal antisera both from vaccinated hens and offspring chicks were used to confirm the identity of the purified antigen. Finally, the 230 kDa protein was isolated from a PVDF membrane filter for carrying out protein sequencing and cloning.

The amino terminal and tryptic peptide digest products of the 230 kDa antigen were sequenced. The sequences from the tryptic digest were used to design degenerate PCR oligonucleotide primers. The primers were used in RACE (rapid amplification of cDNA ends) PCR to amplify partial gene products. From the sequences of these products, gene specific primers were designed and used in RACE PCR to define the 3' and 5' ends of the mRNA. A full length 7 kilobase cDNA clone encoding the antigen was then amplified by PCR using gene specific primers designed to the 5' and 3' ends. This clone was fully sequenced and shown to contain the correct DNA sequence at its 5' end when compared to the amino acid sequence of the N-terminus of the native protein. Thus, this nucleic acid sequence encoded the protective 230 kDa sporozoite/merozoite antigen and could now be used to produce recombinant antigen for vaccination of chickens against coccidiosis.

A plasmid encoding the 230 kDa antigen was deposited with the Australian Government Analytical Laboratories, Pymble, Australia, on Jun. 26, 2001, under Accession No. NM01/22396. The bacterial cell transformed with the 230 kDa antigen was deposited with the Australian Government Analytical Laboratories, Pymble, Australia, on Jun. 26, 2001, under Accession No. NM01/22397. Both deposits were made according to the Budapest Treaty on the International Recognition of the Deposit of Microorganisms for the Purposes of Patent Procedure.

It was previously thought that the antigen from the sporozoites/merozoites of *E. maxima* was a 230 kDa antigen. However, our subsequent studies have revealed that the antigen actually is a 250 kDa antigen of the sporozoites/merozoites of *E. maxima*.

In an additional embodiment, the third antigen is a nucleic acid having the nucleotide sequence shown in FIG. 12 (SEQ. ID. NO. 26), a plasmid comprising the nucleic acid, or a polypeptide coded by the nucleic acid.

In still another embodiment, the vaccine further comprises a fourth antigen.

In one embodiment, the fourth antigen is a polypeptide from Gametocytes of *Eimeria maxima* having a molecular weight from 230 kDa to 270 kDa, a nucleotide sequence encoding the polypeptide, or a plasmid comprising the nucleotide sequence.

In a further embodiment, the antigen comprises a polypeptide having the amino acid sequence shown in FIG. 13*a* (SEQ. ID. NO. 29) at its 5' end or the amino acid sequence shown in FIG. 13*b* (SEQ. ID. NO. 31) at its 3' end.

The subject invention also provides a method of immunizing a subject against infection by *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising the step of administering to the subject the vaccine of the subject invention.

In one embodiment, the subject is a species selected from the group consisting of cattle, sheep, pigs and fish.

In another embodiment, the subject is an avian species.

In a further embodiment, the avian species is selected from the group consisting of chickens, turkeys, geese, ducks, bantams, quail and pigeons.

In an additional embodiment, the avian species is chickens.

In one embodiment, the administering step comprises spraying the vaccine into the nostrils of the subject.

In a further embodiment, the administration comprises intravenous, intramuscular or intraperitoneal injection.

In another embodiment, the administration is performed in ovo.

In a further embodiment, the administration is to the air sac of an egg, thus contacting an embryo with the vaccine.

The subject invention also contains a fertilized egg from an avian species having an air sac which is inoculated with the vaccine of the subject invention, which vaccine is capable of inducing before or immediately after hatching an immune response in the embryo against a virulent form of *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen.

In one embodiment, the avian species is selected from the group consisting of chickens, ducks, turkeys, geese, bantams, quail and pigeons.

In another embodiment, the avian species is chickens.

The subject invention additionally provides an isolated nucleic acid comprising a nucleotide sequence encoding a 82 kDa polypeptide from Gametocytes of *Eimeria maxima*, or encoding a homolog of the polypeptide, or a complement of the nucleic acid.

Figure 5:
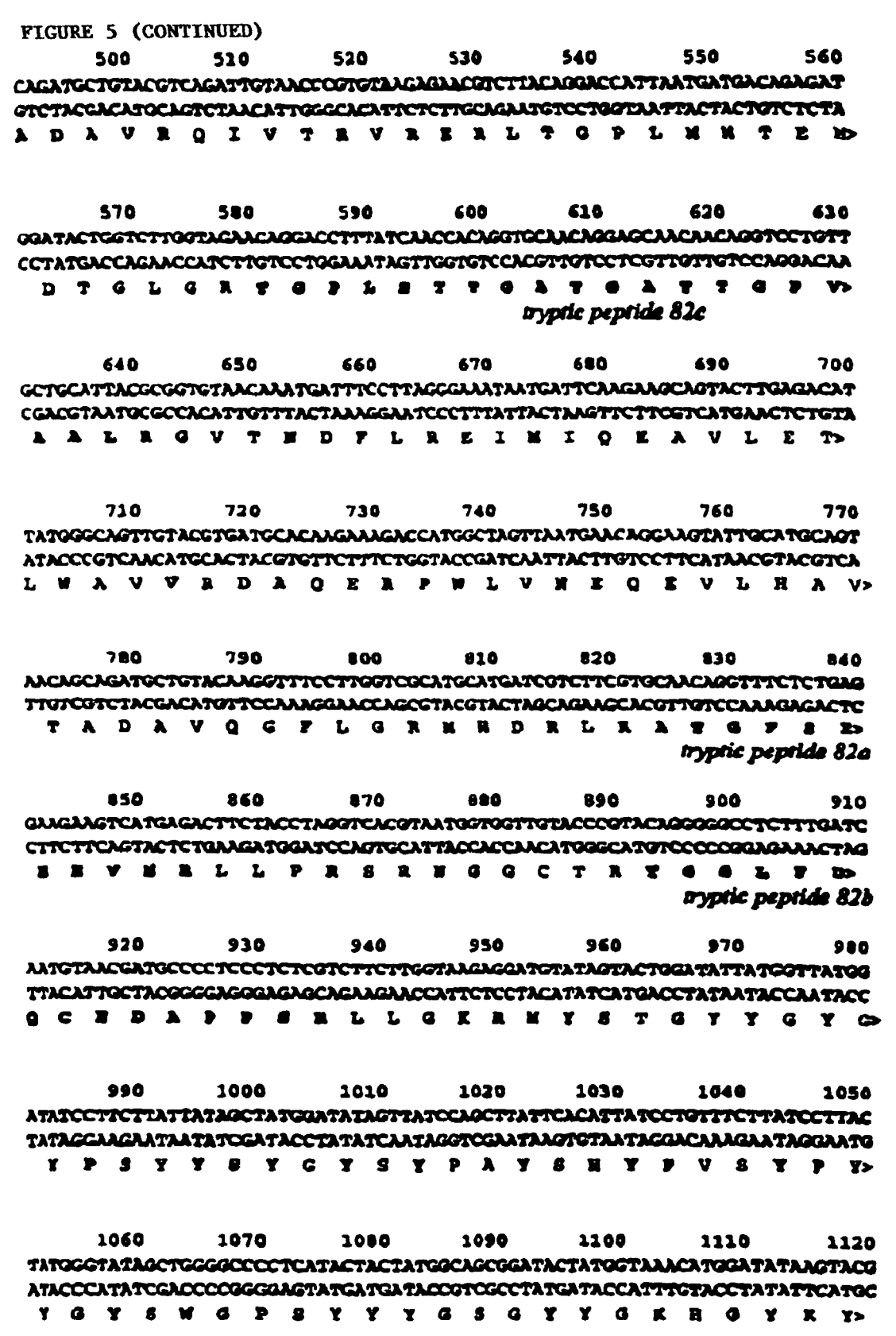

In one embodiment, the polypeptide has the amino acid sequence shown in FIG. 5 (SEQ. ID. NO. 6).

In another embodiment, the homolog of the polypeptide has at least 50% identity to the polypeptide having the sequence shown as SEQ. ID. NO. 6.

In an additional embodiment, the homolog of the polypeptide has at least 60% identity to the polypeptide having the sequence shown as SEQ. ID. NO. 6.

In a further embodiment, the homolog of the polypeptide has at least 70% identity to the polypeptide having the sequence shown as SEQ. ID. NO. 6.

In another embodiment, the homolog of the polypeptide has at least 75% identity to the polypeptide having the sequence shown as SEQ. ID. NO. 6.

In yet another embodiment, the homolog of the polypeptide has at least 80% identity to the polypeptide having the sequence shown as SEQ. ID. NO. 6.

In an added embodiment, the homolog of the polypeptide has at least 85% identity to the polypeptide having the sequence shown as SEQ. ID. NO. 6.

In one embodiment, the homolog of the polypeptide has at least 90% identity to the polypeptide having the sequence shown as SEQ. ID. NO. 6.

In a further embodiment, the homolog of the polypeptide has at least 93% identity to the polypeptide having the sequence shown as SEQ. ID. NO. 6.

In yet another embodiment, the homolog of the polypeptide has at least 95% identity to the polypeptide having the sequence shown as SEQ. ID. NO. 6.

In one embodiment, the homolog of the polypeptide has at least 97% identity to the polypeptide having the sequence shown as SEQ. ID. NO. 6.

In an additional embodiment, the homolog of the polypeptide has at least 99% identity to the polypeptide having the sequence shown as SEQ. ID. NO. 6.

In an additional embodiment, the nucleotide sequence has greater than 50% identity to the nucleotide sequence starting at nucleotide No. 100 and ending at nucleotide No. 1886 shown in FIG. 5 (SEQ. ID. NO. 4).

In another embodiment, the nucleotide sequence has greater than 60% identity to the nucleotide sequence starting at nucleotide No. 100 and ending at nucleotide No. 1886 shown as SEQ. ID. NO. 4.

In a further embodiment, the nucleotide sequence has at least 70% identity to the nucleotide sequence starting at nucleotide No. 100 and ending at nucleotide No. 1886 shown as SEQ. ID. NO. 4.

In an additional embodiment, the nucleotide sequence has at least 75% identity to the nucleotide sequence starting at nucleotide No. 100 and ending at nucleotide No. 1886 shown as SEQ. ID. NO. 4.

In another embodiment, the nucleotide sequence has at least 80% identity to the nucleotide sequence starting at nucleotide No. 100 and ending at nucleotide No. 1886 shown as SEQ. ID. NO. 4.

In yet another embodiment, the nucleotide sequence has at least 85% identity to the nucleotide sequence starting at nucleotide No. 100 and ending at nucleotide No. 1886 shown as SEQ. ID. NO. 4.

In one embodiment, the nucleotide sequence has at least 90% identity to the nucleotide sequence starting at nucleotide No. 100 and ending at nucleotide No. 1886 shown as SEQ. ID. NO. 4.

In an additional embodiment, the nucleotide sequence has at least 93% identity to the nucleotide sequence starting at nucleotide No. 100 and ending at nucleotide No. 1886 shown as SEQ. ID. NO. 4.

In another embodiment, the nucleotide sequence has at least 95% identity to the nucleotide sequence starting at nucleotide No. 100 and ending at nucleotide No. 1886 shown as SEQ. ID. NO. 4.

In a further embodiment, the nucleotide sequence has at least 97% identity to the nucleotide sequence starting at nucleotide No. 100 and ending at nucleotide No. 1886 shown as SEQ. ID. NO. 4.

In one embodiment, the nucleotide sequence has at least 99% identity to the nucleotide sequence starting at nucleotide No. 100 and ending at nucleotide No. 1886 shown as SEQ. ID. NO. 4.

In a further embodiment, the nucleic acid is a DNA molecule.

In yet another embodiment, the DNA molecule is a cDNA molecule.

In an added embodiment, the nucleic acid has the nucleotide sequence starting at nucleotide No. 100 and ending at nucleotide No. 1886 shown as SEQ. ID. NO. 4.

In another embodiment, the nucleic acid is an RNA molecule.

In one embodiment, the isolated nucleic acid is operatively linked to a promoter of RNA transcription.

The subject invention also includes a vector comprising an isolated nucleic acid comprising a nucleotide sequence encoding a 82 kDa polypeptide from Gametocytes of *Eimeria maxima*, or encoding a homolog of the polypeptide, or a complement of the nucleic acid.

In one embodiment, the vector comprises the nucleic acid having the nucleotide sequence starting at nucleotide No. 100 and ending at nucleotide No. 1886 shown in FIG. 5 (SEQ. ID. NO. 4).

In another embodiment, the vector is a plasmid.

In a further embodiment, the plasmid comprises the nucleic acid having the nucleotide sequence starting at nucleotide No. 100 and ending at nucleotide No. 1886 shown in FIG. 5 (SEQ. ID. NO. 4).

In an additional embodiment, the plasmid comprises an isolated nucleic acid comprising a nucleotide sequence encoding a 82 kDa polypeptide from Gametocytes of *Eimeria maxima*, or encoding a homolog of the polypeptide, or a complement of the nucleic acid.

In yet another embodiment, the plasmid is the plasmid designated 82TRCHisb8 plasmid (Australian Government Analytical Laboratories, PO Box 385, Pymble, NSW 2073, Australia, Accession No. NM01/22398, deposited on Jun. 26, 2001).

The subject invention also encompasses a host cell comprising a vector which comprises an isolated nucleic acid comprising a nucleotide sequence encoding a 82 kDa polypeptide from Gametocytes of *Eimeria maxima*, or encoding a homolog of the polypeptide, or a complement of the nucleic acid.

In one embodiment, the host cell comprises a vector comprising a nucleic acid having the nucleotide sequence starting at nucleotide No. 100 and ending at nucleotide No. 1886 shown in FIG. 5 (SEQ. ID. NO. 4).

In another embodiment, the host cell is selected from the group consisting of a bacterial cell; a plant cell; an insect cell; and a mammalian cell.

The subject invention additionally presents a transformed cell comprising an isolated nucleic acid comprising a nucleotide sequence encoding a 82 kDa polypeptide from Gametocytes of *Eimeria maxima*, or encoding a homolog of the polypeptide, or a complement of the nucleic acid.

In one embodiment, the transformed cell is the transformed cell designated clone 82TRCHisb8 in bacteria (Australian Government Analytical Laboratories, PO Box 385, Pymble, NSW 2073, Australia, Accession No. NM01/22399, deposited on Jun. 26, 2001).

A plasmid encoding the 82 kDa antigen was deposited with the Australian Government Analytical Laboratories, PO Box 385, Pymble, NSW 2073, Australia, on Jun. 26, 2001, under Accession No. NM01/22398. The bacterial cell transformed with the 82 kDa antigen was deposited with the Australian Government Analytical Laboratories, PO Box 385, Pymble, NSW 2073, Australia, on Jun. 26, 2001, under Accession No. NM01/22399. Both deposits were made according to the Budapest Treaty on the International Recognition of the Deposit of Microorganisms for the Purposes of Patent Procedure.

In an added embodiment, the transformed cell further comprises a 82 kDa polypeptide from Gametocytes of *Eimeria maxima*, or a homolog of the polypeptide.

The subject invention further contains a method of producing a recombinant 82 kDa polypeptide from Gametocytes of *Eimeria maxima* comprising culturing a transformed cell comprising an isolated nucleic acid comprising a nucleotide sequence encoding a 82 kDa polypeptide from Gametocytes of *Eimeria maxima*, or encoding a homolog of the polypeptide, or a complement of the nucleic acid and isolating the recombinant 82 kDa polypeptide from Gametocytes of *Eimeria maxima*. The recombinant polypeptide produced by this method is also encompassed by the subject invention.

The subject invention also provides a vaccine against *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising the isolated nucleic acid comprising a nucleotide sequence encoding a 82 kDa polypeptide from Gametocytes of *Eimeria maxima*, or encoding a homolog of the polypeptide, or a complement of the nucleic acid.

In one embodiment of the vaccine, the isolated nucleic acid is a plasmid.

In addition, the subject invention presents a vaccine against *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising a recombinant 82 kDa polypeptide from Gametocytes of *Eimeria maxima* produced by culturing a transformed cell comprising an isolated nucleic acid comprising a nucleotide sequence encoding a 82 kDa polypeptide from Gametocytes of *Eimeria maxima*, or encoding a homolog of the polypeptide, or a complement of the nucleic acid and isolating the recombinant 82 kDa polypeptide from Gametocytes of *Eimeria maxima*.

In another embodiment, the vaccine is comprised of a mixture of the isolated nucleic acid of the subject invention and the recombinant polypeptide of the subject invention.

In another embodiment, the vaccine is comprised of a mixture of the isolated nucleic acid of the subject invention, the recombinant polypeptide of the subject invention and a plasmid comprising the isolated nucleic acid comprising a nucleotide sequence encoding a 82 kDa polypeptide from Gametocytes of *Eimeria maxima*.

In an added embodiment, the vaccine further comprises a second antigen.

In one embodiment, the second antigen is selected from the group consisting of a nucleic acid coding for an antigen from *Eimeria maxima*, a plasmid comprising such a nucleic acid, and a polypeptide coded by such a nucleic acid.

In another embodiment, the second antigen is selected from the group consisting of a 30 kDa protein from *Eimeria maxima* gametocytes having at the N-terminal end the amino acid sequence shown as SEQ. ID NO. 35, or SEQ. ID NO. 42 or a 14 kDa protein from *Eimeria maxima* gametocytes having at the N-terminal end the amino acid sequence shown as SEQ. ID NO. 37, SEQ. ID NO. 39 or SEQ. ID NO. 41.

The subject invention also provides a method of immunizing a subject against infect-ion by *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising the step of administering to the subject the vaccine of the subject invention.

In one embodiment, the subject is a species selected from the group consisting of cattle, sheep, pigs and fish.

In another embodiment, the subject is an avian species.

In a further embodiment, the avian species is selected from the group consisting of chickens, turkeys, geese, ducks, bantams, quail and pigeons.

In an additional embodiment, the avian species is chickens.

In a further embodiment, the administration comprises intravenous, intramuscular or intraperitoneal injection.

In one embodiment, the administering step comprises spraying the vaccine into the nostrils of the subject.

In another embodiment, the administration is performed in ovo.

In a further embodiment, the administration is to the air sac of an egg, thus contacting an embryo with the vaccine.

The subject invention also contains a fertilized egg from an avian species having an air sac which is inoculated with the vaccine of the subject invention, which vaccine is capable of inducing before or immediately after hatching an immune response in the embryo against a virulent form of *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen.

In one embodiment, the avian species is selected from the group consisting of chickens, ducks, turkeys, geese, bantams, quail and pigeons.

In another embodiment, the avian species is chickens.

The subject invention also provides a recombinant polypeptide, wherein the amino acid sequence is shown as SEQ. ID NO. 3.

The subject invention also provides a recombinant polypeptide, wherein the amino acid sequence is shown as SEQ. ID NO. 6.

The subject invention also provides a 30 kDa protein from *Eimeria maxima* gametocytes having at the N-terminal end the amino acid sequence shown as SEQ. ID NO. 35

The subject invention also provides a 30 kDa protein from *Eimeria maxima* gametocytes having at the N-terminal end the amino acid sequence shown as SEQ. ID NO. 42.

The subject invention also provides a 14 kDa protein from *Eimeria maxima* gametocytes having at the N-terminal end the amino acid sequence shown as SEQ. ID NO. 37.

The subject invention also provides a 14 kDa protein from *Eimeria maxima* gametocytes having at the N-terminal end the amino acid sequence shown as SEQ. ID NO. 39.

The subject invention also provides a 14 kDa protein from *Eimeria maxima* gametocytes having at the N-terminal end the amino acid sequence shown as SEQ. ID NO. 41.

The aforementioned proteins and their corresponding nucleotide sequences can be used in the same manner as described above for the 56 kDa and 82 kDa proteins, including being used to immunize a subject, and to incorporate a plasmid containing a nucleotide sequence encoding the protein into a host cell.

The subject invention also provides a method of conferring upon a newborn subject of an avian species maternal immunity (antibodies) against infection by *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising the step of administering to the mother of the subject at a suitable time prior to the laying of a fertilized egg the vaccine of the subject invention in order to thereby confer protection via maternal immunity against infection by *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, in the newborn subject.

In a further embodiment, the avian species is selected from the group consisting of chickens, turkeys, geese, ducks, bantams, quail and pigeons.

In a further embodiment, the administration comprises intravenous, intramuscular or intraperitoneal injection.

The subject invention also provides a method of reducing the output of *Eimeria* oocysts in feces from a newborn subject of an avian species which comprises the step of administering to the mother of the subject at a suitable time prior to the laying of a fertilized egg the vaccine of the subject invention in order induce an immune response and transmit maternal antibodies to the newborn so that the output of oocysts from the newborn is reduced.

In a further embodiment, the avian species is selected from the group consisting of chickens, turkeys, geese, ducks, bantams, quail and pigeons.

In a further embodiment, the administration comprises intravenous, intramuscular or intraperitoneal injection.

The subject invention also provides a method of immunizing a subject against infection by *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising the step of administering to the subject a live vaccine comprising a living non-virulent micro-organism or live virus that expresses a 56 kDa or 82 kDa polypeptide from the gametocytes of *Eimeria maxima*.

In one embodiment, the live virus is the pox virus.

In one embodiment, the subject is a species selected from the group consisting of cattle, sheep, pigs and fish.

In another embodiment, the subject is an avian species.

In a further embodiment, the avian species is selected from the group consisting of chickens, turkeys, geese, ducks, bantams, quail and pigeons.

In a further embodiment, the administration comprises intravenous, intramuscular or intraperitoneal injection.

The subject invention also provides a method of immunizing a subject against infection by *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising the step of feeding to the subject a plant whose cells express a 56 kDa or 82 kDa polypeptide from the gametocytes of *Eimeria maxima*.

In one embodiment, the plant is wheat.

In another embodiment, the plant is corn.

In one embodiment, the subject is a species selected from the group consisting of cattle, sheep, pigs and fish.

In another embodiment, the subject is an avian species.

In a further embodiment, the avian species is selected from the group consisting of chickens, turkeys, geese, ducks, bantams, quail and pigeons.

The subject invention also provides a method of immunizing a subject against infection by *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising the step of administering to the subject a plasmid comprising an isolated nucleic acid comprising a nucleotide sequence encoding a 56 kDa or 82 kDa polypeptide from the gametocytes of *Eimeria maxima*, or encoding a homolog of the polypeptide, or a complement of the nucleic acid.

In one embodiment, the subject is a species selected from the group consisting of cattle, sheep, pigs and fish.

In another embodiment, the subject is an avian species.

In a further embodiment, the avian species is selected from the group consisting of chickens, turkeys, geese, ducks, bantams, quail and pigeons.

In a further embodiment, the administration comprises intravenous, intramuscular or intraperitoneal injection.

A homolog of the nucleic acid of the invention is a nucleic acid that codes for a polypeptide which has substantially the same biological activity as the polypeptide encoded by the nucleic acid. The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

It is an object of the present invention to provide nucleotide sequences encoding the 56 and 82 kDa antigens from Gametocytes of *Eimeria maxima* and the deduced amino acid sequence therefor. Specifically exemplified coding sequences are given in FIGS. 4 and 5, together with the deduced amino acid sequence. All synonymous coding sequences for the exemplified amino acid sequences are within the scope of the present invention.

It is a further object of the present invention to provide functionally equivalent coding and protein sequences, including equivalent sequences from other *Eimeria* species. Functionally equivalent 56 and 82 kDA antigens from Gametocytes of *Eimeria maxima* coding sequences are desirably from about 50% to about 80% nucleotide sequence homology (identity) to the specifically identified coding sequence, from about 80% to about 95%, and desirably from about 95% to about 100% identical in coding sequence to the specifically exemplified coding sequence.

Hybridization conditions of particular stringency provide for the identification of homologs of the coding sequence from other species and the identification of variant sequences, where those homologs and/or variant sequences have at least (inclusively) 50 to 85%, 85 to 100% nucleotide sequence identity, 90 to 100%, or 95 to 100% nucleotide sequence identity. Each integer and each subset of each specified range is intended within the context of the present invention.

The coding sequence and methods of the present invention include the homologous coding sequences in species other than *Eimeria maxima*. Methods can be employed to isolate the corresponding coding sequences (for example, from cDNA) from other organisms, including but not limited to other species such as *Eimeria tenella, Eimeria acervulina, Eimeria necatrix, Eimeria praecox, Eimeria mitis* and *Eimeria brunetti* useful in the methods of this invention using the sequences disclosed herein and experimental techniques well known to the art.

Specifically included in this invention are sequences from other species than those exemplified herein, which sequences hybridize to the sequences disclosed under stringent conditions. Stringent conditions refer to conditions understood in the art for a given probe length and nucleotide composition and capable of hybridizing under stringent conditions means annealing to a subject nucleotide sequence, or its complementary strand, under standard conditions (i.e., high temperature and/or low salt content) which tend to disfavor annealing of unrelated sequences.

"Conditions of high stringency" means hybridization and wash conditions of 65°-68° C., 0.1×SSC and 0.1% SDS (indicating about 95-100% nucleotide sequence identity/similarity). Hybridization assays and conditions are further described in Sambrook et al. (1989) Molecular Cloning, Second Edition, Cold Spring Harbor Laboratory, Plainview, N.Y. As used herein, conditions of moderate (medium) stringency are those with hybridization and wash conditions if 50-65° C., 1×SSC and 0.1% SDS (where a positive hybridization result reflects about 80-95% nucleotide sequence identity). Conditions of low stringency are typically those with hybridization and wash conditions of 40-50° C., 6×SSC and 0.1% SDS (reflecting about 50-80% nucleotide sequence identity).

A homolog of the polypeptide of the invention is a polypeptide which has substantially the same amino acid sequence and biological activity as the polypeptide. Thus, a homolog may differ from the polypeptide of the invention by the addition, deletion, or substitution of one or more non-essential amino acid residues, provided that the resulting polypeptide retains the biological activity of the polypeptide. Persons skilled in the art can readily determine which amino acids residues may be added, deleted, or substituted (including with which amino acids such substitutions may be made) using established and well known procedures, including, for example, conventional methods for the design and manufacture of DNA sequences coding for bacterial expression of polypeptide homologs of the subject polypeptide, the modification of cDNA and genomic sequences by site-directed mutagenesis techniques, the construction of recombinant polypeptides and expression vectors, the bacterial expression of the polypeptides, and the measurement of the biochemical activity of the polypeptides by means of conventional biochemical assays.

Examples of homologs are deletion homologs containing less than all the residues specified in the subject polypeptide, substitution homologs wherein one or more residues specified are replaced by other residues, and addition homologs wherein one or more amino acids residues are added to the polypeptide. All such homologs share the biological activity of the polypeptide of the invention.

"Substantially the same polypeptide" is herein defined as encompassing the deletion, addition or substitution of fewer than four amino acids at the N-terminus of the amino acid sequence of the polypeptide. Furthermore, there may be deletions, additions or substitutions in the sequence which do not eliminate the biological activity of the polypeptide. Such modifications are known to those skilled in the art. For example, substitutions may encompass up to 10 residues in accordance with the homologous or equivalent groups described by e.g. Lehninger, Biochemistry, 2nd ed. Worth Pub., New York. (1975); Creighton, Protein Structure, a Practical Approach, IRL Press at Oxford Univ. Press, Oxford, England (1989); and Dayhoff, Atlas of Protein Sequence and Structure 1972, National Biomedical Research Foundation, Maryland (1972).

The term "biologically active", as used herein, refers to a polypeptide having structural, regulatory, or biochemical functions of a naturally occurring molecule. Likewise, "immunologically active" refers to the capability of the natural, recombinant, or synthetic polypeptide, or any oligopeptide portion thereof, to induce a specific immune response in an animal or cells and to bind with specific antibodies.

"Substantially the same biological activity" refers to biological activity the same as that of the naturally occurring molecule possibly differing slightly in degree or level which would still be known by the skilled artisan to be the same biological activity.

The term "portion", as used herein, in connection with a polypeptide (as in "a portion of a given polypeptide") refers to fragments of that polypeptide. The fragments may range in size from four (4) amino acid residues to the entire amino acid sequence minus one amino acid. The term "portion", as used herein, in connection with a nucleic acid (as in "a portion of a given nucleic acid") refers to fragments of that nucleic acid. The fragments may range in size from twelve (12) nucleotide residues to the entire nucleic acid sequence minus one nucleotide.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The present invention provides the recombinant cloning and sequencing of two of the major *Eimeria maxima* gametocyte antigens having molecular weights of 56 and 82 kDa.

The present invention also provides the expression of these recombinant antigens in an *E. coli* expression system using the plasmid pTrcHis.

The subject invention also provides a vaccine against coccidiosis comprising the recombinant 56 kDa antigen. In addition, the present invention provides a vaccine against coccidiosis comprising the recombinant 82 kDa antigen.

The present invention provides the cloning and sequencing of two of the major *Eimeria maxima* gametocyte antigens having molecular weights of 56 and 82 kDa.

The production of gametocytes was scaled-up in order to isolate enough gametocyte antigen to carry out amino acid sequencing (i.e. milligram quantities of the specific antigens) on the 56 and 82 kDa glycoproteins themselves. This scale up production was in itself a very difficult task, and required infecting several thousand chickens in order to provide enough material for carrying out sequence analyses. After achieving this goal, it was possible to produce enough affinity purified gametocyte antigen (APGA) to start isolating the two glycoproteins on a large scale.

The purified gametocyte antigenic glycoproteins were separated by two-dimensional, SDS polyacrylamide gel electrophoresis. After analysis of the two-dimensional gels by staining, the position of the 56 and 82 kDa antigens was determined by transfer to a PVDF membrane filter and immunodetection using antisera to APGA. After identification and removal of the 56 and 82 kDa antigens from the filter, amino acid sequencing of both their N-termini as well as internal protein sequences obtained from tryptic peptides was performed. These peptide sequences were used to predict the DNA sequences, based on which small, specific oligonucleotide probes were synthesized.

The specific oligonucleotide probes were used in RACE PCR (rapid amplification of cDNA ends) to prepare cDNA molecules from the gametocyte RNA that encodes the 56 and 82 kDa antigens. This method allowed for the production of full length cDNA molecules that are specifically amplified from mRNA molecules that contain within them the RNA sequences that encode the desired peptides. This cDNA product was then fully sequenced and the presence of the various peptides sequenced above was confirmed. Surprisingly, we found that the cDNA clones we obtained were not related to those described in Wallach et al., U.S. Pat. No. 5,932,225. Therefore, it appears that in Wallach et al., artifacts occurred when screening the cDNA library with antibodies and the clones thought to encode the 56 and 82 kDa antigens which were isolated did not in fact encode these antigens.

Finally the two new cDNA clones were used as a probe in Southern and northern blotting experiments to identify the specific gene(s) and mRNA molecule(s) that encode for the 56 and 82 kDa antigens. Whereas previously no clear banding patterns could be obtained on blots (U.S. Pat. No. 5,932,225), the number and size of gene fragments and mRNA transcripts that encode for the two antigens were clearly discerned.

The present invention further provides a method for cloning the 56 and 82 kDa antigens into a bacterial expression vector, pTrcHis, containing a poly his tag (to aid in the purification of the recombinant antigens). The two genes are then expressed in *E. coli* by adding a specific inducer molecule (isopropyl-α-D-thiogalactopyranoside), followed by the identification of the recombinant 56 and 82 kDa antigenic proteins by western blotting. The results of these blots showed that the 56 and 82 kDa recombinant antigens had the correct size based on measurements by mass spectrometry, and were recognized by antibodies to the his tag as well as protective antisera raised against the native 56 and 82 kDa gametocyte antigens. These results confirmed the identity of the clones and showed that these recombinant antigens can be used to replace the native antigens in the maternally based vaccine against coccidiosis in chickens.

The present invention further describes the relationship between the 56 kDa gametocyte antigen with a 30 kDa oocyst protein. This oocyst protein was shown, by immunoblotting, to strongly react with antiserum against the 56 and 82 kDa gametocyte antigens. By sequencing the amino terminus of the kDa oocyst protein, we found that there was a precise match with the amino terminus of the 56 kDa antigen. It was therefore concluded that the 56 kDa antigen is processed during the development of oocysts from gametocytes into the kDa protein.

The invention is further illustrated by the following examples which in no way should be construed as being further limiting. One skilled in the art will readily appreciate that the specific methods and results discussed are merely illustrative of the invention as described more fully in the claims which follow thereafter.

EXPERIMENTAL DETAILS

Example 1

Purification of *Eimeria maxima* Gametocytes on a Large Scale

In order to produce very large quantities of gametocytes, 4,000 heavy breed chickens were infected with 10,000 sporulated *E. maxima* oocysts, and were then sacrificed on day six (about 134 hours) post infection. The chicken intestines were removed, washed with PBS and cut open longitudinally. They were then cut into 1 cm long pieces and placed in a SAC buffered solution (170 mM NaCl, 10 mM Tris pH 7, 10 mM glucose, 5 mM $CaCl_2$, 1% powdered milk) containing 0.5 mg/ml hyaluronidase (Type III from Sigma, 700 units/mg). The intestinal pieces were incubated at 37° C. for 20 minutes after which they were placed on top of a gauze filter. The pieces were rinsed with large quantities of SAC buffer and the resulting filtrate was collected. This was then filtered through a 17 micron polymon filter (Swiss Silk Bolting Cloth Mfg. Co. Ltd., Zurich, Switzerland) and the resulting filtrate was then filtered through a 10 micron filter. The gametocytes were collected from the top of the 10 micron filter, examined and counted microscopically, and placed in centrifuge bottles, which were spun at 800×g for 10 minutes. The gametocytes were then washed twice with SAC buffer, and frozen at −70° C.

Example 2

Purification of the 56, 82 and 230 kDa Gametocyte Antigens

The frozen gametocytes were thawed at room temperature and the proteins were extracted as described previously (Wallach 1995). The 56 and 82 kDa gametocyte antigens were isolated from the protein extract by running it over a Sepharose 4B column containing the monoclonal antibody 1E11-11 raised against the 56 kDa antigen. A complex of the gametocyte antigens were allowed to bind to the monoclonal antibody attached to the resin, the non-specific material was washed off using buffer, and the affinity purified gametocyte antigens (APGA) were eluted from the column. The purified APGA was lyophilized. A small sample of APGA was analyzed by SDS-PAGE where the 56 and 82 kDa native antigens were clearly visualized (FIG. 1).

Example 3

Figure 3:
FIG. 3 depicts a Coomassie stained PVDF filter from a two-dimensional SDS PAGE gel and the identification of the spots that were cut out for sequence analysis. Arrows point to the 56 and 82 kDa native antigens.

Two Dimensional Gel Electrophoresis of APGA and Isolation of the Major 56 and 82 kDa Antigens The 56 and 82 kDa gametocyte antigens were isolated from APGA. Lyophilized APGA was prepared as described in Example 2, and was solubilized in water. The proteins were then separated by two-dimensional SDS-PAGE (FIG. 2), and identified by immunoblotting using a polyclonal chicken anti-APGA antibody, which recognizes both the 56 and 82 kDa proteins. Once identified and their location established on two-dimensional SDS-PAGE gels, the proteins were then transferred to a PVDF membrane filter, and stained with Coomassie Blue (FIG. 3). Immunoblotting was carried out at the same time, and the two blots were compared to clearly identify the 56 and 82 kDa proteins. The spots corresponding to the 56 and 82 kDa gametocyte antigens were cut out of the membranes and the amino-terminus of each antigen was sequenced.

Example 4

Amino Acid Sequencing of the Amino-Terminus as Well as Internal Tryptic Peptides from the 56 and 82 kDa Antigens The amino-termini of the 56 and 82 kDa proteins were sequenced:
amino-terminus of the 56 kDa protein: VPSTTPVEN-QVHPY-EM (SEQ. ID. NO. 7)
amino-terminus of the 82 kDa protein: -PTVLDTTTG-QVEDT (SEQ. ID. NO. 8)

In order to determine the protein sequence of internal tryptic fragments of the 56 and 82 kDa proteins, the APGA preparation was first separated by one dimensional SDS-PAGE and stained with Coomassie Blue. The proteins were then excised from gels and digested with trypsin and sequenced.

Several tryptic peptide sequences were obtained from both proteins and the results are summarized in Table 1.

protocols described in the SMART RACE PCR manual, and the DNA polymerase, Advantage Taq (Clonetech), a high fidelity enzyme mixture.

The gametocytes had been isolated from chicken intestines, filtered a number of times and washed thoroughly as described in Example 1. There was a concern that residual chicken intestinal material was still present in this preparation. Consequently, PCRs carried out using degenerate primers designed to the amino-terminus of the 56 and 82 kDa genes and degenerate primers designed to internal tryptic peptide fragments gave rise to bands in both cDNA samples prepared from purified gametocytes and uninfected chicken cells. In this situation PCR bands, which stained intensely with ethidium bromide on agarose gels, were purified, cloned into pGEMT-Easy (Promega) and sequenced (SUPAMAC sequencing service, Sydney, Australia). In some cases, when rearrangements were observed or the cloned fragment was difficult to sequence, sequence was obtained directly from the PCR product. If the DNA sequence data from the PCR product translated to any of the amino acid sequences of the tryptic peptides, the PCR product was of parasitic origin and sequencing continued.

The full length sequence of the 56 and 82 kDa proteins are shown in FIGS. 4 and 5, respectively. The full length sequence of the 230 kDa protein is presented in FIG. 12.

Amino acid sequence of the tryptic peptides and N-terminus of the 56 gametocyte antigen matched the deduced amino acid sequence arising from the corresponding cloned DNA.

TABLE 1

Amino acid sequences of tryptic peptides isolated from the 56 and 82 kDa antigens.

| Peptide | 56 kDa Antigen | 82 kDa antigen | SEQ. ID. NO. |
|---|---|---|---|
| A | VQDV(L/I)VDA(L/I)WAS(L/I)R | ATGFSEEEVMR | 9, 10 |
| B | VTEMMDM(L/I)SNR | TGGLFDQACNDAPPSR | 11, 12 |
| C | Q(L/I)Q(L/I)QDQMMR | TGP(L/I)STTGATGATTGPVAA(L/I)R | 13, 14 |
| D | AAEEF(L/I)HR | P(L/I)THVE | 15, 16 |
| E | | R(L/I)AAVPGTTAGT | 17 |
| F | D(L/I)QEY(L/I)STAFNWA-ENQSTAYTR | (L/I)AEGAEPRPVMPAAATAAANLR | 18, 19 |
| G | RQTAAWMDRTA(L/I)EQEETT | | 20 |
| H | MNAAMDSSNE(L/I)MTT | | 21 |
| I | KFPET(L/I)F | | 22 |

The amino acid sequences obtained did not show any homology to any other known protein.

Example 5

RACE PCR Cloning and Sequencing of the Genes Encoding the 56 and 82 kDa Antigens The genes for the 56 and 82 kDa proteins were amplified from gametocyte cDNA using SMART RACE PCR technology (Clonetech). RNA was isolated from E. maxima gametocytes and mRNA was purified using Dynal beads (Dynal). SMART ready cDNA was synthesized following the protocols according to the manufacturer's instructions using the reverse transcriptase Powerscript (Clonetech). Amplifications of both the 5' and 3' ends were carried out using the Nine tryptic peptides were sequenced for the 56 kDa protein (Table 1). All peptides but one, sb56i, could be mapped to the cloned gene corresponding to the 56 kDa protein (FIG. 4). This tryptic fragment may correspond to a contaminating band present in the sample. In detail:

Tryptic peptides sb56a, sb56b, sb56c, sb56d, sb56f and sb56h matched precisely to the deduced amino acid sequence predicted by the cloned DNA.

Tryptic peptide sb56g did not match precisely to the deduced amino acid sequence predicted by the cloned DNA. The sequence of the tryptic fragment was reanalysed, and the new sequence matched more closely with the predicted sequence derived from the cloned DNA.

Tryptic fragment sb56g Original Sequence:

```
RQ--TAAWMDR--TA[L/I]EQEETT    (SEQ. ID. NO. 23)
```

Reanalysed sb56g Sequence:

```
RGVQTAAWMDGVTA I EKEETT       (SEQ. ID. NO. 24)
```

Deduced aa Sequence from DNA:

```
RGVQTAAWMNGVTA I EKEETT       (SEQ. ID. NO. 25)
```

A discrepancy still remains in this peptide at amino acid 10, where the protein sequence reveals a D and the DNA sequence predicts a N. This segment of DNA was sequenced 4 times, and each time predicted an N.

Amino acid sequence of the tryptic peptides and N-terminus of the 82 gametocyte antigen match the deduced amino acid sequence arising from the corresponding cloned DNA.

Seven tryptic peptides were sequenced for the 82 kDa protein (Table 1). All peptides but two, sb82d and sb82e could be mapped to the cloned gene corresponding to the 82 kDa protein. This tryptic fragment may correspond to a contaminating band present in the sample. In detail:

Tryptic peptides sb82a, sb82b, sb82c, sb56d and sb82f matched precisely to the deduced amino acid sequence predicted by the cloned DNA.

Tryptic peptides sb82d and sb82e did not match to the deduced amino acid sequence predicted by the cloned DNA.

In addition to the sequence information described above:
1) The predicted size of the ORF encoding the mature form of the 82 kDa protein is 64,275 Da, which corresponded to the true size of the native protein of 62,236 Da, as determined by mass spectrometry.
2) The predicted size of the ORF encoding the mature form of the 56 kDa protein is 51,407 Da which corresponded to the true size of the native protein of 52,450 Da, as determined by mass spectrometry.

Finally, the two protein and DNA sequences did not show any homology to any other known gene or protein.

Example 6

Southern and Northern Blotting Using the 56 and 82 kDa cDNA Cloned Probes

Figure 6:
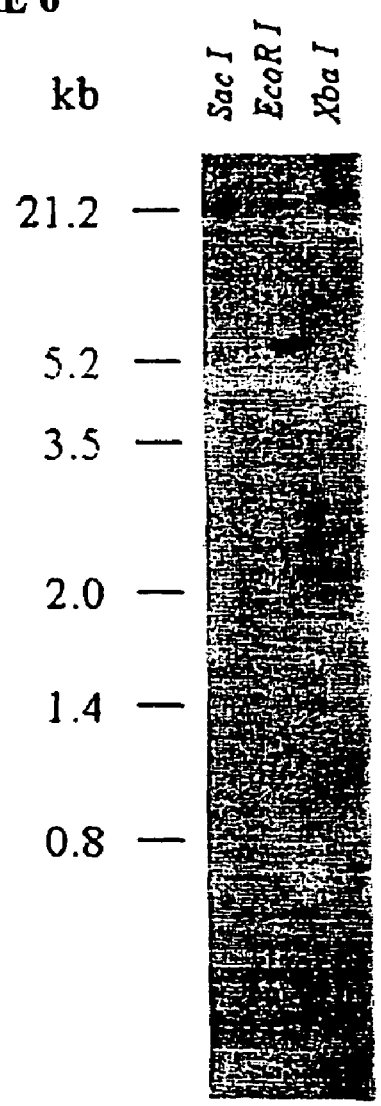
FIG. 6 depicts a Southern blot of gametocyte and control chicken DNA probed with the cDNA clone for the 56 kDa antigen. The restriction enzymes used for digestion of the DNA and the marker band sizes in kilobases are indicated.
Figure 7:
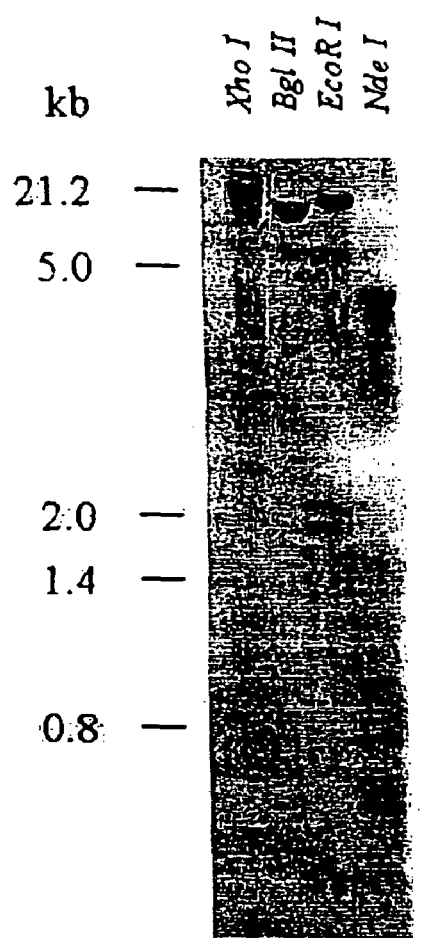
FIG. 7 depicts a Southern blot of gametocyte and control chicken DNA probed with the cDNA clone for the 82 kDa antigen. The restriction enzymes used for digestion of the DNA and the marker band sizes are indicated.

Southern blotting using *E. maxima* and chicken DNA was carried out by first cutting the DNA with a variety of restriction enzymes and separating the resulting DNA fragments on an agarose gel. This is followed by transferring the DNA to nitrocellulose paper, probing with a $P^{32}$ labeled cDNA probe for the 56 (FIG. 6) or 82 (FIG. 7) kDa antigens and performing autoradiography. The results showed that for both the 56 and 82 kDa antigens there appear to be two different, single copy genes, which encodes the two proteins.

Figure 8:
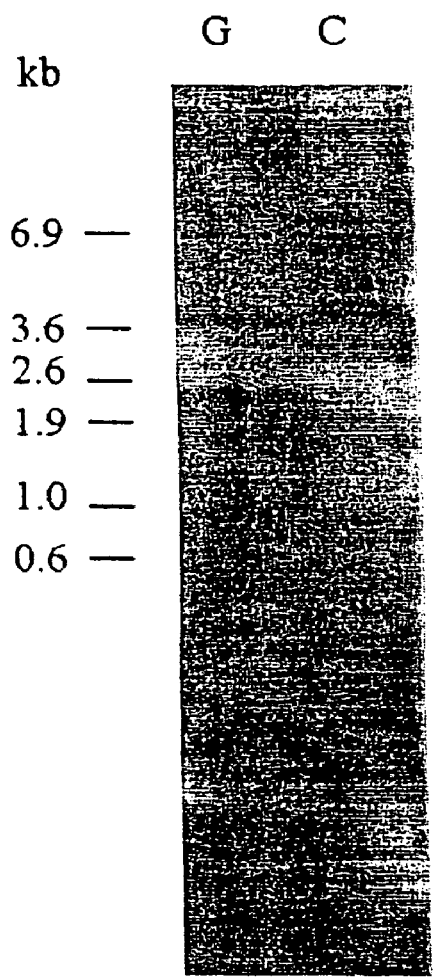
FIG. 8 depicts a northern blot of gametocyte (G) and control (C) chicken total RNA probed with the 82 kDa cDNA clone. The sizes of the marker bands in kilobases are indicated on the left.

Northern blotting using *E. maxima* and chicken RNA was carried out by separating the RNA molecules on an agarose gel, transferring it to a nitrocellulose filter and probing with the $P^{32}$ labelled 56 and 82 cDNA clones. The results showed that the 56 kDa mRNA has a molecular weight of about 1.9 KB and the 82 kDa mRNA had a molecular weight of about 2.4 KB (FIG. 8). These sizes are very similar to those predicted from the DNA sequences.

Example 7

Expression of the Recombinant 56 and 82 kDa Antigens Using the pTrcHis Vector in *E. coli* and Their Analysis Using Sera Against Native APGA The full length gene encoding the 82 kDa protein was amplified from *E. maxima* gametocyte cDNA using gene specific primers carrying terminal restriction sites to facilitate directional cloning into the expression vector pTRCHisb (Invitrogen). The full length gene included the coding region of the amino-terminus of the mature protein and sequence up to, but not including, the stop codon (575 aa). A partial fragment of the gene encoding the 56 kDa protein was amplified from *E. maxima* gametocyte cDNA using gene specific primers carrying terminal restriction sites. This included the amino-terminus of the protein and a further 323 amino acids of sequence, 133 amino acids shorter than the full length mature protein. Both genes were cloned into the commercially available vector pTrcHisb (Invitrogen).

1) Expression of the 56 kDa Gene in pTrcHis B

Transformed bacteria were induced with 1 mM IPTG, and bacterial lysates were analyzed by 1D-SDS PAGE and immunoblotting (FIG. 9). A commercially available anti-His antibody to the His fusion tag of the recombinant protein recognized a band of the predicted size of 40 kDa (this clone lacks the coding region for 133 amino acids) under inducing conditions. Under non-induced conditions there was also a low level of reactivity with this band indicating that there is some degree of leakiness of the gene expression. Recognition of the recombinant 56 kDa protein was then assessed by immunoblotting with the chicken polyclonal anti-APGA antibody. The immunoblot showed that the anti-APGA antibody recognized the native form of the protein by one dimensional SDS-PAGE, as well as the recombinant protein, clearly demonstrating that the cloned gene product indeed codes for the 56 kDa protein.

2) Expression of the 82 kDa Gene in pTrcHis B

Figure 10:
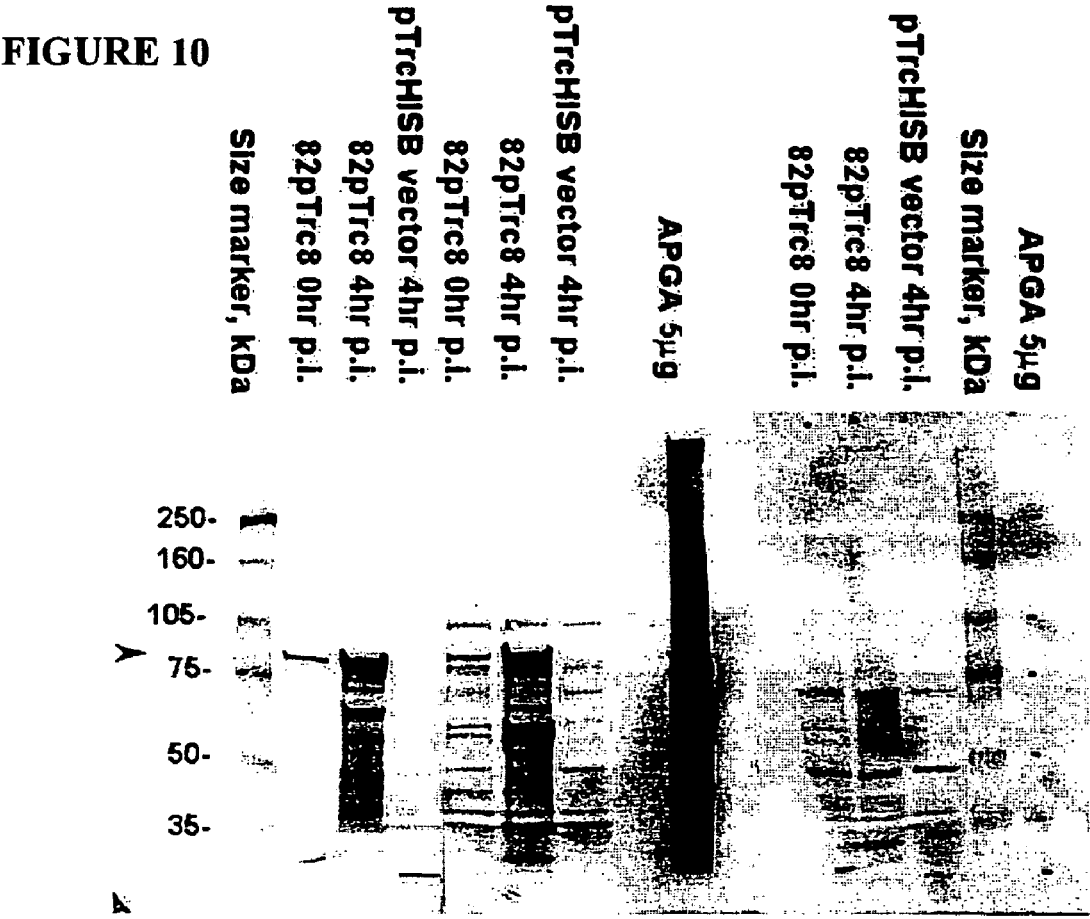
FIG. 10 depicts a Coomassie stained gel and immunoblot of proteins from bacteria containing pTrcHisB-82 kDa cDNA cloned plasmids. The immunoblot shows reactivity of the anti polyhistidine, chicken anti-APGA as well as uninfected chicken (negative control) sera with the 82 kDa recombinant protein under IPTG induced and non-induced conditions at various times after induction. As a negative control, the experiment was also performed using bacteria transformed with the same plasmid without an insert. As a positive control, native APGA is also run. The arrow shows the position of the 82 kDa recombinant protein. The sizes of the protein marker bands are indicated on the left.

Transformed bacteria were induced with 1 mM IPTG, and bacterial lysates were analysed by one dimensional SDS PAGE and immunoblotting (FIG. 10). A commercially available anti-H is antibody to the His fusion tag of the recombinant protein recognized a band of the predicted size of 82 kDa under inducing and non-inducing conditions. Recognition of the recombinant 82 kDa protein was then assessed by immunoblotting with the chicken polyclonal anti-APGA antibody. This antibody was produced by immunizing chickens with native APGA isolated from purified gametocytes. The immunoblot showed that the anti-APGA antibody recognized the native form of the protein by 1D SDS-PAGE, as well as the recombinant protein, clearly demonstrating that the cloned gene product indeed codes for the 82 kDa protein.

Based on the above results together with the sequence analyses described in Example 5, we concluded that the two cDNA clones described above are the authentic genes encoding for the 56 and 82 kDa antigens. In addition, the strong reactivity with the antisera raised against the native antigens shows that these recombinant proteins can now be used to replace APGA for the immunization of chickens against coccidiosis.

Example 8

Homology of the 56 kDa Antigen with a 30 kDa Antigen from *E. maxima* Oocysts

Figure 11:
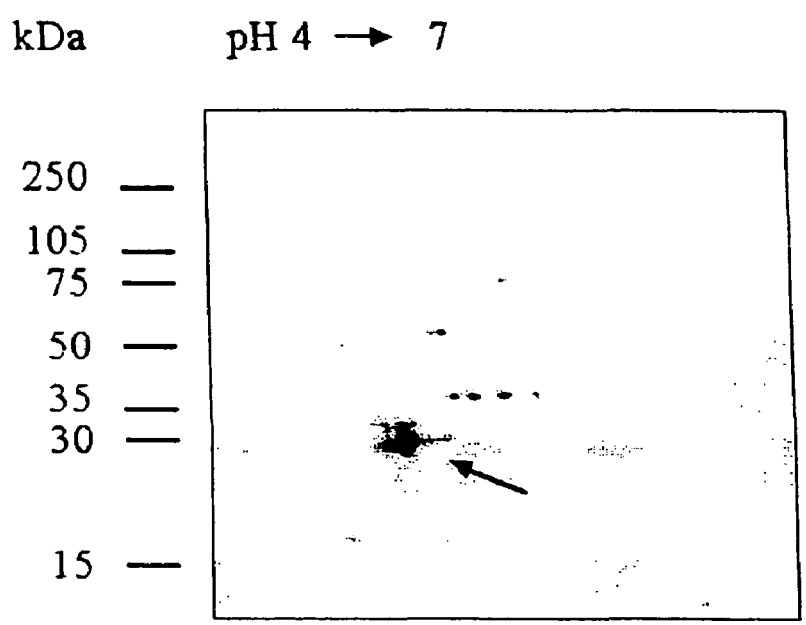
FIG. 11 depicts an immunoblot of a whole lysate of unsporulated *E. maxima* oocysts separated by 2 dimensional SDS PAGE. The gel was blotted onto a membrane filter and probed with an antiserum raised against APGA. The strongly reacting 30 kDa spot is shown with an arrow. This was the spot that was cut out of the gel and used for sequence analysis.

Antibodies to APGA were used to detect homologous proteins on a two-dimensional blot of oocyst antigens. We found that there was very strong reactivity with a protein of 30 kDa (FIG. 11). This spot was cut out of the membrane filter and the N-terminus of the protein was sequenced. The resulting amino acid sequence corresponded precisely to the N-terminal sequence of the gametocyte 56 kDa antigen. Based on this finding we concluded that the gametocyte 56 kDa antigen is processed into the 30 kDa protein of the oocyst stage of development.

Example 9

Expression of gam 56, a 56 kDa Gametocyte Antigen from *Eimeria maxima*
Native protein: Mr 56,000 (size determined by molecular sizing (MS): 52,450 Da)
Source: Parasitic: *Eimeria maxima*
Life cycle stage: macrogametocyte
Gene: 1,754 base pairs sequenced presented over 5 polymerase chain reaction (PCR) fragments, all of which are cloned into pGEMT-Easy, except for the last ~600 bp of the gene, which includes ~400 bp of the coding region.
5'UTR (1-102 bp)
ORF (103-1,533 bp)
3'UTR (1,534-1,731 bp)
polyA tail (1,732-1,754 bp)
pI: 4.8 predicted from sequence (by 2D SDS-PAGE, the protein migrates towards the acidic end of the gel)
Expression Constructs
Expression vectors used: pTRCHisb, pET25b
Expression construct: given p56TRCHisb1
Gene fragment that was cloned into the expression vector: gam 56 was amplified from cDNA using the following primer pairs: SB74/SB75 (172-1137 bp) for directional cloning into the BamHI/EcorI site of TRCHisb. The amplified region contains the sequence encoding the amino terminus of the mature protein, excluding the initiator methionine and leader sequence. It contains a tyrosine-serine rich region and excludes a proline-methionine rich region.
Amino acid composition of cloned gam 56 fragment: 2 cysteines present amino acid composition of gene fragment cloned into pTRCHisb:

| S(12.7%) | Y(11.5%) | A(8.7%) | T(8.4%) | P(7.2%) |
|---|---|---|---|---|
| R(6.6%) | E(6.0%) | M(5.5%) | L(5.5%) | V(4.6%) |
| Q(4.3%) | N(4.3%) | G(3.8%) | D(3.5%) | W(1.7%) |
| F(1.4%) | K(1.4%) | I(1.4%) | H(0.9%) | C(0.6%) |

Predicted protein size: 41 kDa
Yield: 0.9-1.4 μg/ml (nickel agarose purified protein/ml culture) Difficult to see induced protein in crude bacteria lysate on a Commassie Blue stained gel.
Expression Conditions:
The promoter is leaky, therefore we can get expression in the absence of IPTG.
Used baffled flasks, 37° C., 4 h induction, with 1 mM IPTG, 0.1 mg/ml ampicillin in 0.01 M $Mg^{2+}$SOB (SOB better than LB).
Normally, one predominate band at ~42 kDa is obtained after purification and detection with silver staining. Often some higher molecular weight bands, which may be aggregates, are obtained after purification as well as the main ~42 kDa band. The protein seems to aggregate at −20° C. and 4° C.; after purification we desalt and add stabilisers (3% lactose, 1% monosodium glutamate).

Example 10

Immunization and Challenge Trial of the Recombinant 56 kDa (r56) and 82 kDa (r82) Gametocyte Antigens, and the 250 kDa (r250) Asexual Stage Antigen in Chickens
Immunization
Animals
　Chickens:—84 day old (~12 weeks) Australorp cockerels kept on medicated (robenidene) food
　all chickens were individually tagged and recorded
Antigens
　Recombinant proteins in the pTRCHisb expression system were grown at 37° C. in 0.1 mg/ml ampicillin in 0.01 M $Mg^{2+}$ SOB and induced for 4 hours with 1 mM IPTG. Proteins were purified on a Ni-agarose column, concentrated, desalted, and lyophilized with stabilizers (3% lactose, 1% monosodium glutamate). Protein concentrations used for all antigens were measured using the Bradford assay. Affinity Purified Gametocyte Antigen (APGA) preparations provided by M. Wallach was used as a positive control for the trial.
Groups and Doses
　9 chickens used per group; 9 groups in total; 81 chickens used in total.
　Chickens were immunized with 0.5 ml antigen/Freunds Incomplete Antigen (FIA) cocktail (0.25 ml antigen/0.25 ml FIA) per bird, intra-muscularly, on one side only of the chicken, with the following antigens:
Group 1 PBS only
Group 2 Adjuvant (FIA)/PBS
Group 3 APGA (2.5 g)
Group 4 r250 protein (1.0 g)
Group 5 r250 protein (10.0 g)
Group 6 r56 protein (0.5 g)
Group 7 r56 protein (5.0 g)
Group 8 r82 protein (0.5 g)
Group 9 r82 protein (5.0 g)
Immunization Schedule

| Immunization 1: | week 1 |
|---|---|
| Immunization 2: | week 3 |
| Bleed: | week 6 |
| Bleed: | week 8 |
| Bleed/Kill: | week 9 |

Figure 14A:
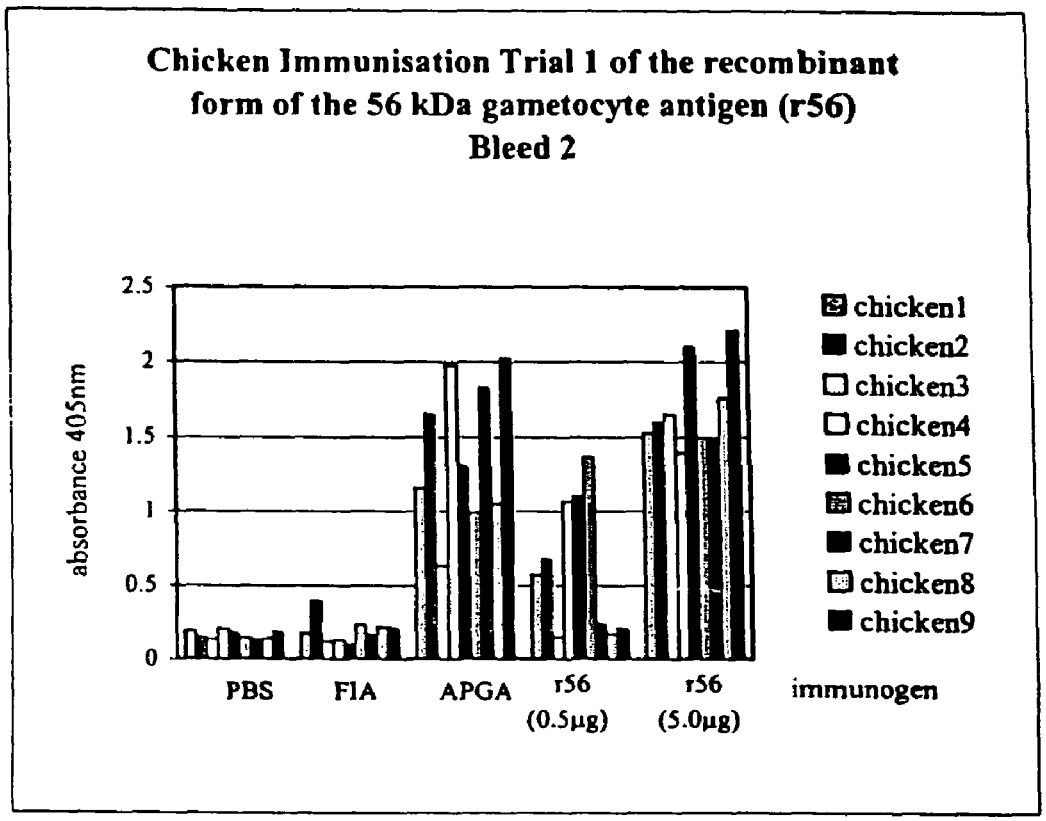
FIGS. 14A & B ELISA results for chicken immunogenicity trial of the recombinant form of the 56 kDa and 82 kDa gametocyte antigen. All serum samples were tested at 1:1000 dilution. A) Coating antigen: APGA to test sera against APGA; r56 purified to test sera taken from chickens immunized with PBS, FIA and the two doses of r56. B) Coating antigen: APGA to test sera against APGA; r82 purified protein to test sera taken from chickens immunized with PBS, FIA and the two doses of r82.
Figure 14B:
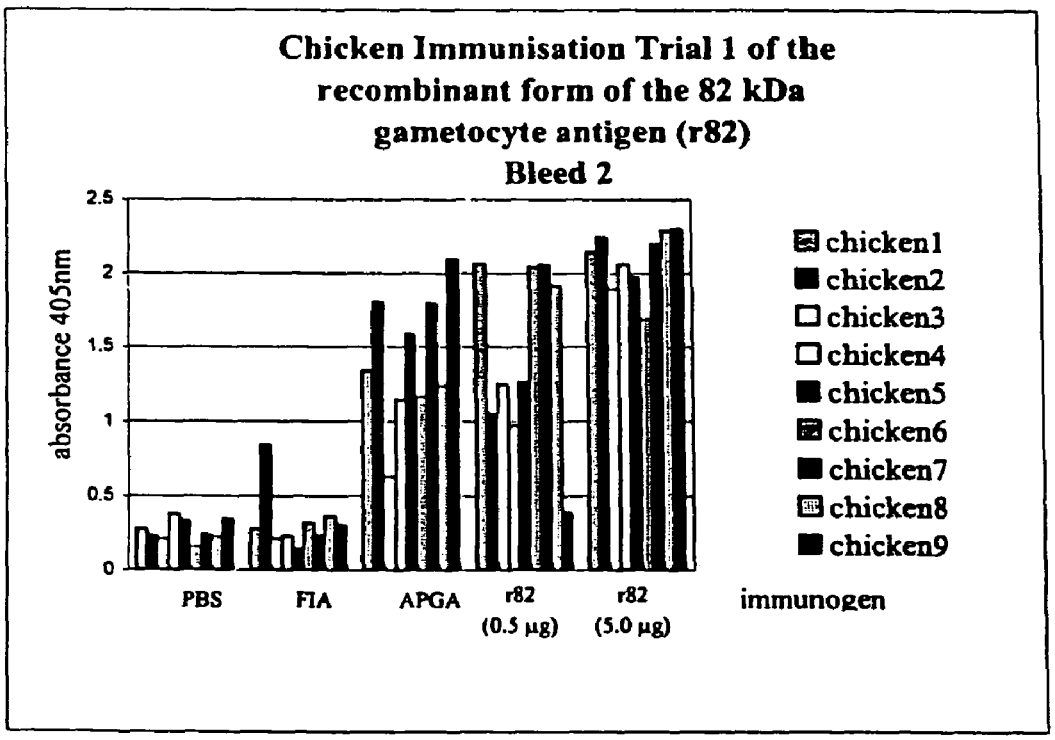

Analyzes
　Bleeds were taken (~1.5-2 ml/bird), sera separated and tested by ELISA and immunoblotting
Results
　Results of the bleeds are shown in FIG. 14.
Challenge
Animals and Parasites
　5 chickens (148 days old; ~4.5 months) from each group which had the highest antibody titre based on the ELISA results of bleed 1 were used; in the case of the PBS and FIA controls, chickens with the lowest antibody titres were used
　*E. maxima* (strain Houghton);
　robenidene was removed from the feed one week prior to challenge
Groups
　The following groups and chickens were taken from the immunization trial described above, and used in the challenge experiments

| Group 1 | PBS only | chicken numbers 2, 3, 4, 6, 8 |
| Group 2 | Adjuvant (FIA)/PBS | chicken numbers 12-16 |
| Group 3 | APGA (2.5 g) | chicken numbers 20, 22, 23, 25, 27 |
| Group 5 | r250 protein (10.0 g) | chicken numbers 37, 39, 41, 44, 45 |
| Group 7 | r56 protein (5.0 g) | chicken numbers 57, 59, 60, 61, 63 |
| Group 9 | r82 protein (5.0 g) | chicken numbers 74, 75, 76, 79, 80 |

Challenge Schedule
  Robenidene removed
  Challenged with 100 sporulated oocysts per bird Day 6
Oocyst Harvest and Count Schedule
Day 0 post-infection
Day 1 post-infection
Day 2 post-infection
Day 3 post-infection
Day 4 post-infection
  Checked oocyst output for contamination of another species Replaced plastic sheet to start collections.

| Day 5 post-infection | Feces collected, and oocysts counted |
| Day 6 post-infection | Feces collected, and oocysts counted |
| Day 7 post-infection | Feces collected, and oocysts counted |
| Day 8 post-infection | Feces collected, and oocysts counted |
| Day 9 post-infection | Feces collected, and oocysts counted |
| Day 10 post-infection | Feces collected, and oocysts counted | and TSP-1-like domains. These domain types are found highly conserved within eukaryotes and therefore the possibility of their inducing auto-immunity must be considered. Furthermore because of the prevalence of such domain types it seems unlikely that they would be responsible for inducing a strong immune response.

PCR primers EP006 (5'-TTGGATCCCGAATTGCAC-CCCA TTCC-3') (SEQ. ID. NO. 43) and EP007 (5'-TTGAATTCTGAATGTCGCCGCTGTCG-3') (SEQ. ID. NO. 44) were designed to amplify the selected DNA region from a cDNA clone encoding the 250 kDa protein. The primers incorporated BamHI (EP006) and EcoRI (EP007) restriction sites to facilitate cloning into the selected expression vector. The PCR product subsequently generated using the primers was gel-purified and its identity confirmed by sequencing.

The bacterial expression vector pTrcHisB (Invitrogen) was selected for expression studies. Plasmid vector DNA and gel purified cDNA insert were digested with the restriction enzymes BamHI and EcoRI, and the digested DNA fragments gel purified and ligated. The ligation mixture was transformed into E. coli strain DH5-a and following plating and incubation, resulting colonies were selected, cultured and used for plasmid preparation. The identity of the selected recombinants was confirmed by DNA sequencing.

In preparation for expression, plasmid DNA containing the expression construct was transformed into the E. coli host expression strain TOP10. Following plating and incubation, a

TABLE 2

Immunization and Challenge Trial I

| | Cumulative oocyst counts (×10$^6$) | | | | | Output (%) | | | | | % inhibition | | | | |
|---|---|---|---|---|---|---|---|---|---|---|---|---|---|---|---|
| Day p.i. | 6 | 7 | 8 | 9 | 10 | 6 | 7 | 8 | 9 | 10 | 6 | 7 | 8 | 9 | 10 |
| 1. PBS only | 6.67 | 17.00 | 26.40 | 27.33 | 27.43 | 100 | 100 | 100 | 100 | 100 | 0 | 0 | 0 | 0 | 0 |
| 2. FIA only | 3.20 | 14.40 | 17.30 | 17.50 | 17.50 | 48 (100) | 85 (100) | 66 (100) | 64 (100) | 64 (100) | 52 (0) | 15 (0) | 34 (0) | 36 (0) | 36 (0) |
| 3. APGA (2.5 µg) | 2.77 | 9.35 | 13.48 | 13.58 | 13.61 | 42 (87) | 55 (65) | 51 (78) | 50 (78) | 50 (78) | 58 (13) | 45 (35) | 49 (22) | 50 (22) | 50 (22) |
| 5. r250 (10 µg) | 0.83 | 8.35 | 13.72 | 14.72 | 14.72 | 12 (26) | 49 (58) | 52 (79) | 54 (84) | 54 (84) | 88 (74) | 51 (42) | 48 (21) | 46 (16) | 46 (16) |
| 7. r56 (5 µg) | 0.33 | 4.53 | 7.20 | 8.16 | 8.53 | 5 (10) | 27 (32) | 27 (42) | 30 (47) | 31 (49) | 95 (90) | 73 (68) | 73 (58) | 70 (53) | 69 (51) |
| 9. r82 (5 µg) | 4.23 | 10.33 | 14.73 | 14.93 | 15.06 | 63 (132) | 61 (72) | 56 (85) | 55 (85) | 55 (86) | 37 (0) | 39 (28) | 44 (15) | 45 (15) | 45 (14) |

Example 11

Expression of a Recombinant Fragment of the 250 kDa a Sexual Stage Protein

The region of the 250 kDa protein encoding the predicted transmembrane domain/cytosolic tail and upstream hydrophilic domain was selected for expression studies (FIG. 15). The area was chosen for a number of reasons and are as follows: 1) similar 3' hydrophilic tail regions have been identified in a number of apicomplexan microneme proteins and appear unique to this family of proteins; 2) such regions have been identified in other microneme proteins also recognised as immunodominant, primarily Eimeria tenella microneme protein 1 (EtMIC1) and surface antigen 5401 (EtMIC4); 3) a similar region was expressed from the E. tenella 5401 antigen (EtMIC4) and was found to afford significant protection against challenge with E. tenella (Danforth et al, 1988); 4) other regions of the protein consist primarily of the EGF-like single bacterial colony was selected and used to establish an O/N culture in LB media. A vector only negative control culture was also established. Aliquots of each culture were then transferred to fresh LB media and incubated until the cells reached mid-log phase, at which stage expression was induced with the addition of 1 mM IPTG. Samples from the expression culture and negative control culture were taken at 0, 1, 2, 5 and 24 hrs post induction, and centrifuged to pellet the bacterial cells. All pellets were subsequently resuspended in TE buffer, sonicated and centrifuged to separate the aqueous soluble fraction (supernatant) from the insoluble fraction (pellet). All fractions were analysed under reducing conditions on SDS-PAGE gels and subsequently stained with Coomassie Blue. When compared to the negative control samples, an over-expressed protein was detected in the soluble fractions, migrating at just below the 45 kDa marker. Western analysis of the soluble fractions using an antibody reactive with the 6× Histidine tag of pTrcHis expression products, detected a protein band of the same apparent molecular weight. The predicted size of the expressed protein is approximately 30 kDa, somewhat less than that observed on SDS-PAGE gels. The size difference might be explained by the high frequency of proline residues in the expressed protein, known to cause proteins to migrate with apparently high molecular weight.

In preparation for immunogenicity trials, the expressed protein was purified using Ni-NTA Agarose nickel-charged resin (QIAGEN), with minor modifications to the manufacturer's recommended protocol. Expressed proteins containing the 6×His tag bind to the resin and are displaced by an increased concentration of imidazole in the elution buffer. Briefly, cell pellets were resuspended in Lysis buffer (50 mM $NaH_2PO_4$, 300 mM NaCl, 10 mM imidazole, pH 8.0), containing 1 mg/ml lysozyme. The suspension was sonicated on ice and centrifuged to pellet insoluble material. The supernatant containing the soluble expressed protein was then mixed with Ni-NTA resin and added to a disposable elution column. The slurry was allowed to settle then washed with Wash buffer (50 mM $NaH_2PO_4$, 300 mM NaCl, 20 mM imidazole, pH 8.0), before elution with Elution buffer (50 mM $NaH_2PO_4$, 300 mM NaCl, 250 mM imidazole, pH 8.0). The purity of eluted fractions was analysed by reducing SDS-PAGE and Coomassie Blue staining.

Figure 16:
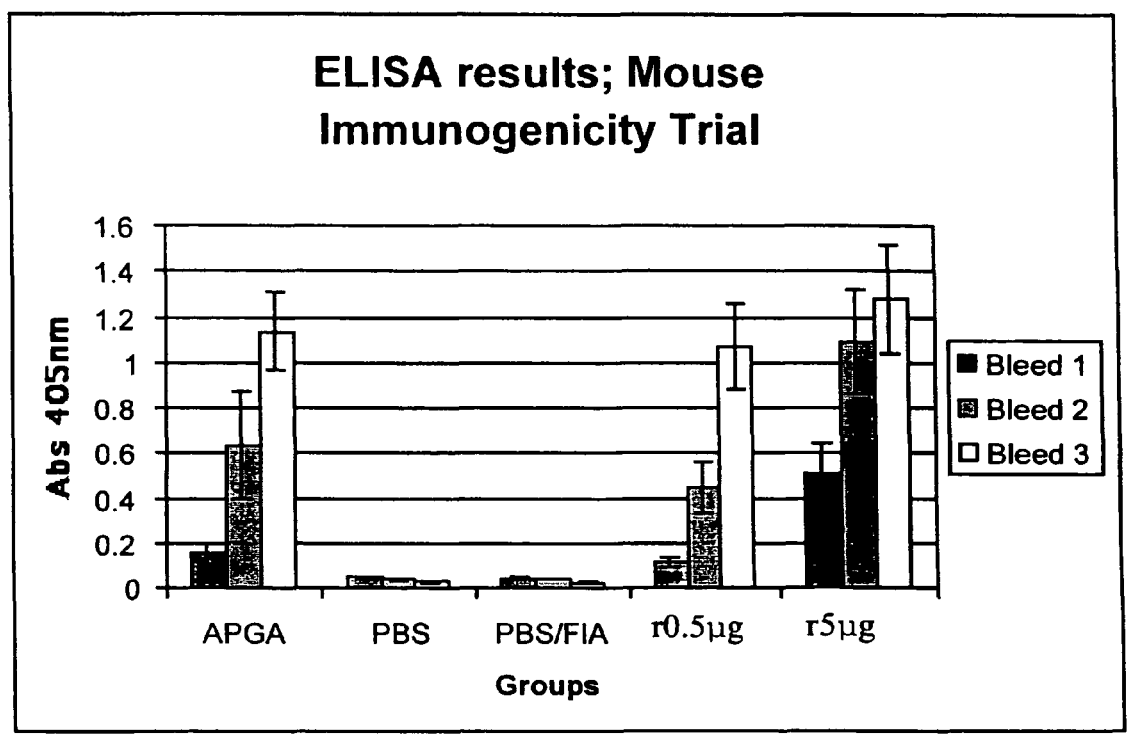
FIG. 16 Mouse immunogenicity trial of the recombinant fragment of the 250 kDa asexual stage protein. The average of each group for the three consecutive bleeds is shown, with standard error bars indicated. All serum samples were tested at 1:1000 dilution. Coating antigen was 100 ng of APGA for sera from the positive control APGA group, or 100 ng of the recombinant protein for the negative control PBS and PBS/FIA groups and the two recombinant protein doses (r0.5 µg and r5 µg).
Figure 17:
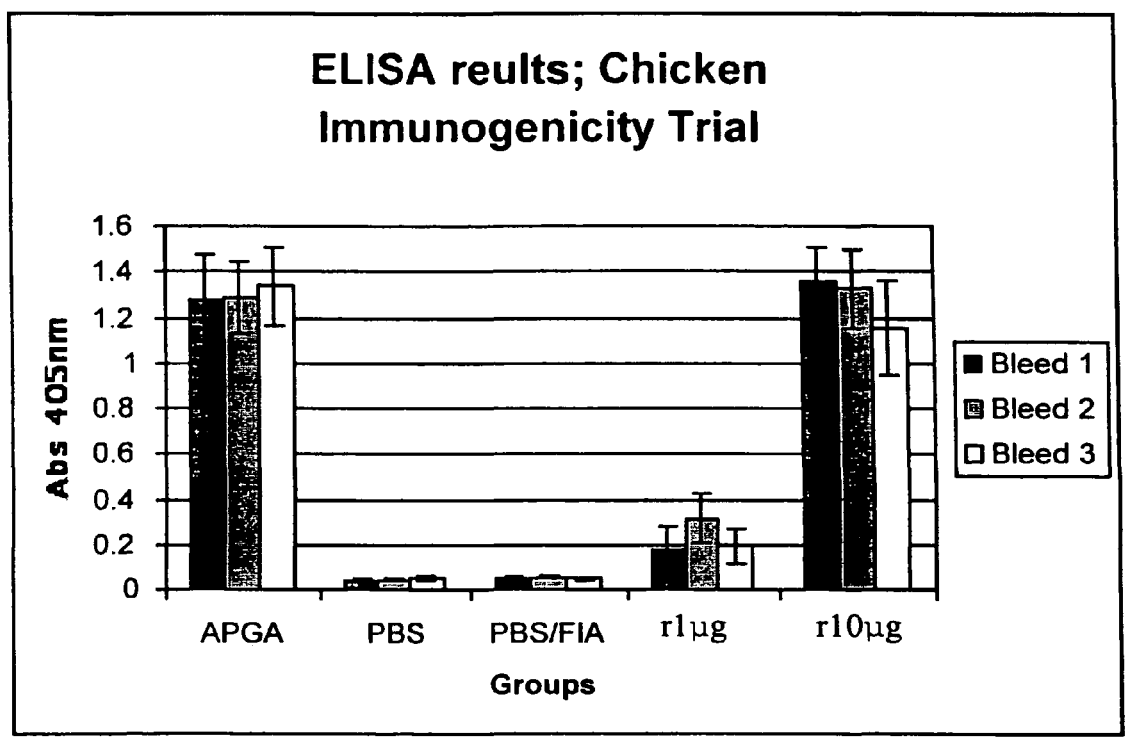
FIG. 17 Chicken immunogenicity trial of the recombinant fragment of the 250 kDa asexual stage protein. The average of each group for the three consecutive bleeds is shown, with standard error bars indicated. All serum samples were tested at 1:1000 dilution. Coating antigen was 100 ng of APGA for sera from the positive control APGA group, or 100 ng of the recombinant protein for the negative control PBS and PBS/FIA groups and the two recombinant protein doses (1 µg and r10 µg).

Details for the immunogenicity trials are as for the 56 kDa and 82 kDa trials. For the mouse trial, 0.5 µg and 5 µg doses of the recombinant protein per mouse were used (6 mice/group). For the chicken trial, 1 µg and 10 µg doses per bird were used (9 chickens/group). ELISA results for the collected serum samples from the mouse and chicken trials are presented in FIGS. 16 and 17 respectively.

Example 12

The oocyst wall of *Eimeria* is derived from precursor proteins found in the sexual stage of the parasite (macrogametocyte) which undergo processing and di-tyrosine crosslinking to form the hardened, protective barrier of the excreted form of the parasite The genes encoding the 56 kDa and 82 kDa sexual stage, macrogametocyte antigens have been cloned and sequenced. Both genes show an unusual amino acid composition, and in particular, both have tyrosine-rich regions; the 56 kDa protein possesses one tyrosine-rich region and the 82 kDa protein possesses two tyrosine-rich regions. Proteins rich in tyrosine have been previously implicated in oocyst wall formation in *E. acervulina* and *E. tenella*. (Eschenbacher et al.) Thus, the role of the tyrosine rich region in the 56 kDa and 82 kDa sexual stage antigens in oocyst wall formation was explored in *Eimeria maxima*.

Figure 18C:
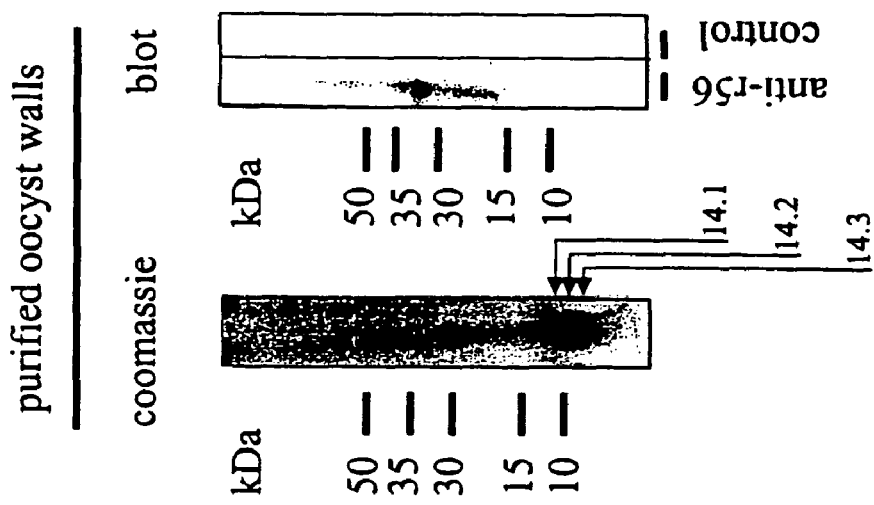
FIG. 18 Anti-r56 recognition of gametocyte and wall antigens in *Eimeria maxima*.
Figure 18B:
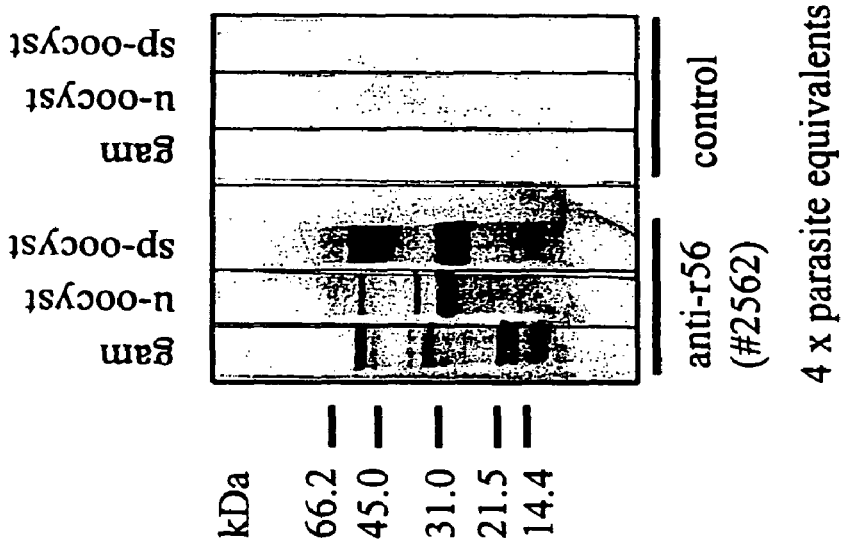
Figure 18A:
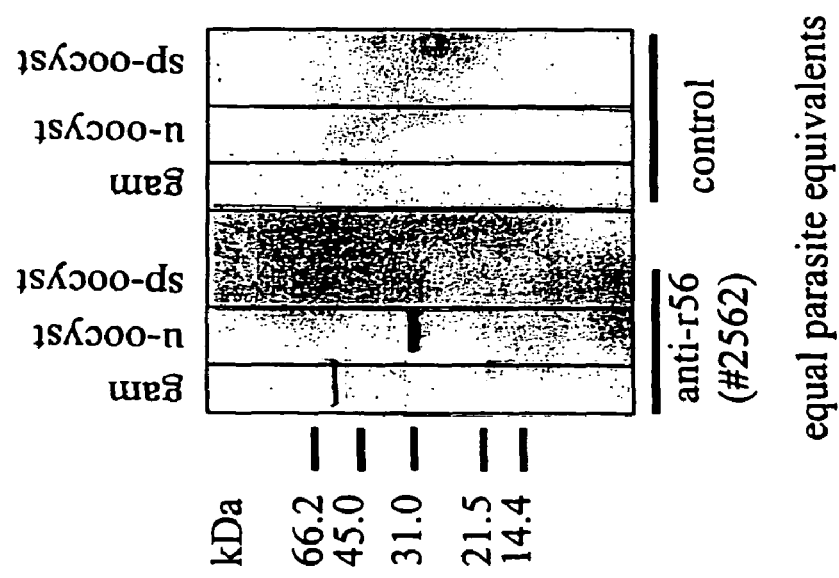

Antibodies to the recombinant form of the 56 kDa protein (anti-r56) and antibodies to the recombinant form of the 82 kDa protein (anti-r82) recognize a ~30 kDa protein in unsporulated and sporulated oocysts, and a ~30 kDa protein in purified wall fragments (see FIGS. 18 and 19). They also recognize their native form counterparts in gametocyte extracts. The ~30 kDa protein recognized in purified oocyst wall fragments by the anti-r82 kDa antibody is not the same as the ~30 kDa protein recognized by the anti-r56; it is slightly smaller. The ~30 kDa protein recognized by the anti-r56 antibody was purified and the N-terminus sequenced. The N-terminus of the ~30 kDa protein corresponds exactly to the N-terminus of the 56 kDa gametocyte antigen (see FIG. 20a).

Others have shown by SDS-PAGE and coomassie blue staining that the oocyst wall of *Eimeria* is composed of two predominant proteins of 14 kDa and 30 kDa. Using better SDS-PAGE separation techniques, we have resolved the 14 kDa protein into 3 components of ~10-14 kDa, and named them 14.1, 14.2 and 14.3, where 14.1 represents the protein which has migrated the slowest on SDS-PAGE gels, and 14.3 the fastest (see FIG. 18c). We have sequenced the N-terminus of all four proteins and the results are presented in FIG. 20. In summary, the 30 kDa protein is a novel protein which does not show any similarity to any other previously characterized protein as determined through a BLAST protein search (see FIG. 20c). The N-terminus of protein 14.3 corresponds to the beginning of the tyrosine rich region in domain 1 of the 82 kDa protein (see FIG. 20b), the N-terminus of protein 14.2 corresponds to the beginning of the tyrosine rich region in domain 2 of the 82 kDa protein (see FIG. 20b), and the N-terminus of protein 14.1 corresponds to the beginning of the tyrosine rich region in the 56 kDa protein (see FIG. 20a).

Together these results show that the oocyst wall of *Eimeria* is derived from precursor proteins found in the wall forming bodies of the sexual stage (macrogametocyte) of the parasite. Through some signaling mechanism, they are proteolytically processed into several shorter proteins of ~30 kDa and ~14 kDa. Contrary to previous findings, our data indicates that the oocyst wall is composed of more than two proteins. Our findings suggest that the oocyst wall is composed of several proteins present at different levels in the parasite, some of which are in high abundance that they are recognized by coomassie blue staining of SDS-PAGE gels, and others that are present at low levels, only detected through the more sensitive technique of immunoblotting. The ~30 kDa protein seen in coomassie blue stained SDS-PAGE gels is not related to the 56 kDa and 82 kDa gametocyte antigens, however, the smaller ~10-14 kDa proteins are. Our most recent finding that di-tyrosine is present at detectable levels in the order of 0.00338 mmol/mol in oocysts, indicates that the small tyrosine rich proteins are probably held in the wall through a mechanism involving di-tyrosine crosslinks. However, we believe that not all the proteins are held in the wall in this way and are currently investigating this.

REFERENCES

Eschenbacher, K. H., Eggli, P., Wallach, M. and Braun, R. (1995) Characterization of a 14 kDa oocytst wall protein of *Eimeria tenella* and *E. Acervulina*, Parasitol., 112:169-176.

Fried, M., Mencher, D., Sar-Shalom, O., and Wallach, M. (1992) Developmental gene expression of a 230-kilodalton macrogamete-specific protein of the avian coccidial parasite, *Eimeria maxima*. Mol. & Biochem. Parasitol., 51:251-262.

Mencher, D., Pugatsch, T. and Wallach, M. (1989) Antigenic proteins of *Eimeria maxima* gametocytes: cell-free translation and detection with recovered chicken serum. Exp. Parasitol. 68:40-48.

Wallach, M., Pillemer, G., Yarus, S., Halabi, A., Pugatsch, T. and Mencher, D. (1990) Passive immunization of chickens against *Eimeria maxima* infection with a monoclonal antibody developed against a gametocyte antigen. Infection & Immunity 58:557-562.

Wallach, M., Smith, N. C., Petracca, M., Miller, C. M. D., Eckert, J. and Braun, R. (1995) *Eimeria maxima* gametocyte antigens: potential use in a subunit maternal vaccine against coccidiosis in chickens. Vaccine, 13:347-354.

Wallach, M. and Vermeulen, A., (1996) Progress Towards a Subunit Vaccine Against Coccidiosis. Misset's World Poultry, Supplement Coccidiosis (2), 22-24.

What is claimed is:

1. An isolated nucleic acid having a nucleotide sequence encoding an 82 kDa polypeptide whose amino acid sequence is set forth as SEQ. ID. NO. 6 present in gametocytes of *Eimeria maxima*, or the full complement of the nucleic acid.

2. The isolated nucleic acid of claim 1, wherein the nucleotide sequence is set forth as SEQ ID NO. 4.

3. The isolated nucleic acid of claim 1, wherein the isolated nucleic acid is a plasmid designated 82TRCHisb8 plasmid deposited under Australian Government Analytical Laboratories Accession No. NM01/22398.

4. The isolated nucleic acid of claim 1, further comprising an operatively linked promoter.

5. The isolated nucleic acid of claim 1, wherein the nucleic acid is a DNA molecule or an RNA molecule.

6. The isolated nucleic acid of claim 5, which is a cDNA molecule.

7. An isolated vector comprising a nucleotide sequence encoding an 82 kDa polypeptide whose amino acid sequence is set forth as SEQ. ID. NO. 6 present in gametocytes of *Eimeria maxima*, or the full complement of the nucleic acid.

8. The isolated vector of claim 7, wherein the vector is a plasmid.

9. An isolated host cell comprising a vector having a nucleotide sequence encoding a 82 kDa polypeptide whose amino acid sequence is set forth as SEQ. ID. NO. 6 present in gametocytes of *Eimeria maxima*, or the full complement of the nucleic acid.

10. The host cell of claim 9, wherein the cell is a transformed cell, a bacterial cell, a plant cell, an insect cell, or a mammalian cell.

11. The transformed cell of claim 10, wherein the cell is designated clone 82TRCHisb8 bacteria deposited under Australian Government Analytical Laboratories Accession No. NM01/22399.

12. A vaccine for immunizing a subject against infection by *Eimeria maxima* comprising a nucleic acid sequence encoding a 82 kDa polypeptide whose amino acid sequence is set forth as SEQ. ID. NO. 6 present in gametocytes of *Eimeria maxima*, the full complement of the nucleic acid, or the polypeptide.

13. The vaccine of claim 12, wherein the vaccine is designed to be administered by intravenous, intramuscular or intraperitoneal injection; or by spraying said vaccine into the nostrils of the subject.

14. The vaccine of claim 12, wherein the subject is an avian species.

15. The vaccine of claim 14, wherein avian species is chickens, ducks, turkeys, geese, bantams, quail, or pigeons.

16. The vaccine of claim 15, wherein the vaccine is designed to be administered in ovo.

17. The vaccine of claim 15, wherein the vaccine is designed to be administered to an air sac of an egg.

18. The vaccine of claim 12, further comprising a second nucleic acid encoding an antigen of *Eimeria maxima*, a vector comprising such nucleic acid, or a second polypeptide encoded by such nucleic acid.

* * * * *